US009643924B2

(12) United States Patent
Gotoh et al.

(10) Patent No.: US 9,643,924 B2
(45) Date of Patent: *May 9, 2017

(54) PIPERIDINE DERIVATIVE, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Ichihara (JP); Takahiro Kobayashi, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,999

(22) Filed: Aug. 4, 2015

(65) Prior Publication Data

US 2016/0039758 A1 Feb. 11, 2016

(30) Foreign Application Priority Data

Aug. 5, 2014 (JP) ................. 2014-159311

(51) Int. Cl.
*C09K 19/34* (2006.01)
*C07D 211/94* (2006.01)
*C09K 19/30* (2006.01)
*C09K 19/42* (2006.01)
*C09K 19/54* (2006.01)

(52) U.S. Cl.
CPC ........ *C07D 211/94* (2013.01); *C09K 19/3001* (2013.01); *C09K 19/3028* (2013.01); *C09K 19/3068* (2013.01); *C09K 19/3402* (2013.01); *C09K 19/3458* (2013.01); *C09K 19/3483* (2013.01); *C09K 19/42* (2013.01); *C09K 19/54* (2013.01); *C09K 2019/301* (2013.01); *C09K 2019/308* (2013.01); *C09K 2019/3009* (2013.01); *C09K 2019/3016* (2013.01); *C09K 2019/3021* (2013.01); *C09K 2019/3077* (2013.01); *C09K 2019/3083* (2013.01); *C09K 2019/3422* (2013.01)

(58) Field of Classification Search
CPC ..................................... C09K 19/34
See application file for complete search history.

(56) References Cited

U.S. PATENT DOCUMENTS

| 4,164,480 A | 8/1979 | Irick, Jr. et al. |
| 2006/0011886 A1 | 1/2006 | Li et al. |
| 2012/0268706 A1 | 10/2012 | Goebel et al. |

FOREIGN PATENT DOCUMENTS

| GB | 2132621 A | 7/1984 |
| JP | S59133234 A | 7/1984 |
| JP | 2004507607 A | 3/2004 |
| JP | 2012224632 A | 11/2012 |

*Primary Examiner* — Chanceity Robinson
(74) *Attorney, Agent, or Firm* — Hogan Lovells US LLP

(57) ABSTRACT

A liquid crystal composition is provided containing a compound that is effective in preventing photolysis of the liquid crystal composition, and has high solubility in the liquid crystal composition. A liquid crystal display device including the composition is also provided. The liquid crystal composition contains a compound represented by formula (1), and a liquid crystal display device uses the composition:

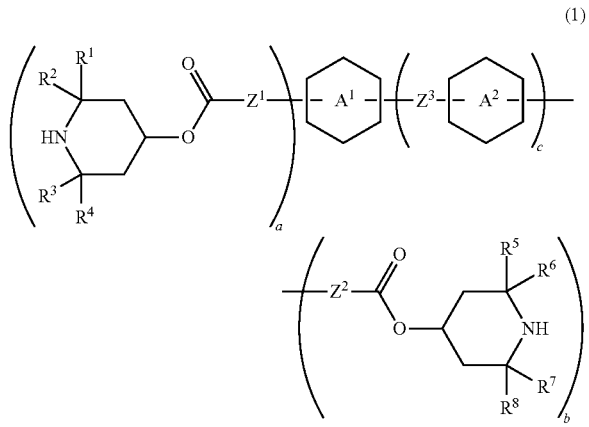

in which, in formula (1), $R^1$ to $R^8$ are hydrogen or alkyl having 1 to 4 carbons; ring $A^1$ and ring $A^2$ are cyclohexylene, phenylene, or naphthalenediyl; $Z^1$, $Z^2$ and $Z^3$ are a single bond; and a and b are independently 1 or 2, and c is 0, 1 or 2.

14 Claims, No Drawings

US 9,643,924 B2

PIPERIDINE DERIVATIVE, LIQUID CRYSTAL COMPOSITION AND LIQUID CRYSTAL DISPLAY DEVICE

TECHNICAL FIELD

The invention relates to a piperidine derivative useful as a light stabilizer, a liquid crystal composition containing the derivative and having a positive dielectric anisotropy, and a liquid crystal display device having the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type according to a production process. A classification based on a light source includes a reflective type utilizing natural light, a transmissive type utilizing backlight and a transflective type utilizing both the natural light and the backlight.

A liquid crystal display device includes a liquid crystal composition having a nematic phase. The composition has suitable characteristics. An AM device having good characteristics can be obtained by improving the characteristics of the composition. Table 1 below summarizes a relationship of the characteristics between two aspects. The characteristics of the composition are further described based on a commercially available AM device. A temperature range of the nematic phase relates to a temperature range in which the device can be used. A preferred maximum temperature of the nematic phase is approximately 70° C. or higher and a preferred minimum temperature of the nematic phase is approximately −10° C. or lower. Viscosity of the composition relates to a response time in the device. A short response time is preferred for displaying moving images on the device. A shorter response time even by one millisecond is desirable. Accordingly, a small viscosity in the composition is preferred. A small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity [1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Large contrast ratio and short response time |

[1] A liquid crystal composition can be injected into a liquid crystal cell in a shorter period of time.

An optical anisotropy of the composition relates to a contrast ratio in the device. According to the mode of the device, a large optical anisotropy or a small optical anisotropy, namely a suitable anisotropy is required. A product ($\Delta n \times d$) of the optical anisotropy ($\Delta n$) of the composition and a cell gap (d) in the device is designed so as to maximize the contrast ratio. A suitable value of the product depends on a type of the operating mode. A composition having a large optical anisotropy is preferred for a device having a small cell gap. A large value of dielectric anisotropy in the composition contributes to a low threshold voltage, a small electric power consumption and a large contrast ratio in the device. Accordingly, the large value of positive or negative dielectric anisotropy is preferred. A large specific resistance in the composition contributes to a large voltage holding ratio and a large contrast ratio in the device. Accordingly, a composition having a large specific resistance at room temperature and also at a temperature close to the maximum temperature of the nematic phase in an initial stage is preferred. A composition having a large specific resistance at room temperature and also at a temperature close to the maximum temperature of the nematic phase even after the device has been used for a long period of time is preferred. Stability of the composition to ultraviolet light and heat relates to a service life of the device. In the case where the stability is high, the device has a long service life. Such characteristics are preferred for an AM device for use in a liquid crystal projector, a liquid crystal television and so forth.

A liquid crystal composition containing a polymer is used for a liquid crystal display device having a polymer sustained alignment (PSA) mode. First, a composition to which a small amount of polymerizable compound is added is injected into the device. Next, the composition is irradiated with ultraviolet light while voltage is applied between substrates of the device. The polymerizable compound is polymerized to form a network structure of the polymer in the composition. In the composition, alignment of liquid crystal molecules can be controlled by the polymer, and therefore a response time of the device is shortened and image persistence is improved. Such an effect of the polymer can be expected for a device having a mode such as the TN mode, the ECB mode, the OCB mode, the IPS mode, the VA mode, the FFS mode and the FPA mode.

The liquid crystal composition is prepared by mixing liquid crystal compounds. An additive such as a polymerizable compound, a polymerization initiator, a polymerization inhibitor, an optically active compound, an antioxidant, an ultraviolet light absorber, a light stabilizer, a heat stabilizer and an antifoaming agent is added to the composition, when necessary. Among the additives, the light stabilizer is effective in preventing the liquid crystal compound from being decomposed by light from backlight or the sun. A high voltage holding ratio in the device is maintained due to such an effect, and therefore the service life of the device is prolonged. A hindered amine light stabilizer (HALS) is suitable for such a purpose. However, development of a light stabilizer having higher performance has been expected.

"Fusso Kagaku Nyumon 2010 Kiso to Oyo no Saizensen (Introduction to Fluorine Chemistry 2010 Forefront of Fundamentals and Applications)" describes that rise of melting point is caused together with rise of Tni to reduce compatibility with a matrix liquid crystal in p. 415. Here, higher compatibility of compound No. 85 having a biphenyl skeleton according to the invention, in comparison with comparative compound (S-1) formed of a benzene ring and having a lower melting point, is an advantage of the invention to show specificity of the invention.

(No.85)

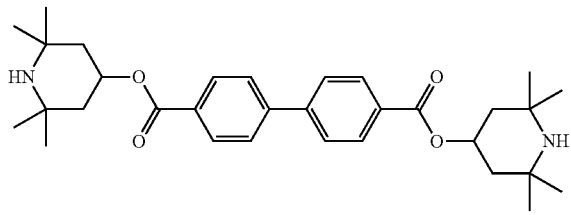

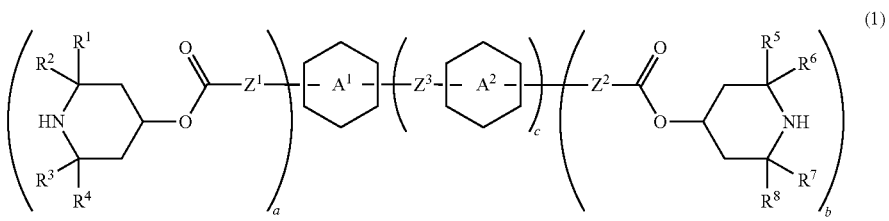

(S-1)

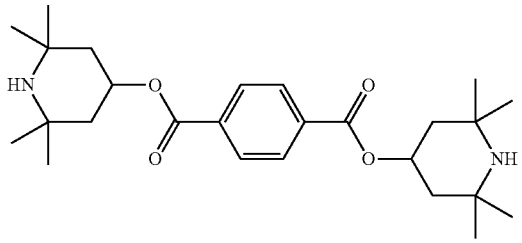

CITATION LIST

Patent Literature

Patent literature No. 1: JP S59-133234 A.
Patent literature No. 2: U.S. Pat. No. 4,164,480 B.
Patent literature No. 3: JP 2004-507607 A.
Patent literature No. 4: JP 2012-224632 A.

SUMMARY OF INVENTION

Technical Problem

A first object of the invention is to provide a compound that is effective in preventing photolysis of a liquid crystal composition, and has high solubility in the liquid crystal composition. A second object is to provide a liquid crystal composition containing the compound and satisfying at least one of characteristics such as a high maximum temperature of a nematic phase, a low minimum temperature of the nematic phase, a small viscosity, a suitable optical anisotropy, a large positive dielectric anisotropy, a large specific resistance, a high stability to ultraviolet light and heat, and a suitable elastic constant, or a liquid crystal composition having a suitable balance regarding at least two of the characteristics. The object is also to provide a liquid crystal composition having stability to light. A third object is to provide a liquid crystal display device including the composition and having characteristics such as a wide temperature range in which the device can be used, a short response time, a large voltage holding ratio, a low threshold voltage, a large contrast ratio and a long service life.

Solution to Problem

The invention concerns a liquid crystal composition containing at least one compound selected from the group of compounds represented by formula (1), and at least one compound selected from the group of compounds represented by formulas (2) to (8), and a liquid crystal display device including the composition:

The invention also concerns a compound represented by formulas (1-1) to (1-3).

Advantageous Effects of Invention

A first advantage of the invention is to provide a compound that is effective in preventing photolysis of a liquid crystal composition, and has high solubility in the liquid crystal composition. A second advantage is to provide a liquid crystal composition containing the compound and satisfying at least one of characteristics such as a high maximum temperature of a nematic phase, a low minimum temperature of a nematic phase, a small viscosity, a suitable optical anisotropy, a large positive dielectric anisotropy, a large specific resistance, a high stability to ultraviolet light and heat, and a suitable elastic constant, or a liquid crystal composition having a suitable balance regarding at least two of the characteristics. The advantage is also to provide a liquid crystal composition having stability to light. A third advantage is to provide a liquid crystal display device including the composition and having characteristics such as a wide temperature range in which the device can be used, a short response time, a high voltage holding ratio, a low threshold voltage, a large contrast ratio and a long service life.

DESCRIPTION OF EMBODIMENTS

Usage of terms herein is as described below. "Liquid crystal composition" and "liquid crystal display device" may be occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase and a smectic phase, and a compound having no liquid crystal phase but being mixed with the composition for the purpose of adjusting characteristics such as a temperature range of the nematic phase, viscosity and dielectric anisotropy. The compound has a six-membered ring, such as 1, 4-cyclohexylene and 1,4-phenylene, and has rod like molecular structure. "Polymerizable compound" includes a compound to be added to the composition for the purpose of forming a polymer in the composition.

The liquid crystal composition is prepared by mixing a plurality of liquid crystal compounds. A ratio (content) of the liquid crystal compounds is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer and an antifoaming agent is added to the liquid crystal composition, when necessary. A ratio (amount of addition) of the additive is expressed in terms of weight percent (% by weight) based on the weight of the liquid crystal composition in a manner similar to the ratio of the liquid crystal compounds. Weight parts per million (ppm) may be occasionally used. A ratio of the polymerization initiator and the polymerization inhibitor is exceptionally expressed based on the weight of the polymerizable compound.

"Higher limit of the temperature range of the nematic phase" may be occasionally abbreviated as "maximum temperature." "Lower limit of the temperature range of the nematic phase" may be occasionally abbreviated as "minimum temperature." An expression "having a large specific resistance" means that the composition has a large specific resistance at room temperature and also at a temperature close to the maximum temperature of the nematic phase in an initial stage, and that the composition has a large specific resistance at room temperature and also at a temperature close to the maximum temperature of the nematic phase even after the device has been used for a long period of time. An expression "having a large voltage holding ratio" means that the device has a large voltage holding ratio at room temperature and also at a temperature close to the maximum temperature of the nematic phase in an initial stage, and that the device has a large voltage holding ratio at room temperature and also at a temperature close to the maximum temperature of the nematic phase even after the device has been used for a long period of time. An expression "to increase the dielectric anisotropy" means that a value thereof positively increases for the composition having a positive dielectric anisotropy, and that the value negatively increases for the composition having a negative dielectric anisotropy.

A compound represented by formula (1) may be occasionally abbreviated as "compound (1)." At least one compound selected from the group of compounds represented by formula (1) may be occasionally abbreviated as "compound (1)." "Compound (1)" means one compound represented by formula (1), a mixture of two compounds represented thereby, or a mixture of three or more compounds represented thereby. A same rule applies also to any other compound represented by any other formula. An expression "at least one of 'A'" means that the number of 'A' is arbitrary. An expression "at least one of 'A' may be replaced by 'B'" means that, when the number of 'A' is 1, a position of 'A' is arbitrary, and when the number of 'A' is 2 or more, positions thereof can be selected without limitation. A same rule applies also to an expression "at least one of 'A' is replaced by 'B'."

A symbol of terminal group $R^{11}$ is used for a plurality of compounds in chemical formulas of component compounds. In the compounds, two groups represented by two of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule applies also to a symbol such as $R^{12}$ and Z". In formula (8), when i is 2, two of ring $D^1$ exists. In the compound, two rings represented by two of ring $D^1$ may be identical or different. A same rule applies also to two of arbitrary ring $D^1$ when i is larger than 2. A same rule applies also to $Z^{17}$ and ring $A^2$.

Symbols $A^1$, $B^1$, $C^1$ or the like surrounded by a hexagonal shape correspond to a six-membered ring and a condensed ring, such as ring $A^1$, ring $B^2$ and ring $C^1$, respectively. In formula (1), a line crossing ring $A^1$ indicates that arbitrary hydrogen on the ring may be replaced by monovalent group (1a) below.

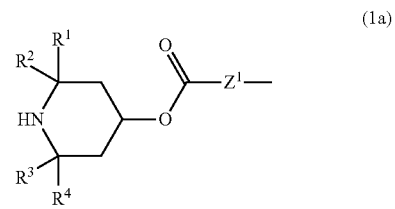

In formula (1), a subscript "a" is 1 or 2. The subscript "a" represents the number of groups to be subjected to replacement. When "a" is 1, ring $A^1$ is a divalent group, in which ring $A^1$ is defined by the divalent group such as 1,4-cyclohexylene and 1,4-phenylene. A case when "a" is 2 shows that hydrogen in the divalent group such as 1,4-cyclohexylene and 1,4-phenylene is further replaced by monovalent group (1a). A same rule applies also to ring $A^2$, a subscript "b" or the like. A same rule applies also to formula (1-1) or the like.

Then, 2-fluoro-1,4-phenylene means two divalent groups below. In a chemical formula thereof, fluorine may be leftward (L) or rightward (R). A same rule applies also to an asymmetrical divalent group derived from a ring, such as tetrahydropyran-2,5-diyl.

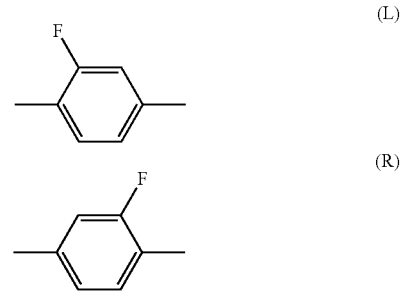

The invention includes items described below.

Item 1. A liquid crystal composition, containing at least one compound selected from the group of compounds represented by formula (1), and at least one compound selected from the group of compounds represented by formulas (2) to (4):

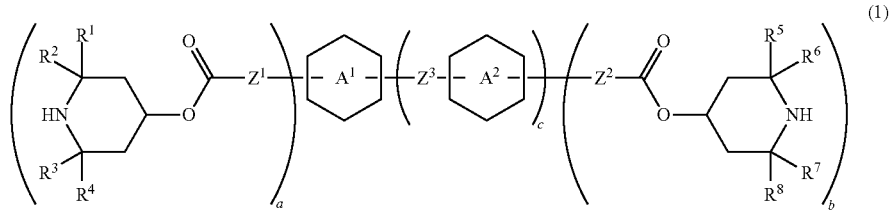

wherein, in formula (1), $R^1$, $R^2$, $R^3$, $R^4$, $R^5$, $R^6$, $R^7$ and $R^8$ are independently hydrogen or alkyl having 1 to 4 carbons;

ring $A^1$ and ring $A^2$ are independently cyclohexylene, cyclohexenylene, decahydronaphthalenediyl, dihydropyrandiyl, tetrahydropyrandiyl, dioxanediyl, phenylene, naphthalenediyl, pyrimidinediyl or pyridinediyl, and in the rings, at least one of hydrogen may be replaced by halogen, alkyl having 1 to 5 carbons, alkoxy having 1 to 5 carbons, or alkyl having 1 to 5 carbons in which at least one of hydrogen is replaced by halogen;

$Z^1$, $Z^2$ and $Z^3$ are independently a single bond or alkylene having 1 to 10 carbons, and in the alkylene, at least one of —$CH_2$— may be replaced by —O—, —S—, —CO—, —COO—, —OCO— or —$SiH_2$—, at least one of —$CH_2$—$CH_2$— may be replaced by —CH=CH— or —C≡C—, and in the groups, at least one of hydrogen may be replaced by halogen; and a and b are independently 1 or 2, and c is 0, 1 or 2;

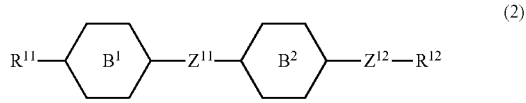

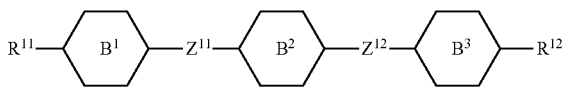

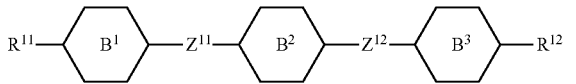

wherein, in formulas (2) to (4), $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 2. The liquid crystal composition according to item 1, wherein, in formula (1) described in item 1, $R^1$, $R^2$, $R^3$, $R^4$, $R^5$, $R^6$, $R^7$ and $R^8$ are independently alkyl having 1 to 4 carbons;

ring $A^1$ and ring $A^2$ are independently 1,4-cyclohexylene, 1,4-cyclohexenylene, decahydronaphthalene-2,6-diyl, 3,4-dihydro-2H-pyran-3,6-diyl, 3,4-dihydro-2H-pyran-2,5-diyl, 3,6-dihydro-2H-pyran-2,5-diyl, tetrahydropyran-2,5-diyl, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl, and in the rings, at least one of hydrogen may be replaced by fluorine, chlorine, alkyl having 1 to 5 carbons, alkoxy having 1 to 5 carbon, or alkyl having 1 to 5 carbons in which at least one of hydrogen is replaced by fluorine or chlorine;

$Z^1$, $Z^2$ and $Z^3$ are independently a single bond or alkylene having 1 to 10 carbons, and in the alkylene, at least one of —$CH_2$— may be replaced by —O—, —COO— or —OCO—, at least one of —$CH_2$—$CH_2$— may be replaced by —CH=CH—, and in the groups, at least one of hydrogen may be replaced by fluorine or chlorine; and a and b are independently 1 or 2, and c is 0, 1 or 2.

Item 3. The liquid crystal composition according to item 1 or 2, wherein, in formula (1) described in item 1, $R^1$, $R^2$, $R^3$, $R^4$, $R^5$, $R^6$, $R^7$ and $R^8$ are independently alkyl having 1 to 4 carbons; ring $A^1$ and ring $A^2$ are independently 1,4-cyclohexylene, 1,4-cyclohexenylene or decahydronaphthalene-2,6-diyl, and in the rings, at least one of hydrogen may be replaced by fluorine or chlorine;

$Z^1$, $Z^2$ and $Z^3$ are independently a single bond or alkylene having 1 to 10 carbons, and in the alkylene, at least one of —$CH_2$— may be replaced by —O—, and at least one of hydrogen may be replaced by fluorine; and a and b are independently 1 or 2, and c is 0, 1 or 2.

Item 4. The liquid crystal composition according to item 1 or 2, wherein, in formula (1) described in item 1, $R^1$, $R^2$, $R^3$, $R^4$, $R^5$, $R^6$, R and $R^8$ are independently alkyl having 1 to 4 carbons;

ring $A^1$ and ring $A^2$ are independently 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl, and in the rings, at least one of hydrogen may be replaced by fluorine, chlorine, methyl, methoxy, fluoromethyl, difluoromethyl or trifluoromethyl;

$Z^1$, $Z^2$ and $Z^3$ are independently a single bond or alkylene having 1 to 10 carbons, and in the alkylene, at least one of —$CH_2$— may be replaced by —O—, and at least one of hydrogen may be replaced by fluorine; and a and b are independently 1 or 2, and c is 0, 1 or 2.

Item 5. The liquid crystal composition according to any one of items 1 to 4, further containing at least one compound selected from the group of compounds represented by formulas (5) to (7):

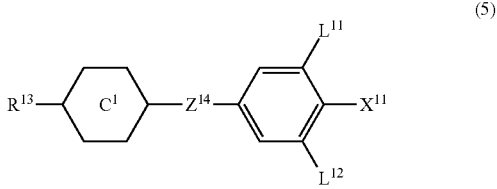

-continued (6)
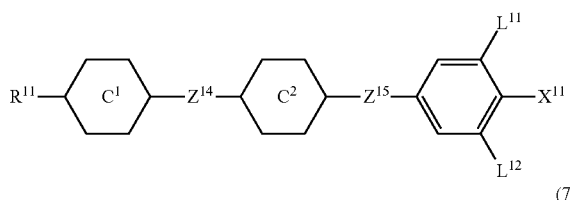

(7)
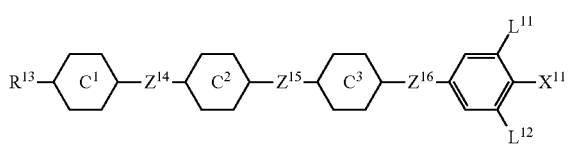

wherein, in formulas (5) to (7), $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 6. The liquid crystal composition according to any one of items 1 to 5, further containing at least one compound selected from the group of compounds represented by formula (8):

(8)
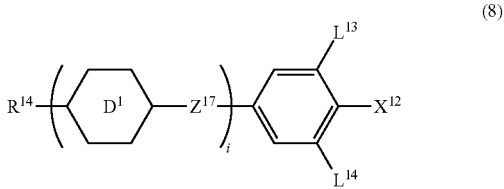

wherein, in formula (8), $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{12}$ is —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 7. The liquid crystal composition according to any one of items 1 to 6, further containing at least one of a polymerizable compound, a polymerization initiator, a polymerization inhibitor, an optically active compound, an antioxidant, an ultraviolet light absorber, a light stabilizer, a heat stabilizer and an antifoaming agent.

Item 8. A liquid crystal display device, including at least one liquid crystal composition according to any one of items 1 to 7.

Item 9. A compound represented by formulas (1-1) to (1-3):

(1-1)
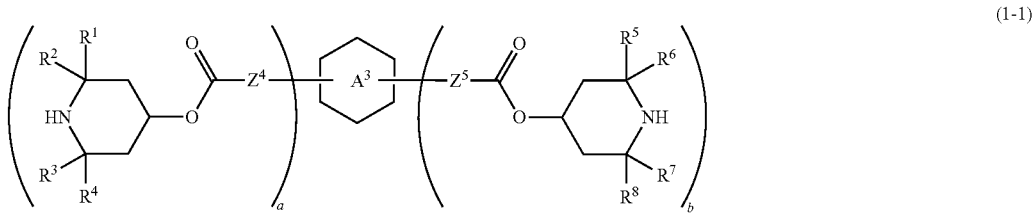

(1-2)
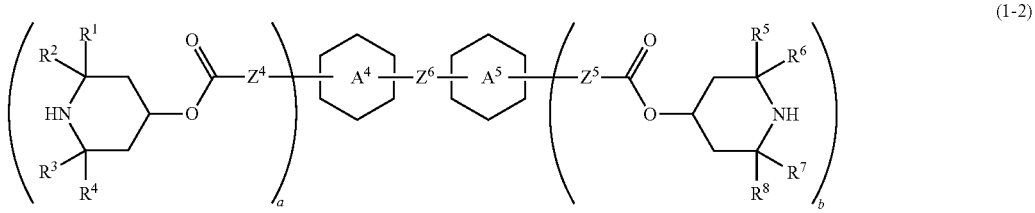

(1-3)
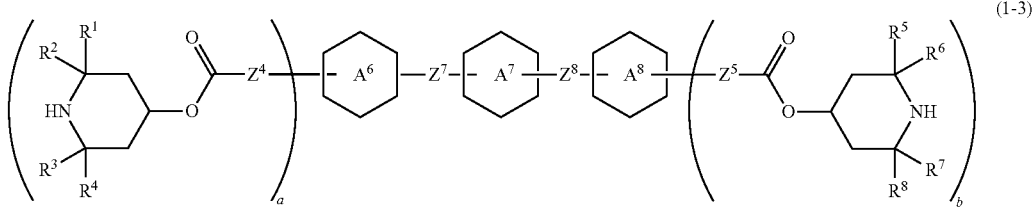

wherein, in formulas (1-1) to (1-3), $R^1$, $R^2$, $R^3$, $R^4$, $R^5$, $R^6$, $R^7$ and $R^8$ are independently hydrogen or alkyl having 1 to 4 carbons;

ring $A^3$ is decahydronaphthalene-2,6-diyl, 3,4-dihydro-2H-pyran-3,6-diyl, 3,4-dihydro-2H-pyran-2,5-diyl, 3,6-dihydro-2H-pyran-2,5-diyl, 1,3-dioxane-2,5-diyl, tetrahydropyran-2,5-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl, and in the rings, at least one of hydrogen may be replaced by halogen, alkyl having 1 to 5 carbons, alkoxy having 1 to 5 carbons, or alkyl having 1 to 5 carbons in which at least one of hydrogen is replaced by halogen;

ring $A^4$, ring $A^5$, ring $A^6$, ring $A^7$ and ring $A^8$ are independently 1,4-cyclohexylene, 1,4-cyclohexenylene, decahydronaphthalene-2,6-diyl, 3,4-dihydro-2H-pyran-3,6-diyl, 3,4-dihydro-2H-pyran-2,5-diyl, 3,6-dihydro-2H-pyran-2,5-diyl, tetrahydropyran-2,5-diyl, 1,3-dioxane-2,5-diyl, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl, and in the rings, at least one of hydrogen may be replaced by halogen, alkyl having 1 to 5 carbons, alkoxy having 1 to 5 carbons, or alkyl having 1 to 5 carbons in which at least one of hydrogen is replaced by halogen;

$Z^4$, $Z^5$, $Z^6$, $Z^7$ and $Z^8$ are independently a single bond or alkylene having 1 to 10 carbons, and in the alkylene, at least one of —$CH_2$— may be replaced by —O—, —S—, —CO—, —COO— or —OCO—, at least one of —$CH_2$—$CH_2$— may be replaced by —CH=CH— or —C≡C—, and in the groups, at least one of hydrogen may be replaced by fluorine or chlorine; and a and b are independently 1 or 2.

Item 10. The compound according to item 9, wherein, in formulas (1-1) to (1-3) described in item 9, $R^1$, $R^2$, $R^3$, $R^4$, $R^5$, $R^6$, R and $R^8$ are independently hydrogen or alkyl having 1 to 4 carbons;

ring $A^3$ is decahydronaphthalene-2,6-diyl, naphthalene-2,6-diyl, or naphthalene-2,6-diyl in which at least one of hydrogen is replaced by fluorine;

ring $A^4$, ring $A^5$, ring $A^6$, ring $A^7$ and ring $A^8$ are independently 1,4-cyclohexylene, 1,4-cyclohexenylene, decahydronaphthalene-2,6-diyl, 1,4-phenylene, 1,4-phenylene in which at least one of hydrogen is replaced by fluorine, or naphthalene-2,6-diyl;

$Z^4$, $Z^5$, $Z^6$, $Z^7$ and $Z^8$ are independently a single bond or alkylene having 1 to 10 carbons, and in the alkylene, at least one of —$CH_2$— may be replaced by —O—, and at least one of —$CH_2$—$CH_2$— may be replaced by —CH=CH—; and a and b are independently 1 or 2.

Item 11. The compound according to item 9, wherein, in formulas (1-1) to (1-3) described in item 9, $R^1$, $R^2$, $R^3$, $R^4$, $R^5$, $R^6$, R and $R^8$ are methyl;

ring $A^3$ is naphthalene-2,6-diyl;

ring $A^4$, ring $A^5$, ring $A^6$, ring $A^7$ and ring $A^8$ are independently 1,4-phenylene, 2-fluoro-1,4-phenylene or naphthalene-2,6-diyl;

$Z^4$, $Z^5$, $Z^6$, $Z^7$ and $Z^8$ are a single bond; and a and b are independently 1 or 2.

Item 12. The compound according to item 9, represented by any one of formulas (1-1-1), (1-2-1), (1-2-2), (1-2-3) and (1-2-4):

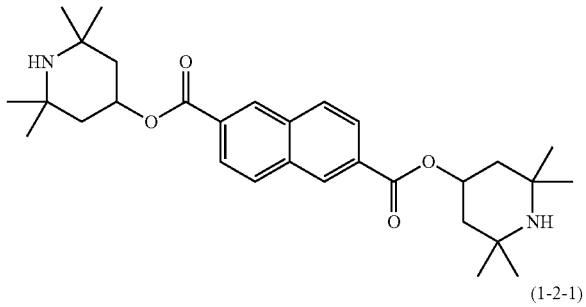

(1-1-1)

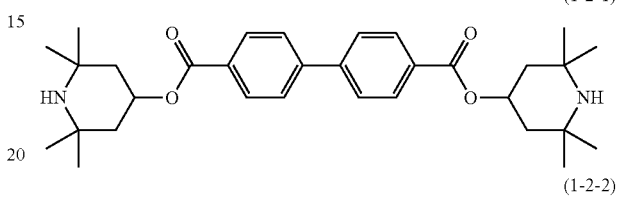

(1-2-1)

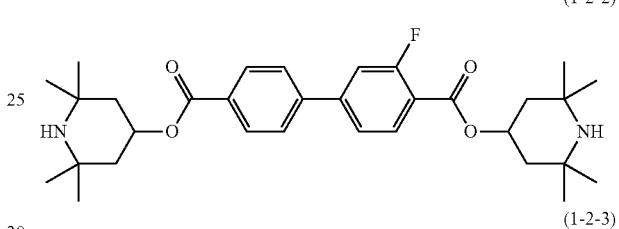

(1-2-2)

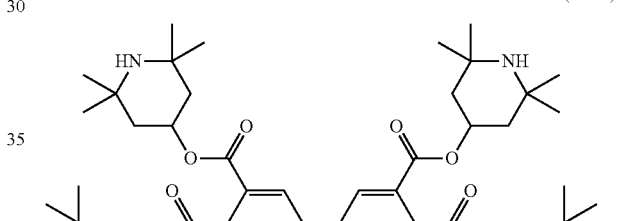

(1-2-3)

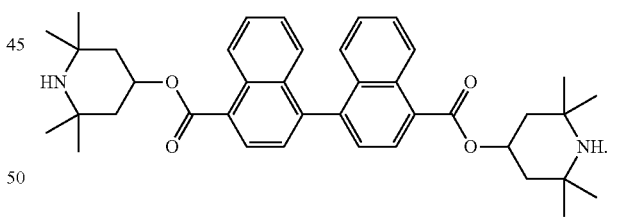

(1-2-4)

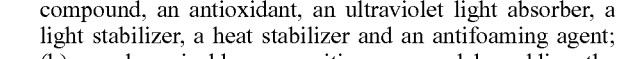

Item 13. A liquid crystal composition, containing at least one compound according to any one of items 9 to 12.

Item 14. A liquid crystal display device, including at least one liquid crystal composition according to item 13.

The invention further includes the following items: (a) the liquid crystal composition, further containing at least two additives such as a polymerizable compound, a polymerization initiator, a polymerization inhibitor, an optically active compound, an antioxidant, an ultraviolet light absorber, a light stabilizer, a heat stabilizer and an antifoaming agent; (b) a polymerizable composition prepared by adding the polymerizable compound to the liquid crystal composition; (c) a liquid crystal composite prepared by polymerizing the polymerizable composition; (d) a polymer sustained alignment (PSA) mode AM device including the liquid crystal composite; (e) use of compound (1) as the light stabilizer; (f) use of compound (1) as the heat stabilizer; (g) use in combination of a light stabilizer different from compound (1) with compound (1); (h) use as an optically activity composition by adding the optically active compound to the liquid crystal composition.

The compound, a synthesis method, the liquid crystal composition and the liquid crystal display device according to the invention will be described in the order.

1. Compound (1)

Compound (1) of the invention has a piperidine ring together with an ester bond, and therefore is useful as a hindered amine light stabilizer. The compound can be added to the liquid crystal composition. The reason is that the compound has high solubility in the liquid crystal composition. Preferred compound (1) has a rod like molecular structure, and therefore the solubility thereof in the liquid crystal composition is much higher. Preferred compound (1) has the high solubility at a low temperature such as approximately −20° C. The liquid crystal composition is a mixture of the liquid crystal compounds. Compound (1) is effective in preventing the liquid crystal compound from being decomposed by light from backlight or the sun. The compound is also effective as the heat stabilizer.

When the liquid crystal display device is used for a long period of time, the liquid crystal compound therein tends to be decomposed by light to produce a decomposition product. The product is an impurity, and therefore is unfavorable for the device. The reason is that the impurity causes a phenomenon such as reduction of contrast, occurrence of display unevenness and image persistence. The phenomenon can be easily identified by visual observation, and is significantly conspicuous even if a degree thereof is only a little. Accordingly, the light stabilizer that generates the impurity in an amount smaller even by 1% in comparison with a conventional light stabilizer is preferred. Compound (1) is such a light stabilizer.

Preferred examples of compound (1) are described. Preferred examples of substituent R, ring A and a bonding group Z in compound (1) are also applied to a subordinate formula of formula (1) for compound (1). In compound (1), characteristics can be arbitrarily adjusted by suitably combining kinds of the groups. Compound (1) may contain an isotope such as $^2$H (deuterium) and $^{13}$C in an amount larger than an amount of natural abundance because no significant difference exists in the characteristics of the compound.

anediyl, phenylene, naphthalenediyl, pyrimidinediyl or pyridinediyl, and in the rings, at least one of hydrogen may be replaced by halogen, alkyl having 1 to 5 carbons, alkoxy having 1 to 5 carbons, or alkyl having 1 to 5 carbons in which at least one of hydrogen is replaced by halogen.

Preferred examples of ring $A^1$ and ring $A^2$ include 1,4-cyclohexylene, 1,4-cyclohexenylene, decahydronaphthalene-2,6-diyl, dihydropyrandiyl, tetrahydropyran-2,5-diyl, 1,3-dioxane-2,5-diyl, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl. In the rings, at least one of hydrogen may be replaced by fluorine, chlorine, alkyl having 1 to 5 carbons, alkoxy having 1 to 5 carbons, or alkyl having 1 to 5 carbons in which at least one of hydrogen is replaced by fluorine or chlorine.

Preferred examples of dihydropyrandiyl include 3,4-dihydro-2H-pyran-3,6-diyl (pr-1), 3,4-dihydro-2H-pyran-2,5-diyl (pr-2) or 3,6-dihydro-2H-pyran-2,5-diyl (pr-3).

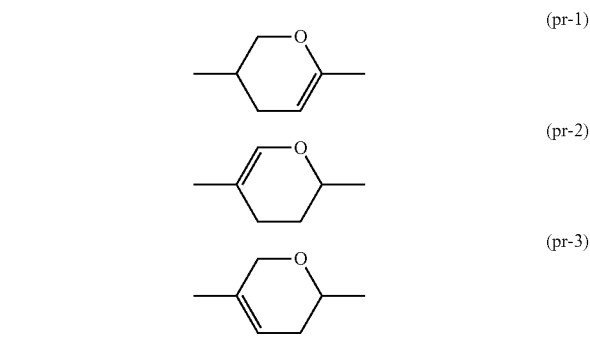

Further preferred examples include 1,4-cyclohexylene, 1,4-cyclohexenylene or decahydronaphthalene-2,6-diyl. In the rings, at least one of hydrogen may be replaced by fluorine or chlorine.

Further preferred examples include 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl. In the rings, at least one of hydrogen may be replaced by fluorine, chlorine, methyl, methoxy,

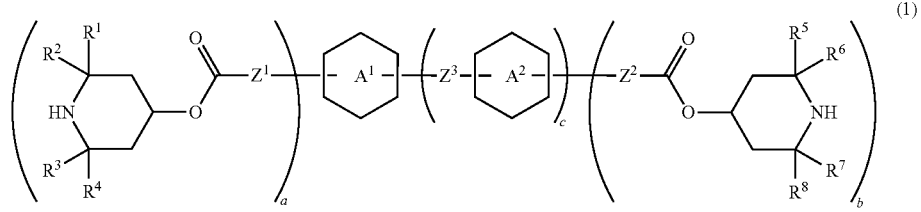

(1)

In formula (1), $R^1$, $R^2$, $R^3$, $R^4$, $R^5$, $R^6$, $R^7$ and $R^8$ are independently hydrogen or alkyl having 1 to 4 carbons. Preferred examples of $R^1$ to $R^8$ include methyl, ethyl, propyl or butyl. Further preferred examples include methyl or ethyl. Most preferred examples include methyl.

In formula (1), ring $A^1$ and ring $A^2$ are independently cyclohexylene, cyclohexenylene, decahydronaphthalenediyl, dihydropyrandiyl, tetrahydropyrandiyl, dioxfluoromethyl, difluoromethyl or trifluoromethyl. Most preferred examples include 1,4-phenylene, 2-fluoro-1,4-phenylene, naphthalene-1,4-diyl or naphthalene-1,5-diyl.

In formula (1), $Z^1$, $Z^2$ and $Z^3$ are independently a single bond or alkylene having 1 to 10 carbons, and in the alkylene, at least one of —$CH_2$— may be replaced by —O—, —S—, —CO—, —COO—, —OCO— or —$SiH_2$—, at least one of —$CH_2$—$CH_2$— may be replaced by —CH=CH— or —C≡C—, and in the groups, at least one of hydrogen may be replaced by halogen. Preferred example of $Z^1$, $Z^2$ and $Z^3$ include a single bond or alkylene having 1 to 10 carbons, and in the alkylene, at least one of —$CH_2$— may be replaced by —O—, —COO— or —OCO—, at least one of —$CH_2$—$CH_2$— may be replaced by —CH=CH—, and in the groups, at least one of hydrogen may be replaced by fluorine or chlorine. Further preferred examples include a single bond or alkylene having 1 to 10 carbons, and in the alkylene, at least one of —$CH_2$— may be replaced by —O—, and at least one of hydrogen may be replaced by fluorine. Most preferred examples include a single bond.

In formula (1), a and b are independently 1 or 2, and c is 0, 1 or 2. A sum of a and b is 2 to 4. Compound (1) has two, three or four monovalent groups (1a). Preferred compound (1) has two or three monovalent groups (1a). Further preferred compound (1) has two monovalent groups (1a). In most preferred compound (1), a and b are 1. Then, c is 0, 1 or 2, and therefore compound (1) has one, two or three of ring A. When c is 0, preferred ring $A^1$ is naphthalenediyl. Further preferred ring $A^1$ is naphthalene-1,4-diyl or naphthalene-1,5-diyl. When c is 1, preferred ring $A^1$ and ring $A^2$ are phenylene, phenylene in which at least one of hydrogen is replaced by fluorine, or naphthalenediyl. Further preferred ring $A^1$ and ring $A^2$ are 1,4-phenylene, 2-fluoro-1,4-phenylene, naphthalene-1,4-diyl or naphthalene-1,5-diyl.

Compound (1) having objective characteristics can be obtained by suitably selecting a combination of substituent R, ring A and a bonding group Z with referring to preferred examples described above. Preferred examples of compound (1) include compound (1-1), (1-2) or (1-3) described in item 9. Further preferred examples include compound (1-1-1), (1-2-1), (1-2-2), (1-2-3) or (1-2-4) described in item 12.

2. Synthesis Method

A method for preparing compound (1) is described. Compound (1) can be prepared by suitably combining techniques in synthesis organic chemistry. A method for introducing an objective terminal group, ring and bonding group into a starting material is described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.).

2-1. Formation of Bonding Group Z

First, a scheme is shown with regard to a method of forming bonding groups $Z^1$ to $Z^3$. Next, reactions described in schemes described in sections (1) to (11) are described. In the scheme, $MSG^1$ (or $MSG^2$) is a monovalent organic group having at least one ring. A plurality of $MSG^1$ (or $MSG^2$) used in the scheme may be identical or different. Compounds (1A) to (1K) correspond to compound (1).

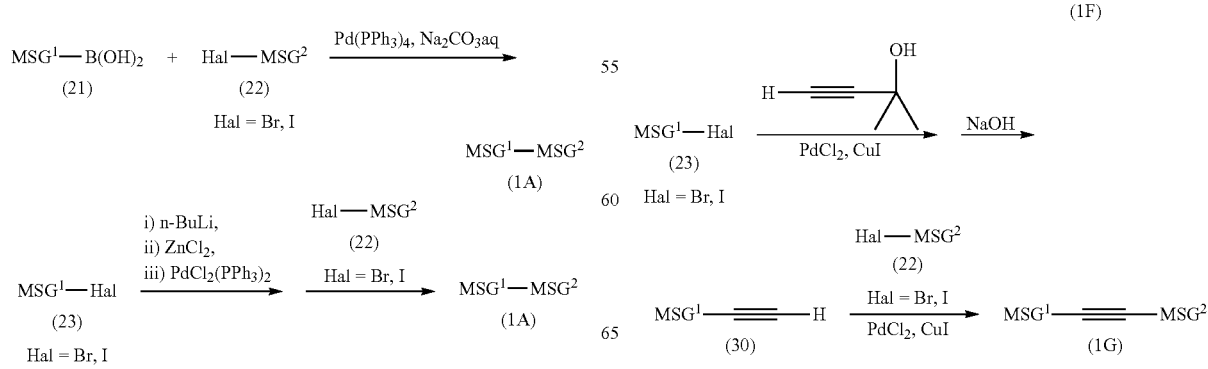

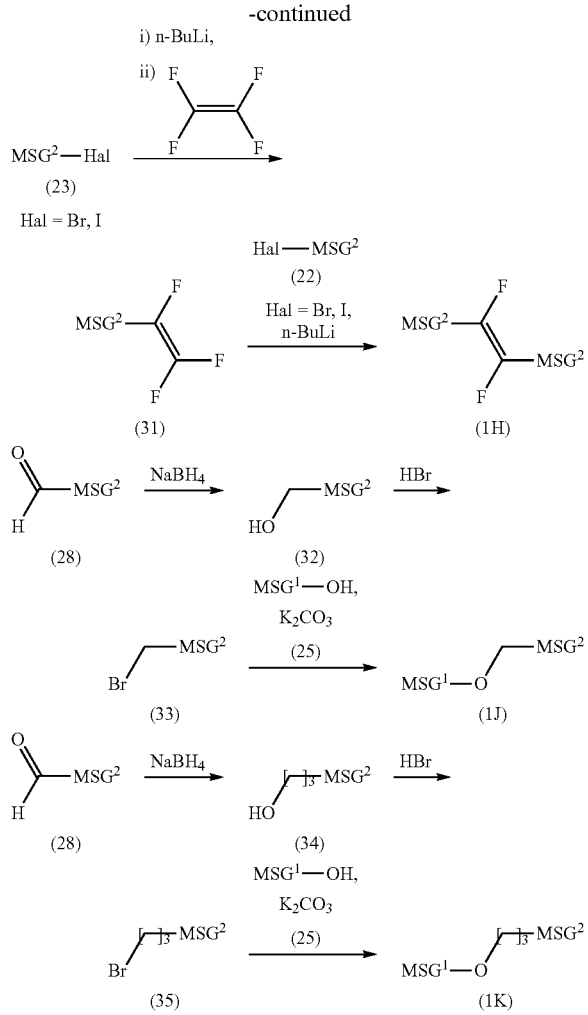

(1) Formation of a Single Bond

Compound (1A) is prepared by allowing aryl boronic acid (21) to react, in the presence of an aqueous carbonate solution and a catalyst such as tetrakis(triphenylphosphine)palladium, with compound (22) prepared according to a publicly known method. Compound (1A) is also prepared by allowing compound (23) prepared according to a publicly known method to react with n-butyllithium and subsequently with zinc chloride, and further with compound (22) in the presence of a catalyst such as dichlorobis(triphenylphosphine)palladium.

(2) Formation of —COO— and —OCO—

Carboxylic acid (24) is obtained by allowing compound (23) to react with n-butyllithium and subsequently with carbon dioxide. Compound (1B) having —COO— is prepared by dehydrating compound (24) and phenol (25) prepared from compound (21) according to a publicly known method, in the presence of 1,3-dicyclohexylcarbodiimide (DCC) and 4-dimethylaminopyridine (DMAP). A compound having —OCO— is also prepared according to the method.

(3) Formation of —CF$_2$O— and —OCF$_2$—

Compound (26) is obtained by treating compound (1B) with a thiation reagent such as Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768. A compound having —OCF$_2$— can be also prepared according to the method. The bonding group can be also formed according to the method described in Peer. Kirsch et al., Angew. Chem. Int. Ed. 2001, 40, 1480.

(4) Formation of —CH═CH—

Aldehyde (28) is obtained by treating compound (23) with n-butyllithium and then allowing the treated compound to react with formamide such as N,N-dimethylformamide (DMF). Compound (1D) is prepared by allowing phosphorus ylide generated by treating phosphonium salt (27) prepared according to a publicly known method with a base such as potassium t-butoxide to react with aldehyde (28). A cis isomer may be generated depending on reaction conditions, and therefore the cis isomer is isomerized to a trans isomer according to a publicly known method, when necessary.

(5) Formation of —CH$_2$CH$_2$—

Compound (1E) is prepared by hydrogenating compound (1D) in the presence of a catalyst such as palladium on carbon.

(6) Formation of —(CH$_2$)$_4$—

A compound having —(CH$_2$)$_2$—CH═CH— is obtained by using phosphonium salt (29) in place of phosphonium salt (27) according to the method in section (5). Compound (1F) is prepared by performing catalytic hydrogenation of the compound obtained.

(7) Formation of —C≡C—

Compound (30) is obtained by allowing compound (23) to react with 2-methyl-3-butyn-2-ol in the presence of a catalyst including dichloropalladium and copper halide, and then performing deprotection under basic conditions. Compound (1G) is prepared by allowing compound (30) to react with compound (22) in the presence of the catalyst including dichloropalladium and copper halide.

(8) Formation of —CF═CF—

Compound (31) is obtained by treating compound (23) with n-butyllithium and then allowing the treated compound to react with tetrafluoroethylene. Compound (1H) is prepared by treating compound (22) with n-butyllithium and then allowing the treated compound to react with compound (31).

(9) Formation of —CH$_2$O— and —OCH$_2$—

Compound (32) is obtained by reducing compound (28) with a reducing agent such as sodium borohydride. Compound (33) is obtained by halogenating the obtained compound with hydrobromic acid or the like. Compound (1J) is prepared by allowing compound (33) to react with compound (25) in the presence of potassium carbonate or the like.

(10) Formation of —(CH$_2$)$_3$O— and —O(CH$_2$)$_3$—

Compound (1K) is prepared by using compound (34) in place of compound (32) in a manner similar to preceding section (9).

(11) Formation of —(CF$_2$)$_2$—

A compound having —(CF$_2$)$_2$— is obtained by fluorinating diketone (—COCO—) with sulfur tetrafluoride, in the presence of a hydrogen fluoride catalyst, according to the method described in J. Am. Chem. Soc., 2001, 123, 5414.

2-2. Formation of Ring A

Next, a synthesis method with regard to ring A$^1$ or ring A$^2$ is described. A starting material is commercially available or the synthesis method is well known with regard to a ring such as 1,4-cyclohexylene, 1,3-dioxane-2,5-diyl, 1,4-phenylene, 2-fluoro-1,4-phenylene, pyridine-2,5-diyl or pyrimidine-2,5-diyl. Then, compounds (64), (67) and (71) below are described.

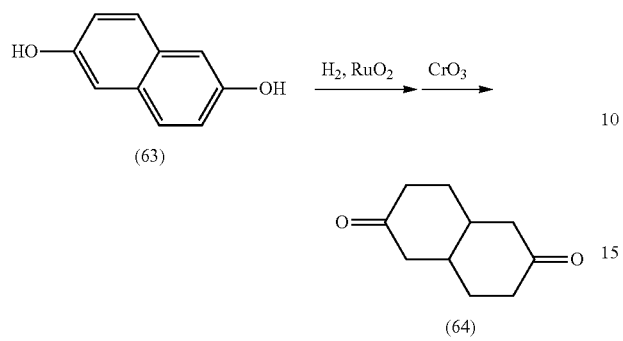

(63)

(64)

Decahydronaphthalene-2,6-dione (64) is a starting material of a compound having decahydronaphthalene-2,6-diyl. Compound (64) is prepared by reducing diol (63) with hydrogen in the presence of ruthenium oxide, and then being oxidized with chromic oxide, according to the method described in JP 2000-239564 A.

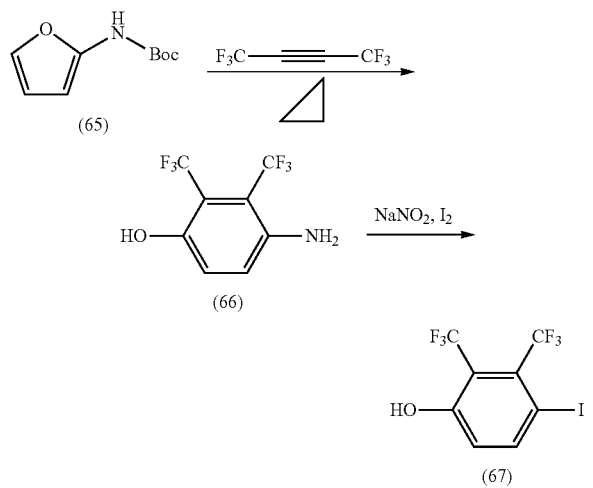

(65)

(66)

(67)

A structural unit of 2,3-(bistrifluoromethyl)phenylene is prepared by the method described in Org. Lett., 2000, 2 (21), 3345. Aniline (66) is prepared by allowing a Diels Alder reaction between furan (65) and 1,1,1,4,4,4-hexafluoro-2-butyne at a high temperature. Iodide (67) is obtained by carrying out a Sand Mayer reaction according to the method described in Org. Synth. Coll., Vol. 2, 1943, 355. The compound is converted into compound (1) according to a technique in general synthesis organic chemistry.

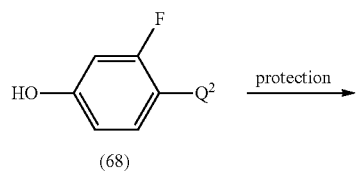

(68)

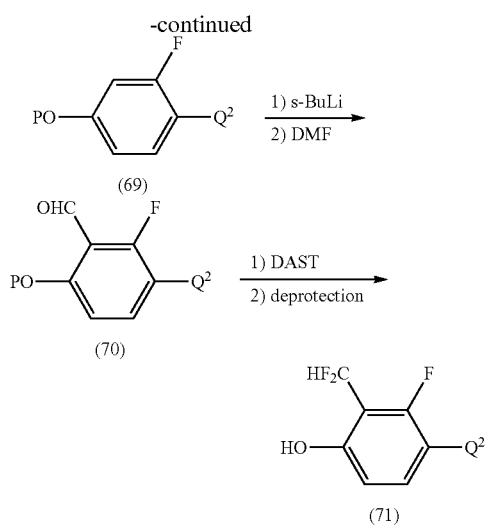

(69)

(70)

(71)

A structural unit of 2-difluoromethyl-3-fluorophenylene is prepared by a method as described below. Compound (69) is obtained by protecting a hydroxyl group of compound (68) with a suitable protective group. P means the protective group. Aldehyde (70) is obtained by treating compound (69) with sec-butyllithium, and subsequently allowing the treated compound to react with N,N-dimethylformamide (DMF). Phenol (71) is obtained by fluorinating the compound by (diethylamino)sulfur trifluoride (DAST) and subsequently deprotecting the resulting material. The compound is converted into compound (1) according to a technique in general synthesis organic chemistry.

2-3. Formation of Divalent Group (1a)

Then, 4-hydroxypiperidine or 4-hydroxy-2,2,6,6-tetramethylpiperidine is commercially available. Compound (1) can be derived by esterification using the materials above as a starting material.

3. Liquid Crystal Composition

The liquid crystal composition of the invention contains compound (1) (or a subordinate compound such as compounds (1-1) to (1-3)) as component A. Compound (1) is suitable for preventing the liquid crystal composition from being decomposed by light or heat. The composition contains compound (1) as component A, and preferably further contains a compound selected from components B, C and D described below. Component B includes compounds (2) to (4). Component C includes compounds (5) to (7). Component D includes compound (8). When the composition is prepared, components B, C and D are preferably selected by taking positive or negative dielectric anisotropy and magnitude of dielectric anisotropy or the like into consideration. A composition in which the components are suitably selected satisfies at least one of characteristics such as a high maximum temperature, a low minimum temperature, a small viscosity, a suitable optical anisotropy (namely, a large optical anisotropy or a small optical anisotropy), a large positive dielectric anisotropy and a suitable elastic constant (namely, a large elastic constant or a small elastic constant).

A preferred ratio of compound (1) is approximately 0.01% by weight or more in order to maintain the high stability to ultraviolet light, and approximately 5% by weight or less in order to be dissolved into the liquid crystal composition, based on the weight of the liquid crystal composition. A further preferred ratio is in the range of approximately 0.05% by weight to approximately 2% by weight. A most preferred ratio is in the range of approximately 0.05% by weight to approximately 1% by weigh.

Component B is a compound in which two terminal groups are alkyl or the like. Preferred examples of component B include compounds (2-1) to (2-11), compounds (3-1) to (3-19) and compounds (4-1) to (4-7). In the compound of component B, $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine.

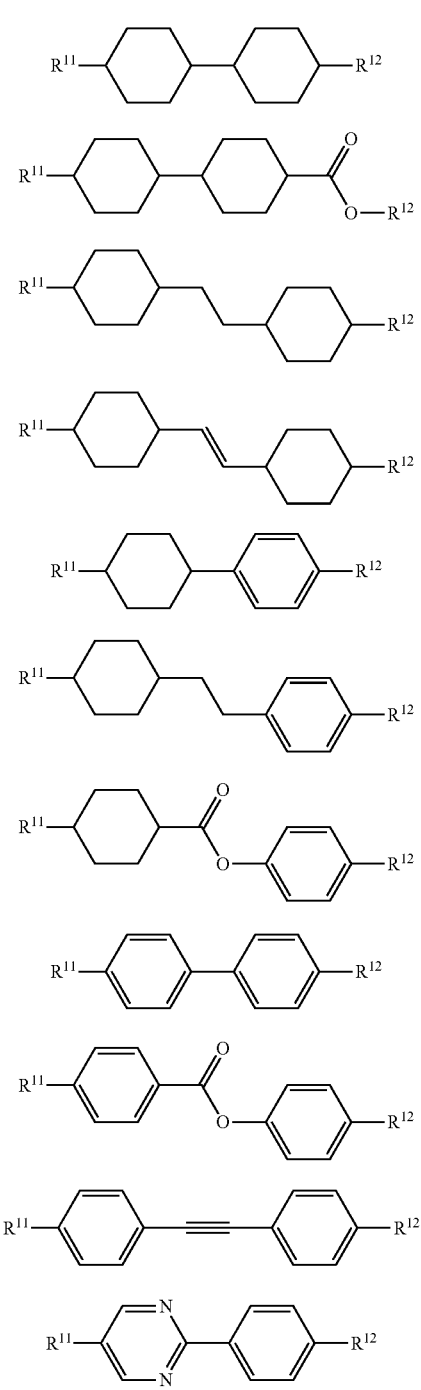

-continued

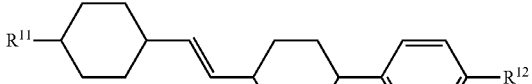
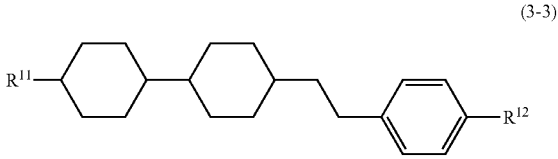
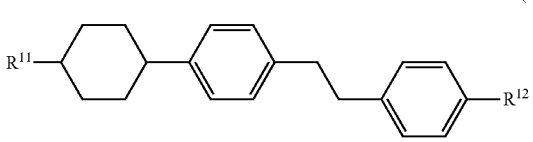
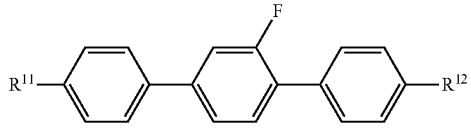
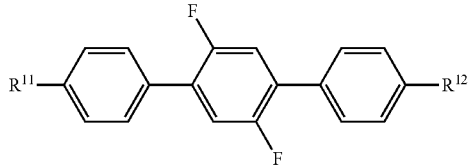
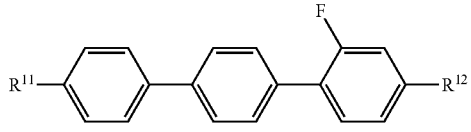
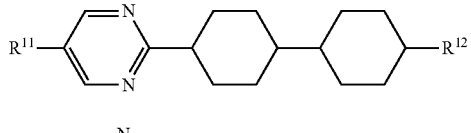
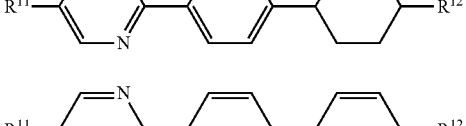
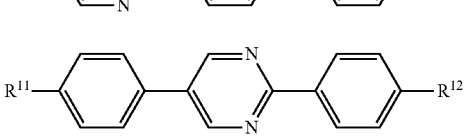

(3-13)
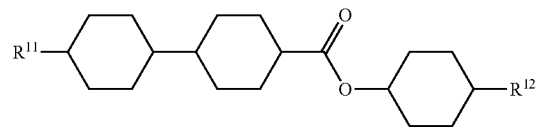

(3-14)
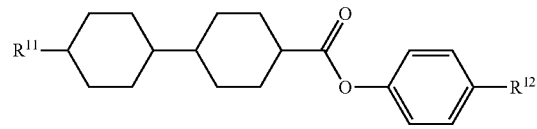

(3-15)
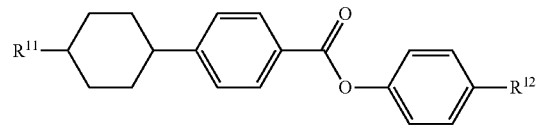

(3-16)
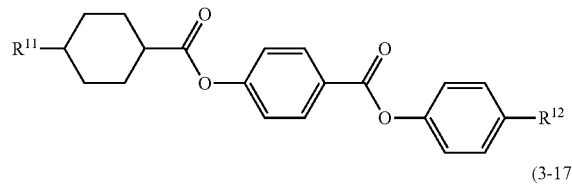

(3-17)
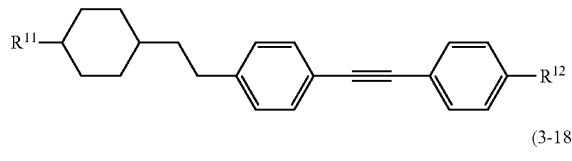

(3-18)
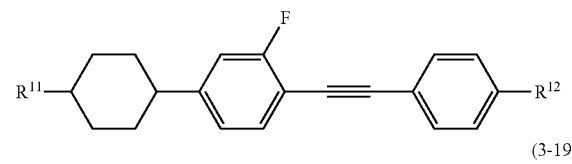

(3-19)
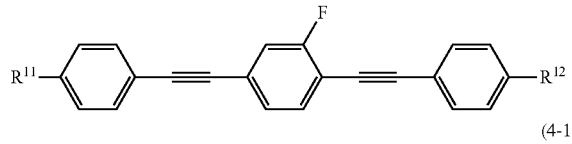

(4-1)
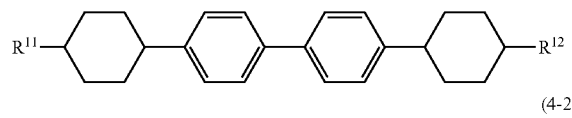

(4-2)
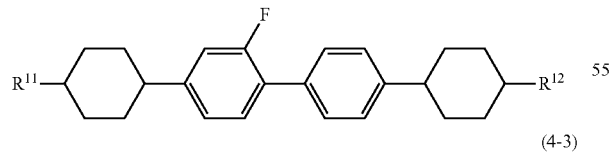

(4-3)
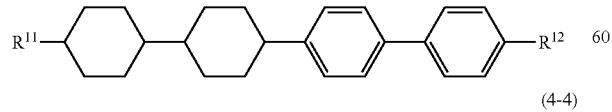

(4-4)
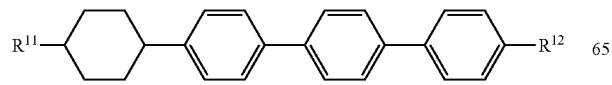

(4-5)
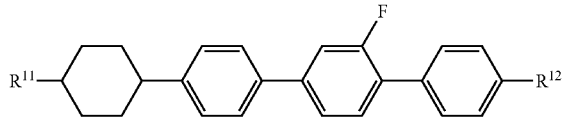

(4-6)
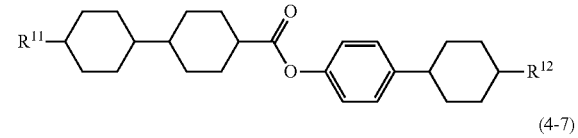

(4-7)
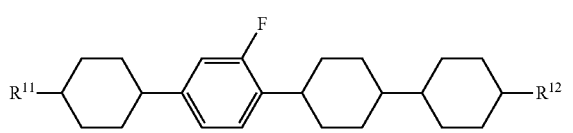

Component B has a small absolute value of dielectric anisotropy, and therefore is a compound close to neutrality. Compound (2) is effective mainly in adjusting the viscosity or the optical anisotropy. Compounds (3) and (4) are effective in extending the temperature range of the nematic phase by increasing the maximum temperature, or in adjusting the optical anisotropy.

As a content of component B is increased, the dielectric anisotropy decreases, but the viscosity of the composition also decreases. Thus, as long as a desired value of threshold voltage of the device is met, the content is preferably as large as possible. Therefore, when a composition for the IPS mode, the VA mode or the like is prepared, the content of component (B) is preferably approximately 30% by weight or more, and further preferably, approximately 40% by weight or more, based on the weight of the liquid crystal composition.

Component C is a compound having a halogen-containing group or a fluorine-containing group at a right terminal. Preferred examples of component C include compounds (5-1) to (5-16), compounds (6-1) to (6-113) and compounds (7-1) to (7-57). In the compound of component C, $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

(5-1)
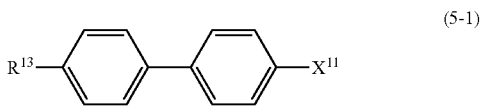

(5-2)
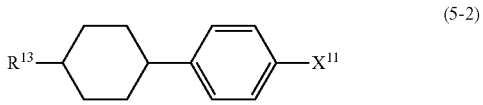

(5-3)
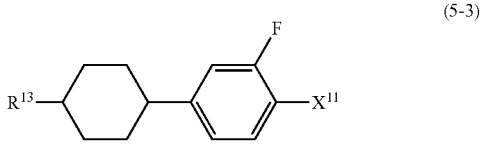

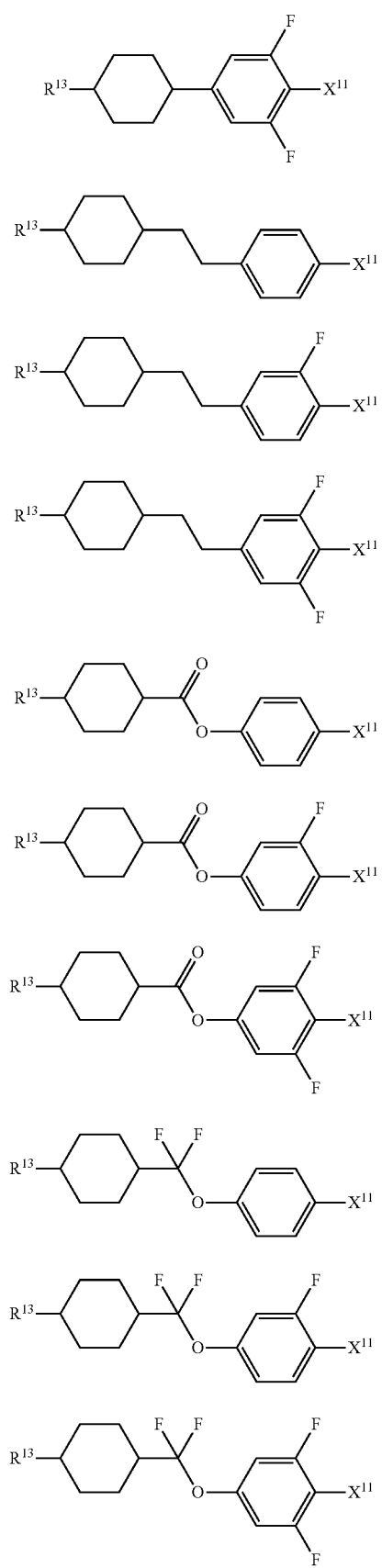
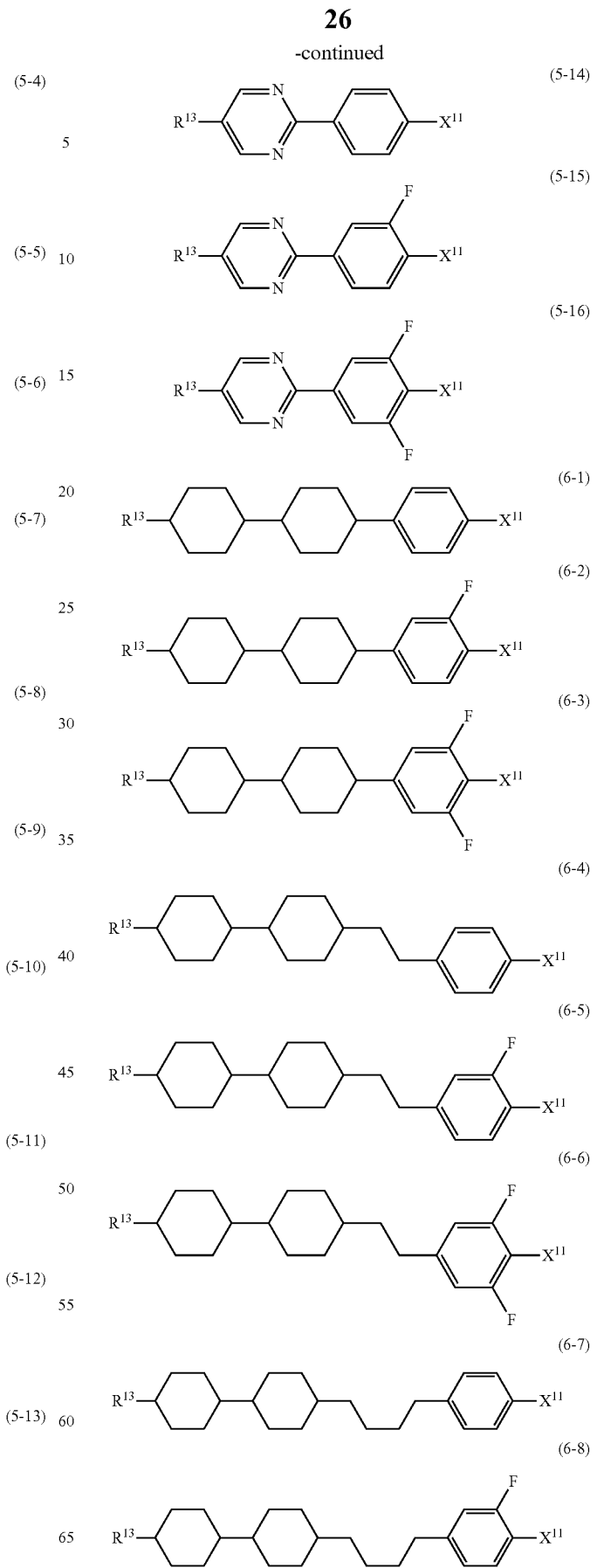

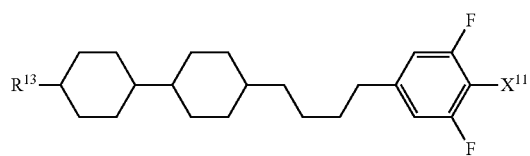 (6-9)
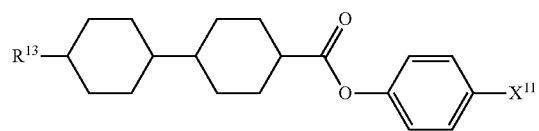 (6-10)
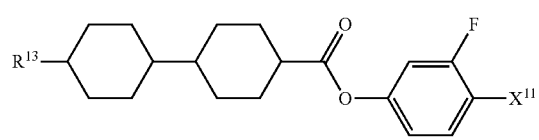 (6-11)
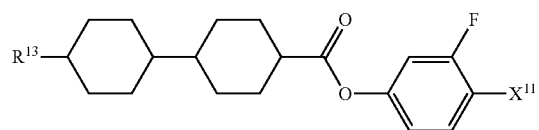 (6-12)
 (6-13)
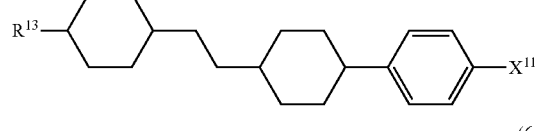 (6-14)
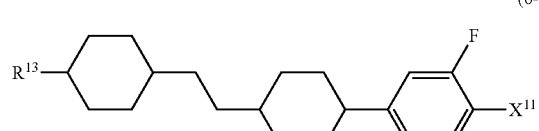 (6-15)
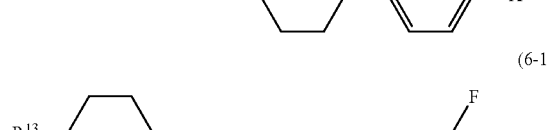 (6-16)
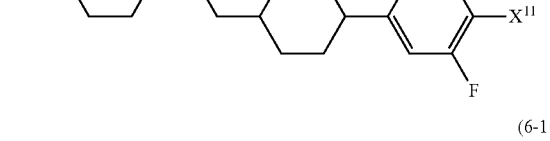 (6-17)
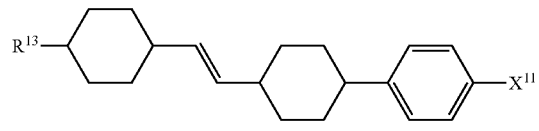 (6-18)
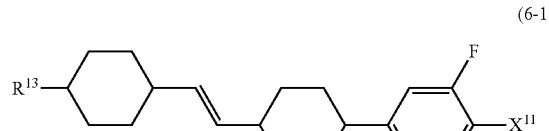 (6-19)
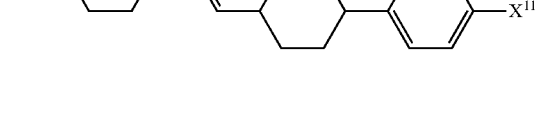 (6-20)
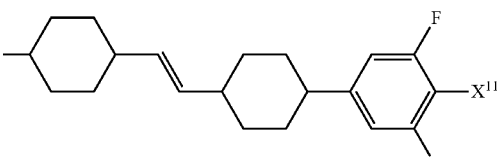 (6-21)
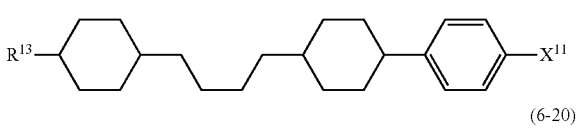 (6-22)
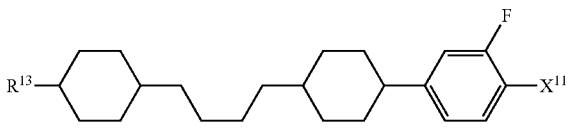 (6-23)
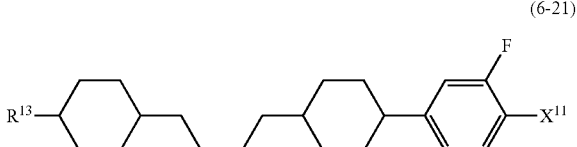 (6-24)
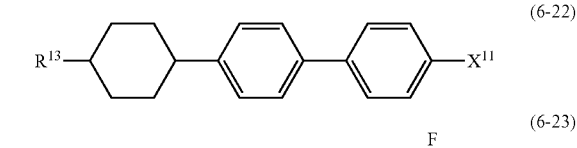 (6-25)
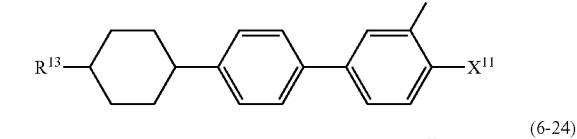 (6-26)
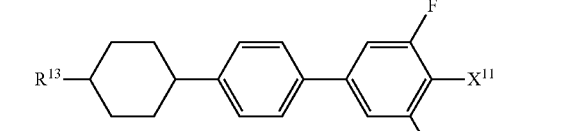 (6-27)
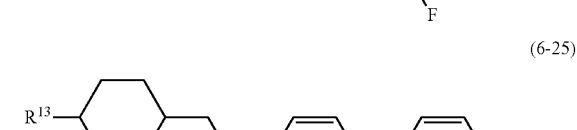
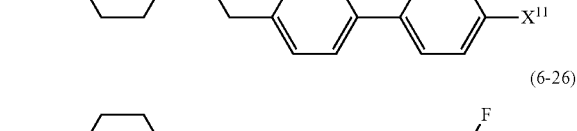
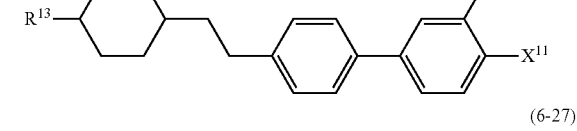

(6-28) 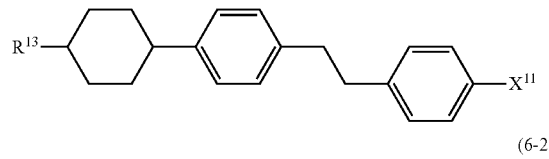
(6-29) 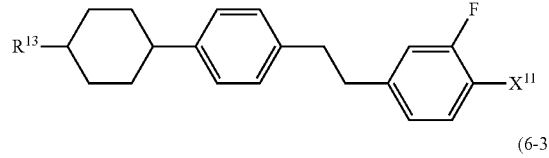
(6-30) 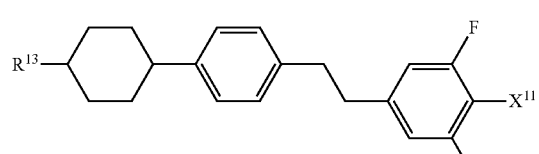
(6-31) 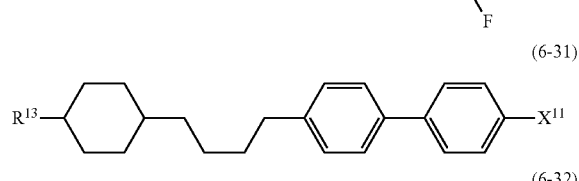
(6-32) 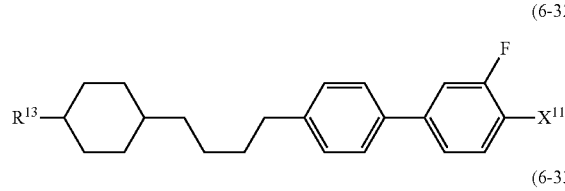
(6-33) 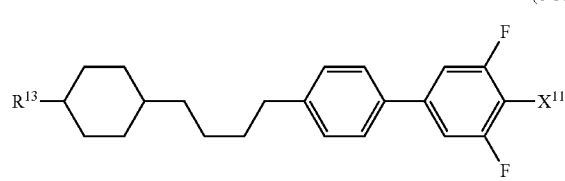
(6-34) 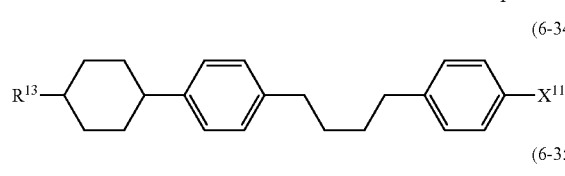
(6-35) 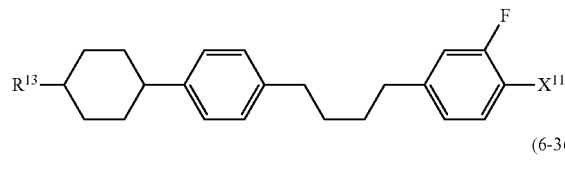
(6-36) 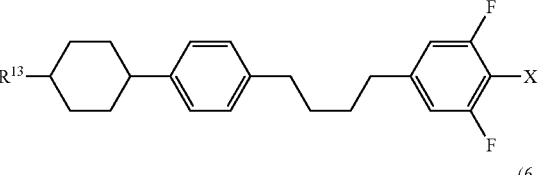
(6-37) 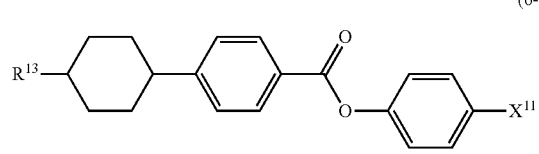
(6-38) 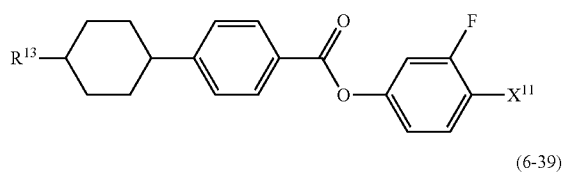
(6-39) 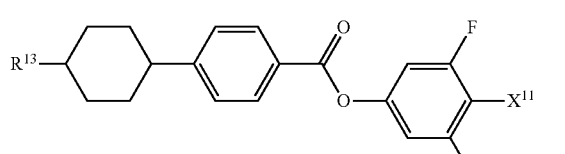
(6-40) 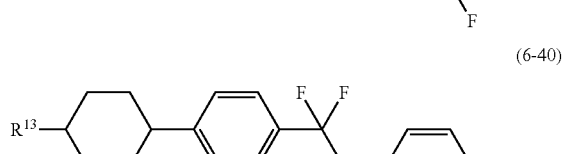
(6-41) 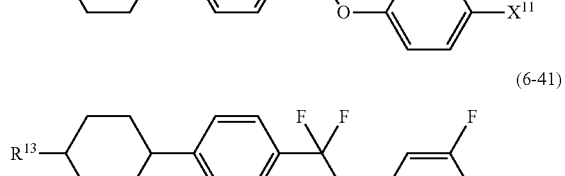
(6-42) 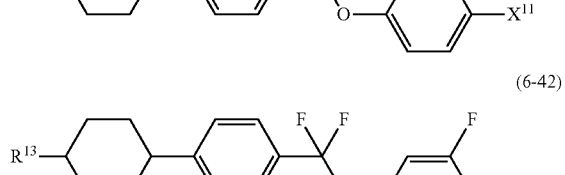
(6-43) 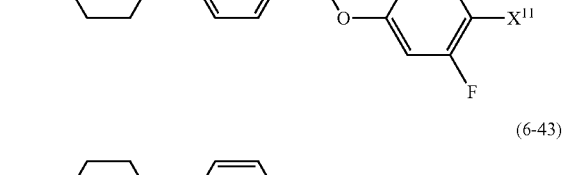
(6-44) 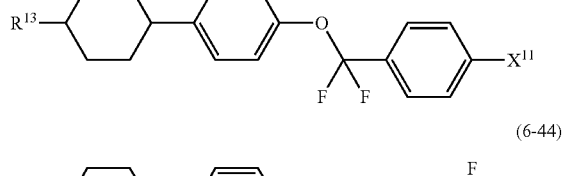
(6-45) 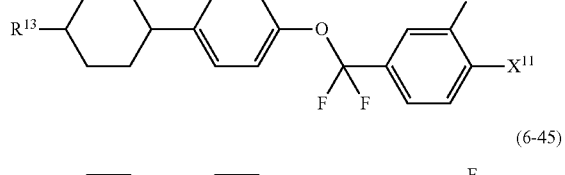
(6-46) 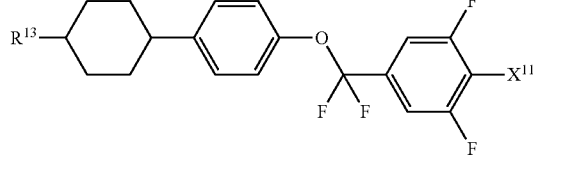

(6-47) 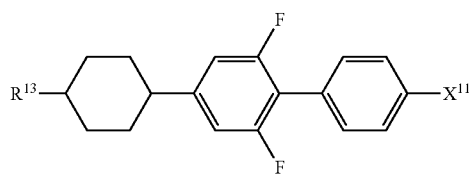
(6-48) 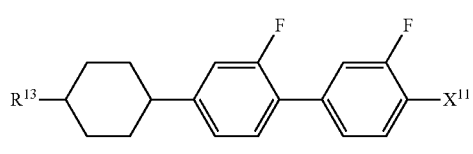
(6-49) 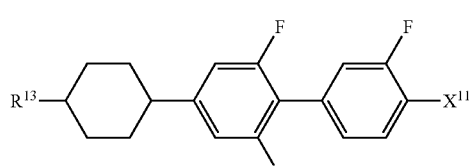
(6-50) 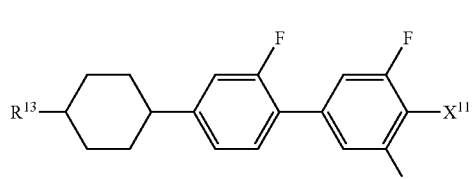
(6-51) 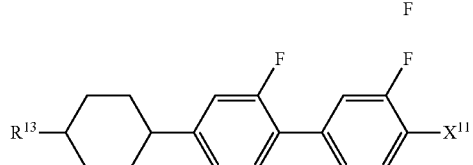
(6-52) 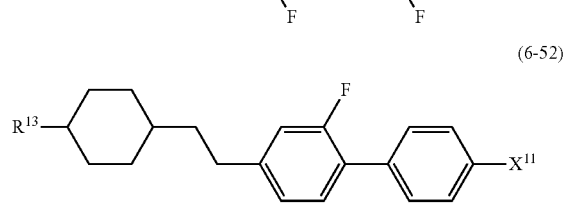
(6-53) 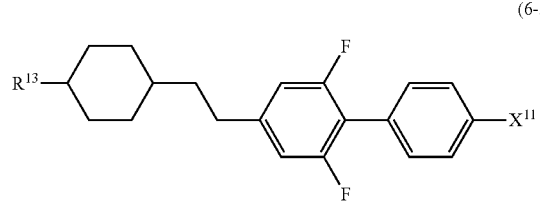
(6-54) 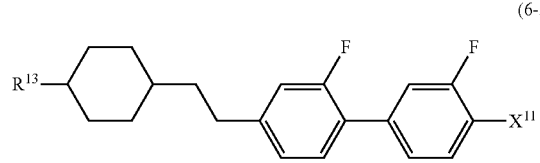
(6-55) 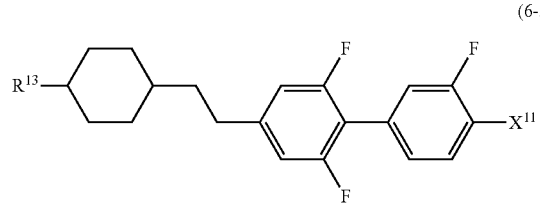
(6-56) 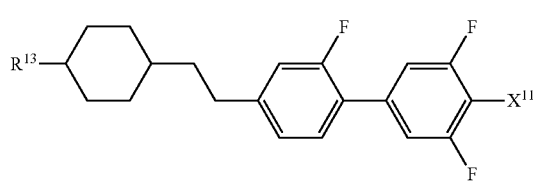
(6-57) 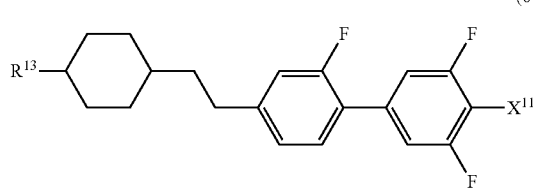
(6-58) 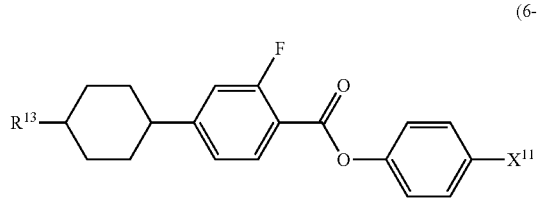
(6-59) 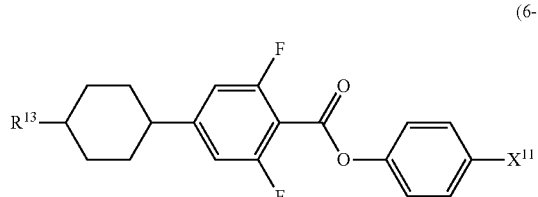
(6-60) 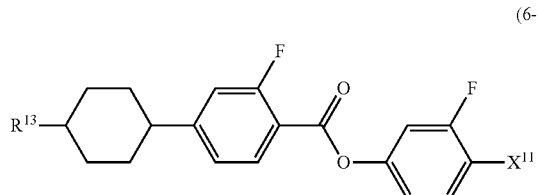
(6-60) 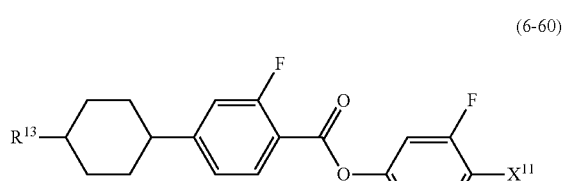
(6-61) 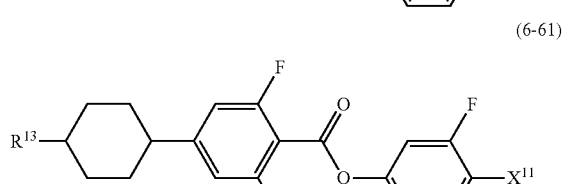
(6-61) 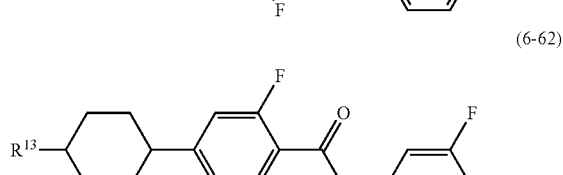
(6-62) 

(6-63) 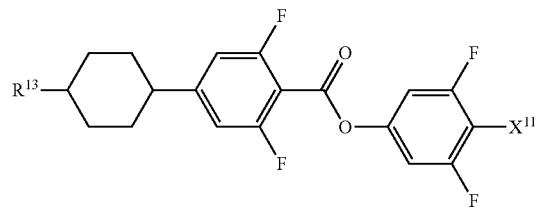
(6-64) 
(6-65) 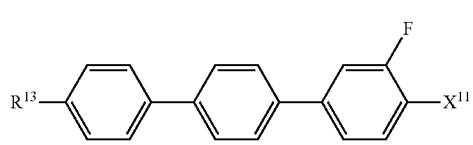
(6-66) 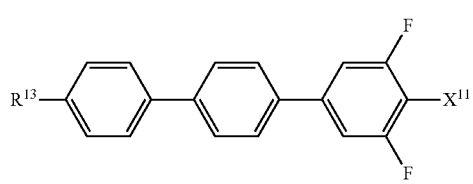
(6-67) 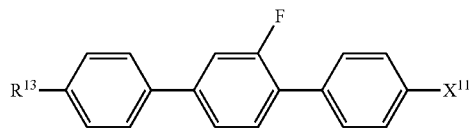
(6-68) 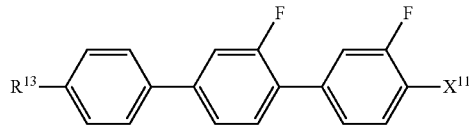
(6-69) 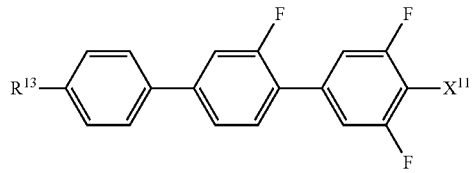
(6-70) 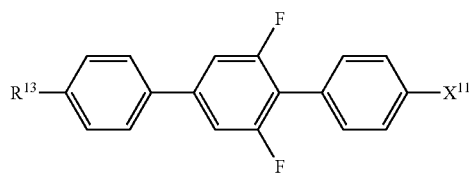
(6-71) 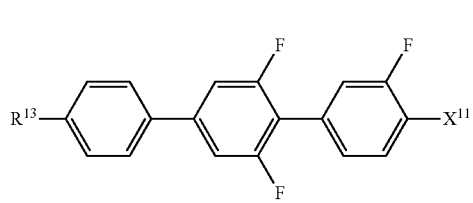
(6-72) 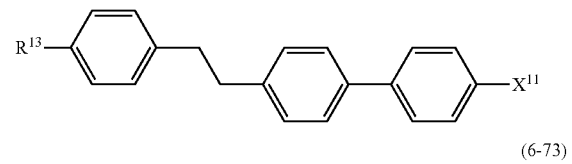
(6-73) 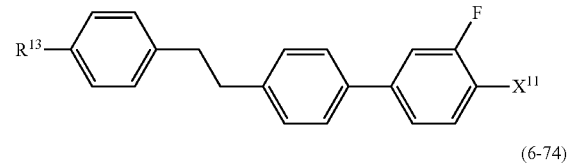
(6-74) 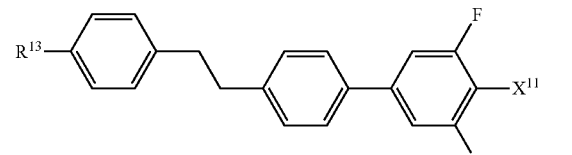
(6-75) 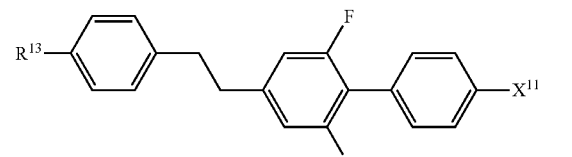
(6-76) 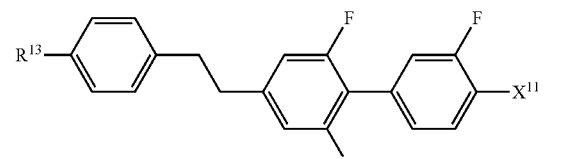
(6-77) 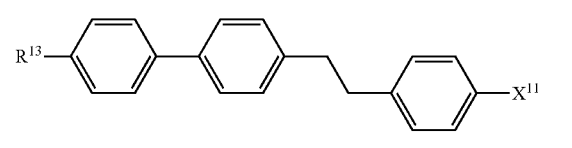
(6-78) 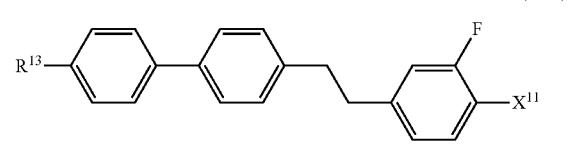
(6-79) 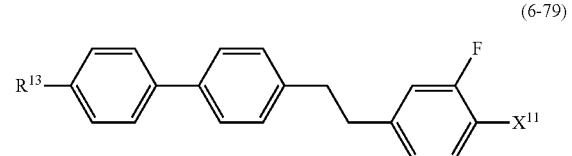
(6-80)

(6-81) 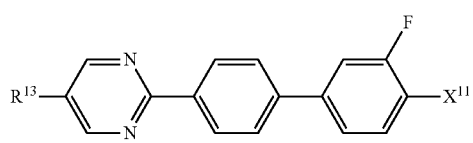
(6-82) 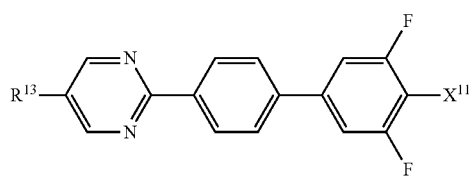
(6-83) 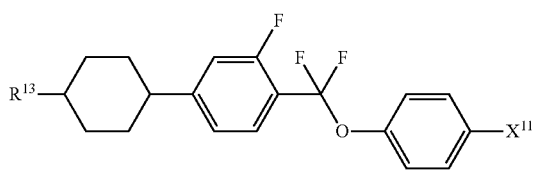
(6-84) 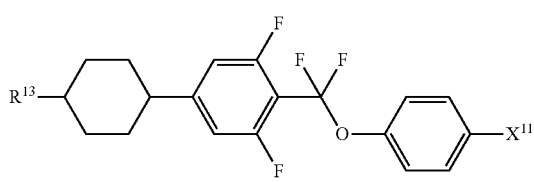
(6-85) 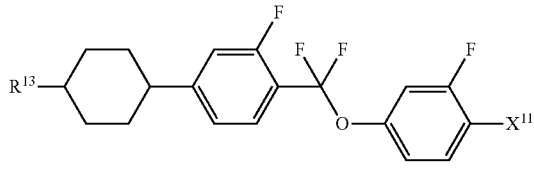
(6-86) 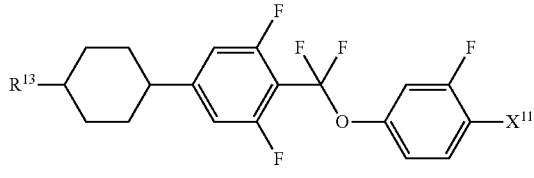
(6-87) 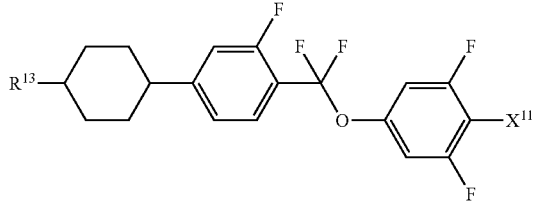
(6-88) 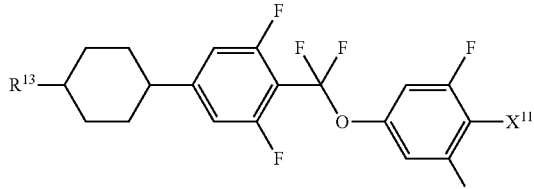
(6-89) 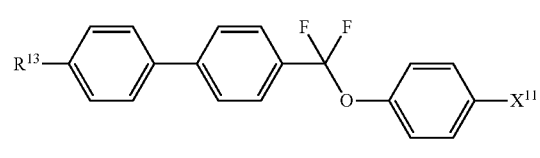
(6-90) 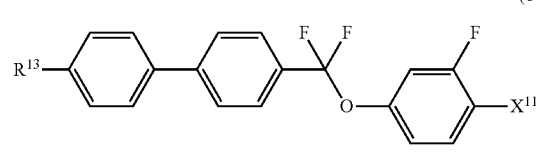
(6-91) 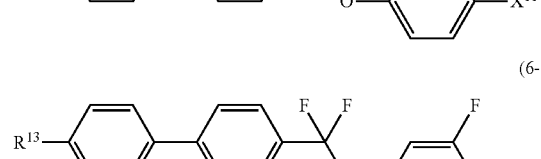
(6-92) 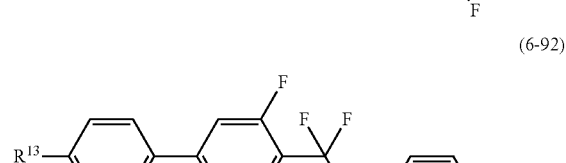
(6-93) 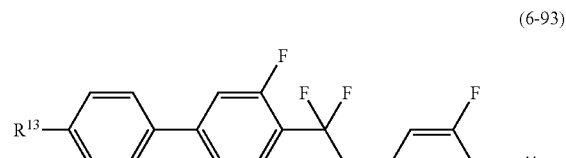
(6-94) 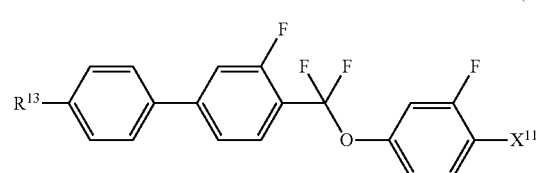
(6-95) 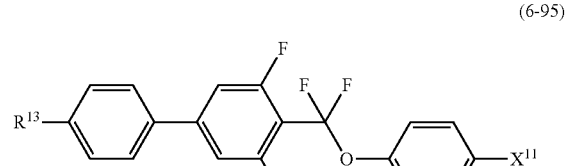
(6-96) 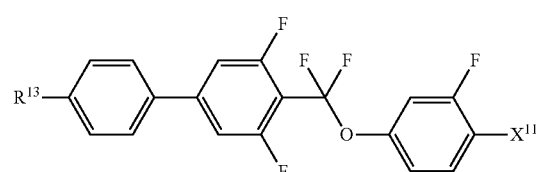

(6-97) 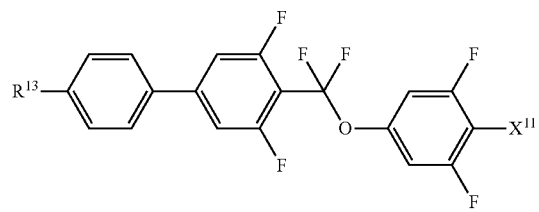
(6-98) 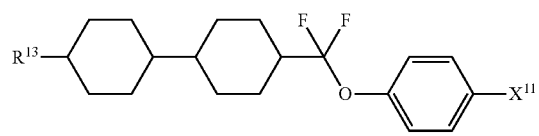
(6-99) 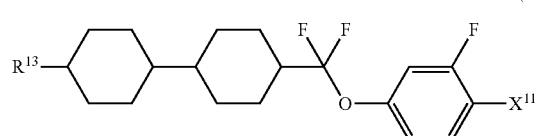
(6-100) 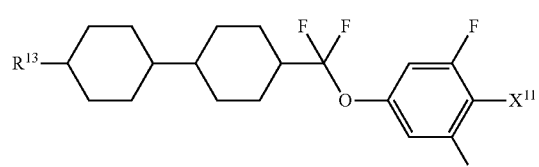
(6-101) 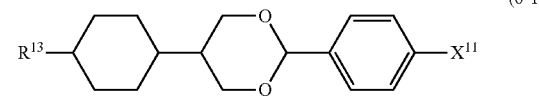
(6-102) 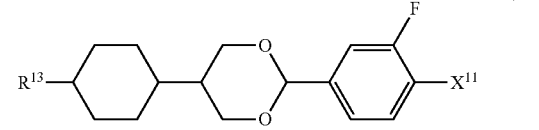
(6-103) 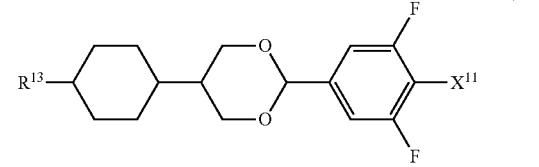
(6-104) 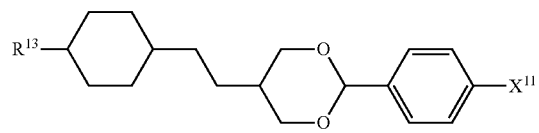
(6-105) 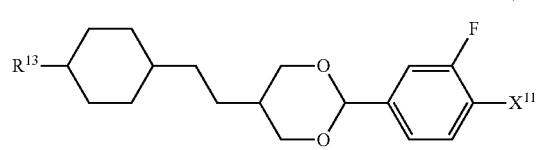
(6-106) 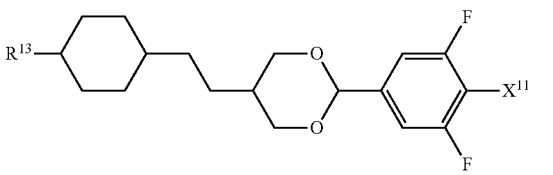
(6-107) 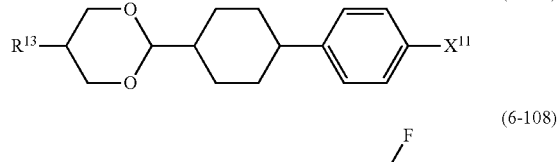
(6-108) 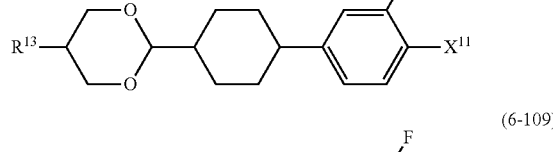
(6-109) 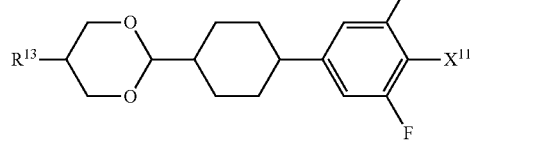
(6-110) 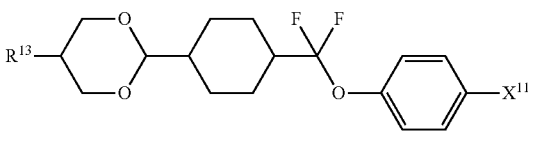
(6-111) 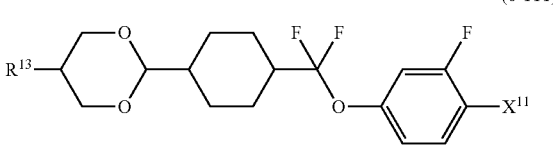
(6-112) 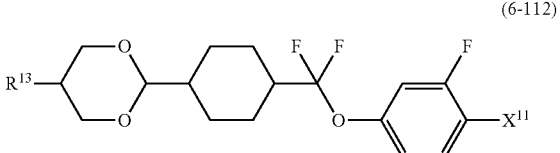
(6-113) 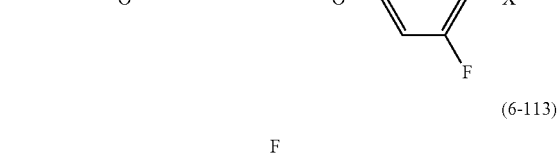
(7-1) 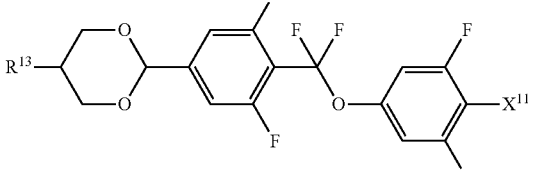

(7-2) 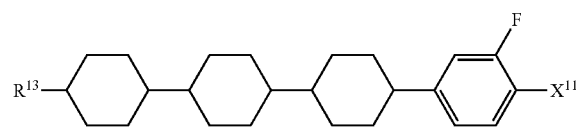
(7-3) 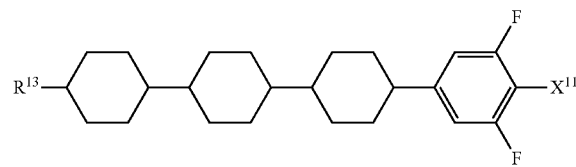
(7-4) 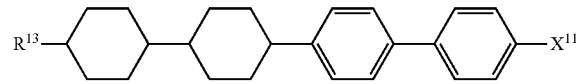
(7-5) 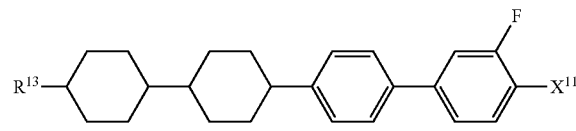
(7-6) 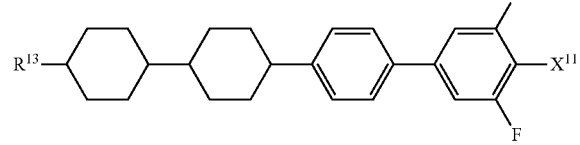
(7-7) 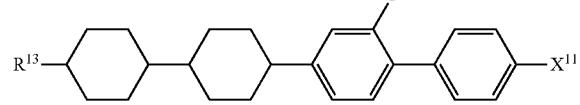
(7-8) 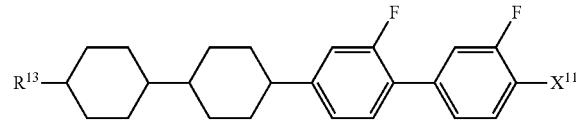
(7-9) 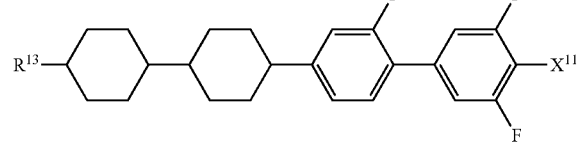
(7-10) 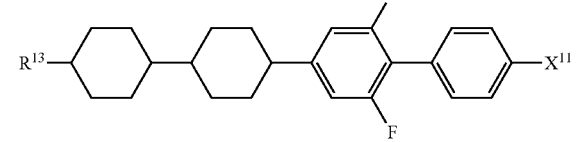
(7-11) 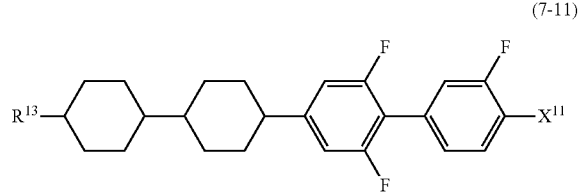
(7-12) 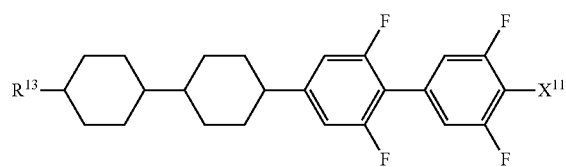
(7-13) 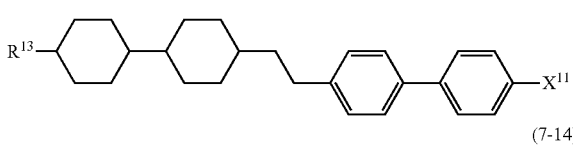
(7-14) 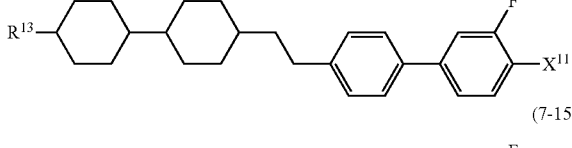
(7-15) 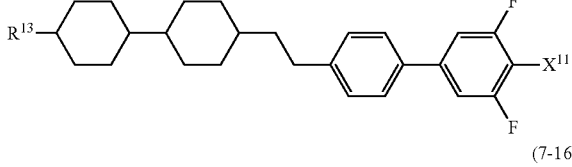
(7-16) 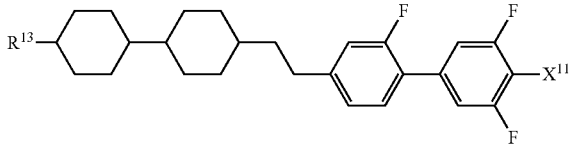
(7-17) 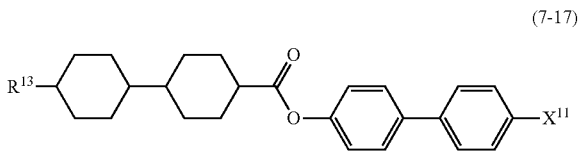
(7-18) 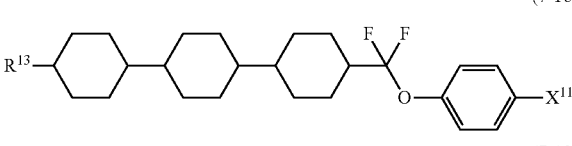
(7-19) 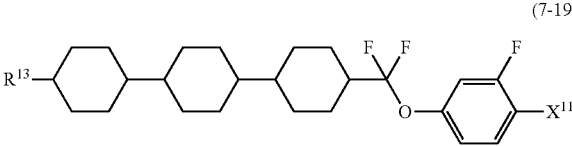
(7-20) 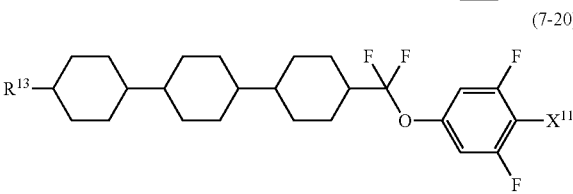

(7-21) 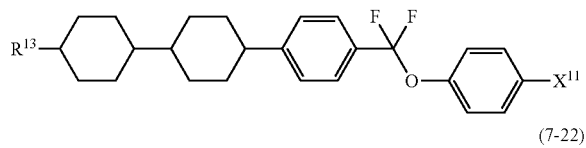
(7-22) 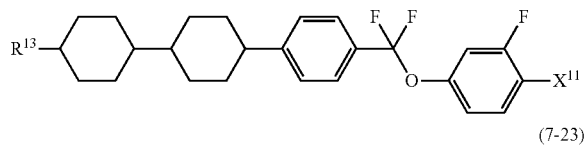
(7-23) 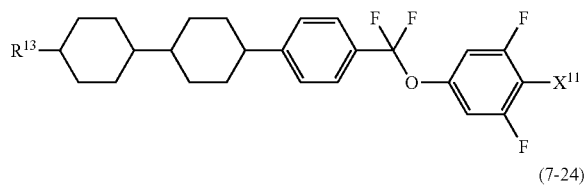
(7-24) 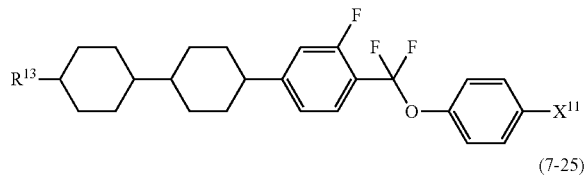
(7-25) 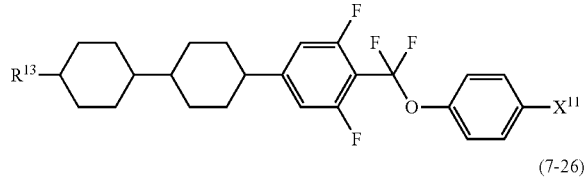
(7-26) 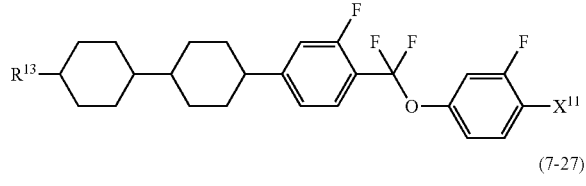
(7-27) 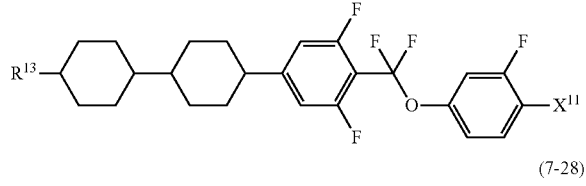
(7-28) 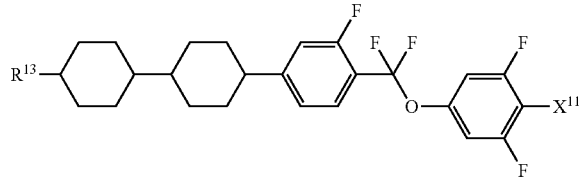
(7-29) 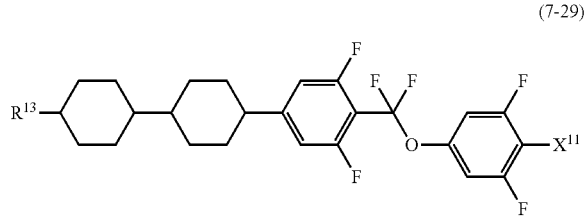
(7-30) 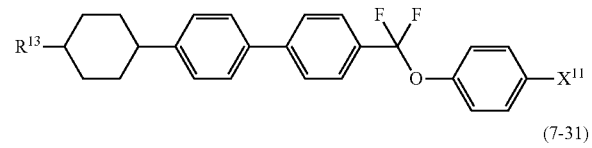
(7-31) 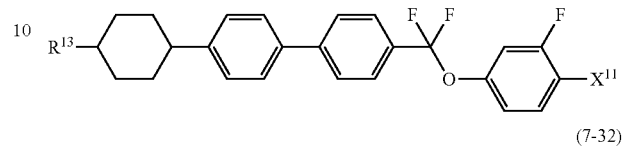
(7-32) 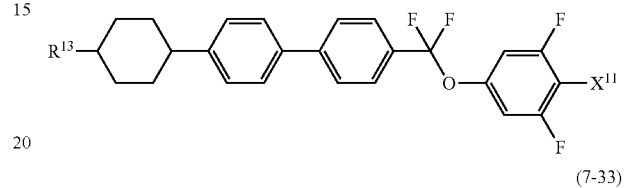
(7-33) 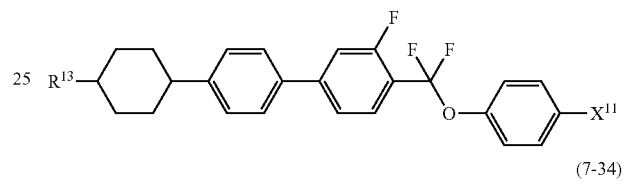
(7-34) 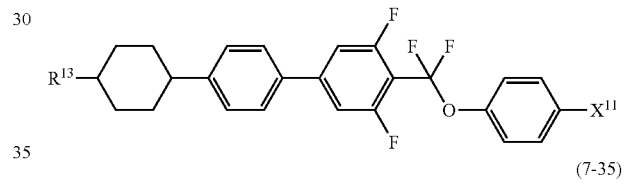
(7-35) 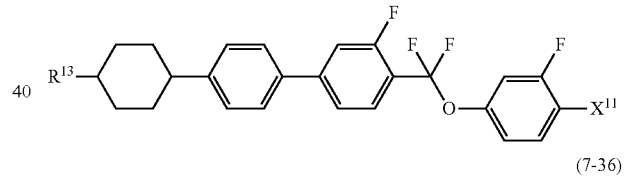
(7-36) 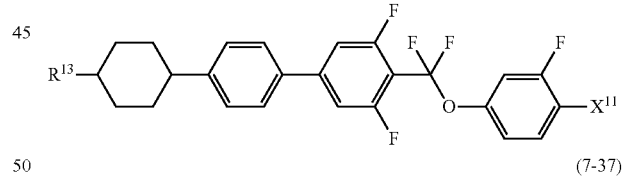
(7-37) 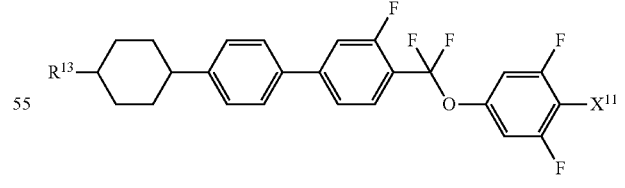
(7-38) 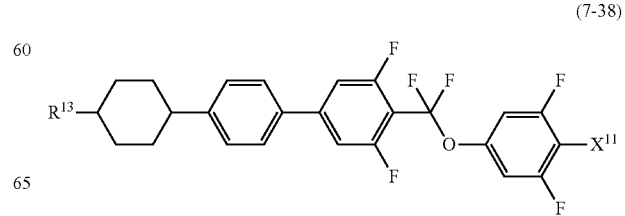

(7-39)
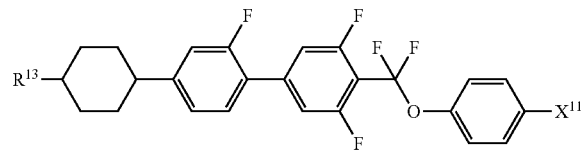
(7-40)
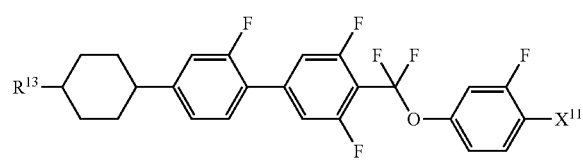
(7-41)
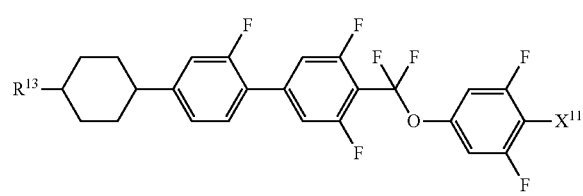
(7-42)
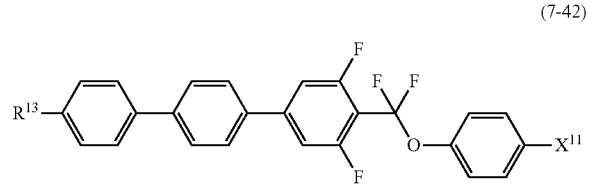
(7-43)
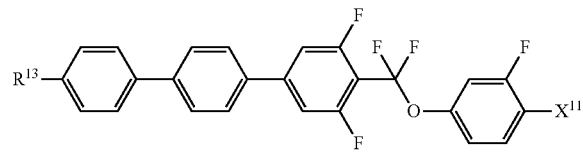
(7-44)
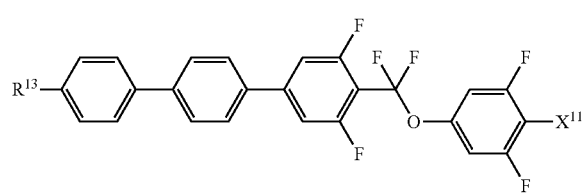
(7-45)
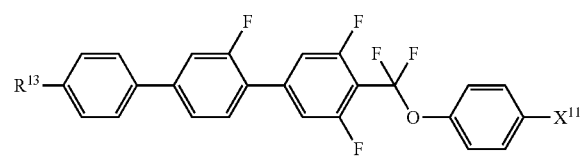
(7-46)
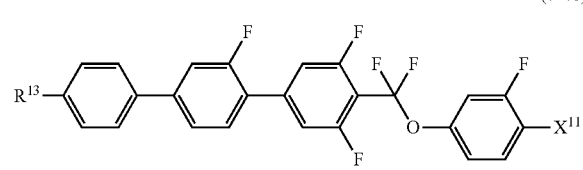
(7-47)
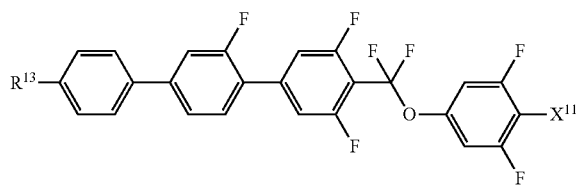
(7-48)
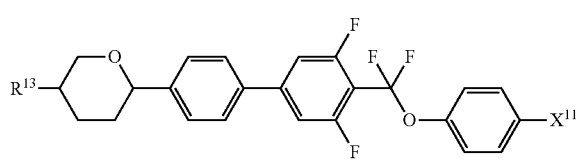
(7-49)
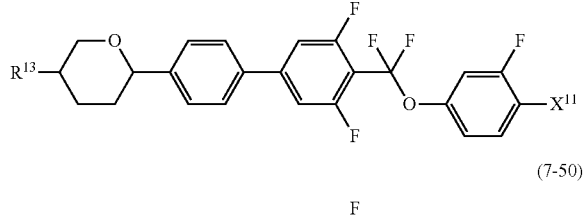
(7-50)
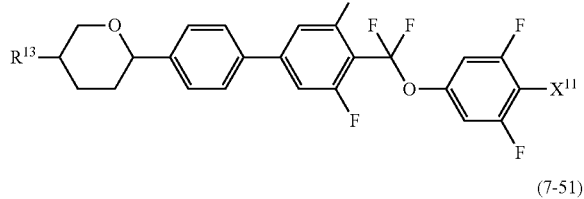
(7-51)
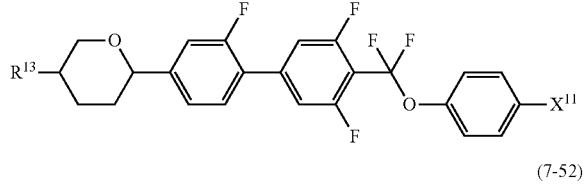
(7-52)
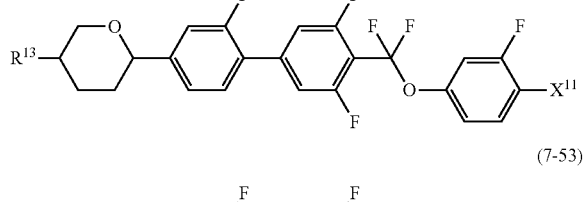
(7-53)
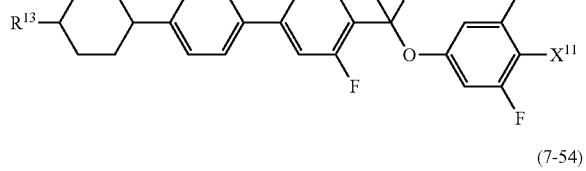
(7-54)
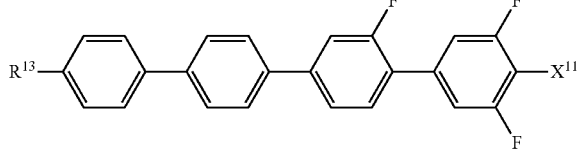

(7-55) 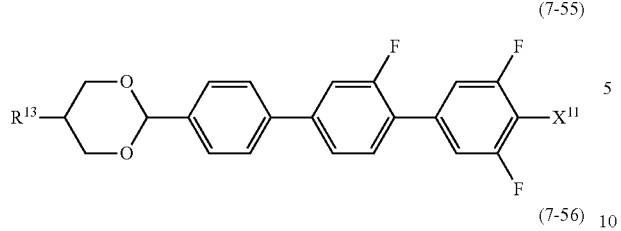

(7-56) 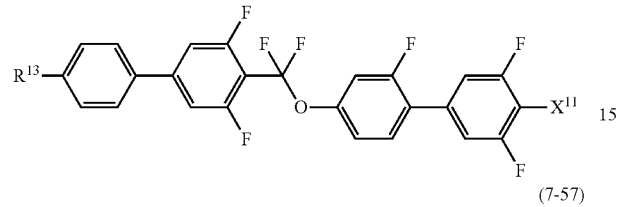

(7-57) 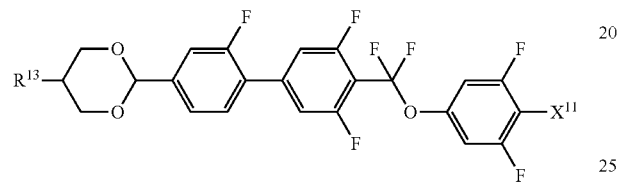

Component C has the positive dielectric anisotropy, and superb stability to heat, light and so forth, and therefore is used when a composition for a mode such as IPS, FFS and OCB is prepared. A content of component C is suitably in the range of approximately 1 to approximately 99% by weight, preferably in the range of approximately 10 to approximately 97% by weight, and further preferably in the range of approximately 40 to approximately 95% by weight, based on the weight of the liquid crystal composition. When component C is added to a composition having the negative dielectric anisotropy, the content of component C is preferably approximately 30% by weight or less based on the weight of the composition. When component C is added thereto, the elastic constant of the composition and a voltage-transmittance curve of the device can be adjusted.

Component D is compound (8) in which a right-terminal group is —C≡N or —C≡C—C≡N. Preferred examples of component D include compounds (8-1) to (8-64). In the compound of component D, $R^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine; and $X^{12}$ is —C≡N or —C≡C—C≡N.

(8-1) 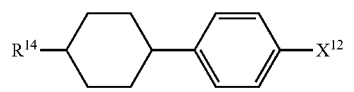

(8-2) 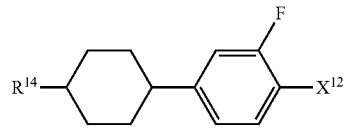

(8-3) 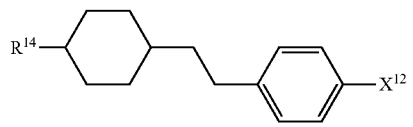

(8-4) 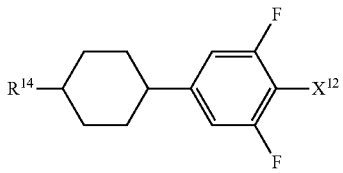

(8-5) 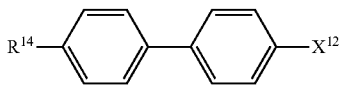

(8-6) 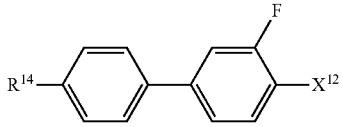

(8-7) 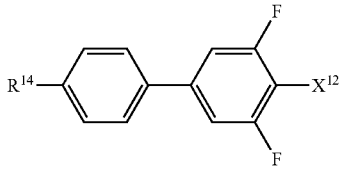

(8-8) 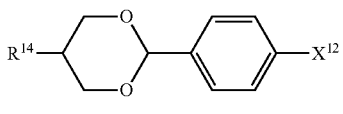

(8-9) 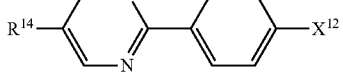

(8-10) 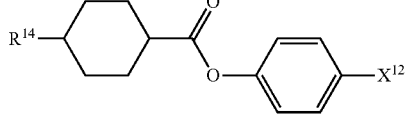

(8-11) 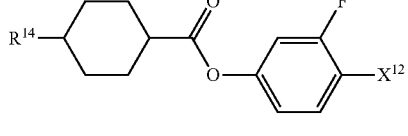

(8-12) 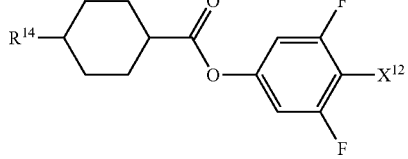

(8-13) 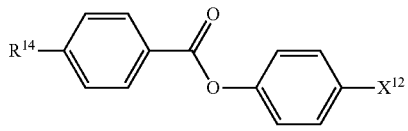

(8-14) 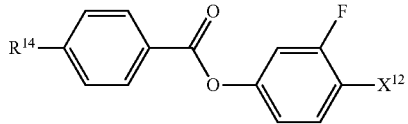

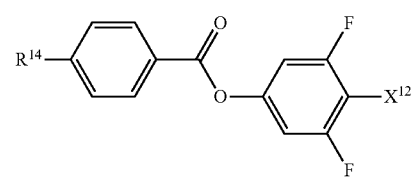 (8-15)
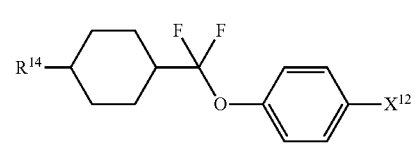 (8-16)
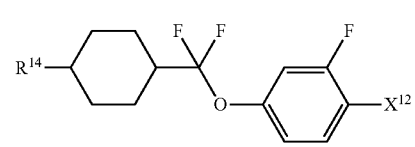 (8-17)
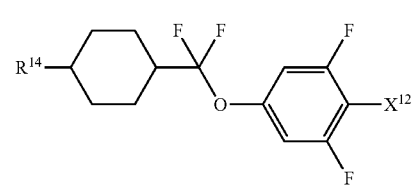 (8-18)
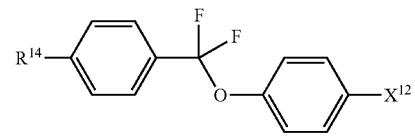 (8-19)
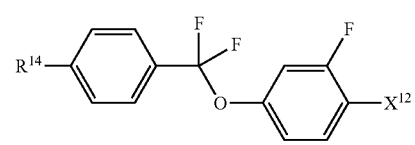 (8-20)
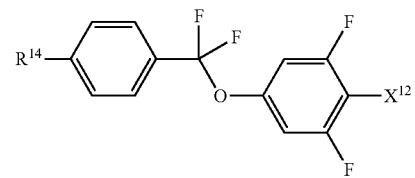 (8-21)
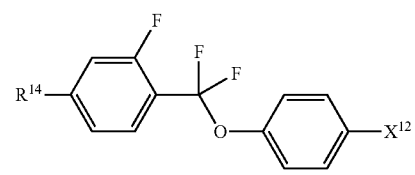 (8-22)
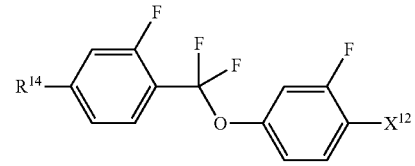 (8-23)
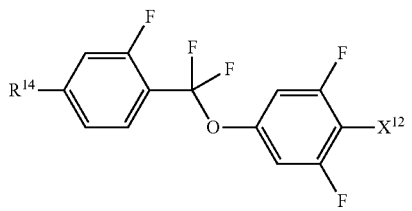 (8-24)
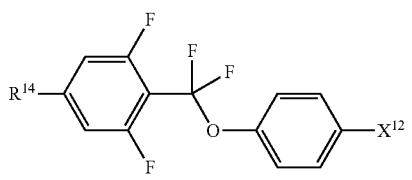 (8-25)
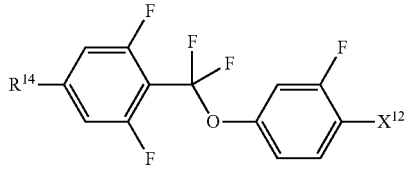 (8-26)
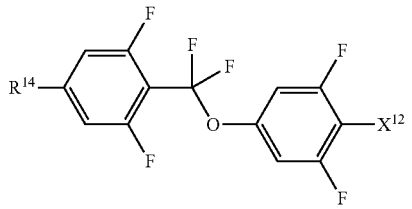 (8-27)
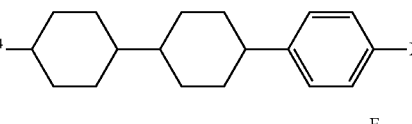 (8-28)
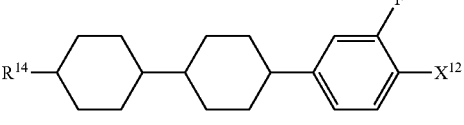 (8-29)
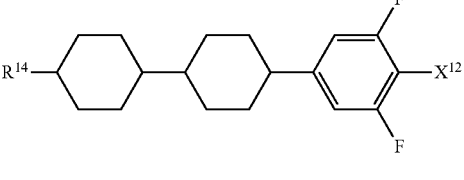 (8-30)
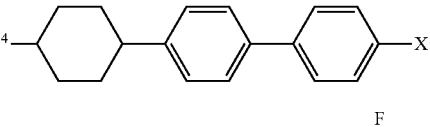 (8-31)
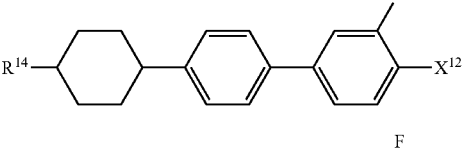 (8-32)
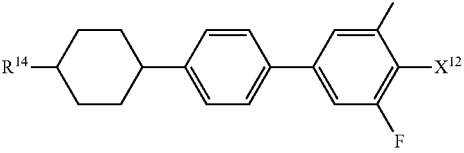 (8-33)

(8-34)
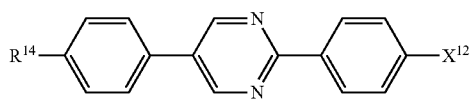
(8-35)
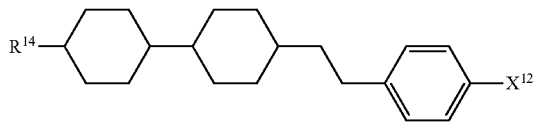
(8-36)
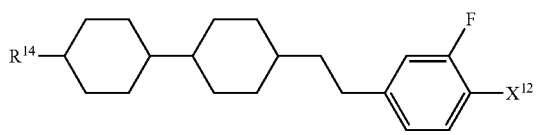
(8-37)
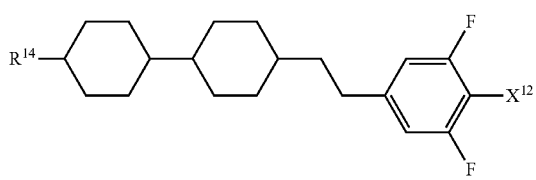
(8-38)
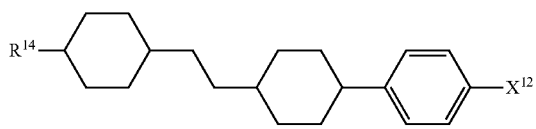
(8-39)
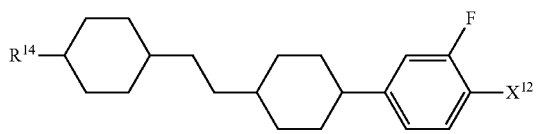
(8-40)
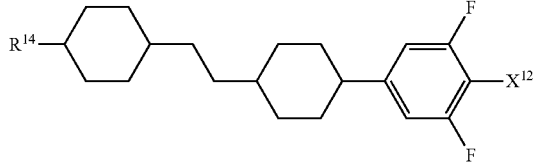
(8-41)
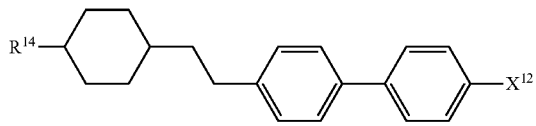
(8-42)
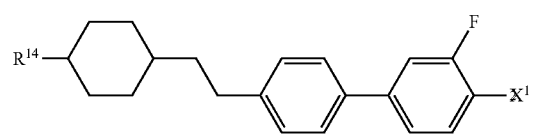
(8-43)
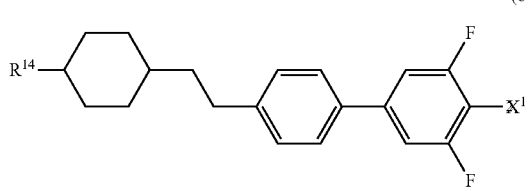
(8-44)
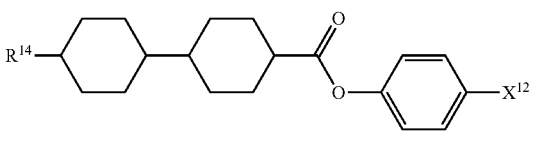
(8-45)
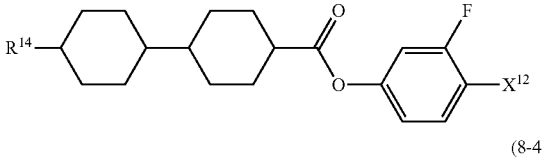
(8-46)
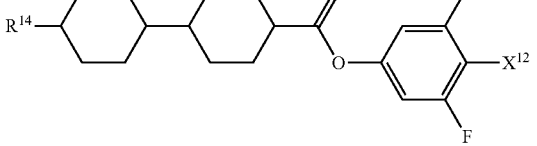
(8-47)
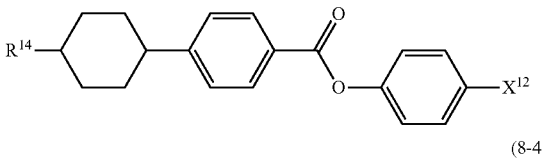
(8-48)
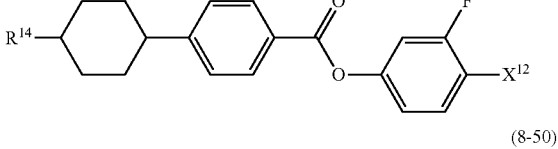
(8-49)
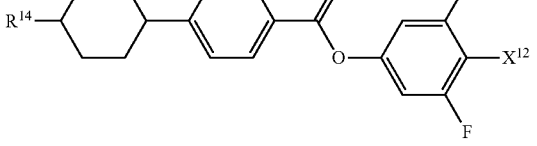
(8-50)
(8-51)
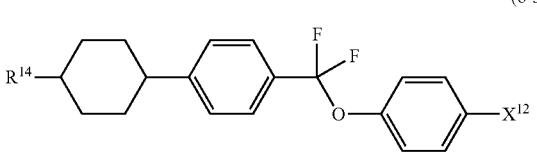
(8-52)

(8-53)
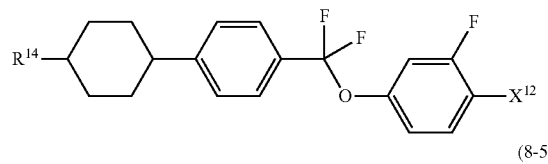

(8-54)
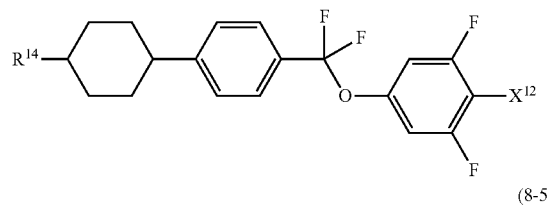

(8-55)
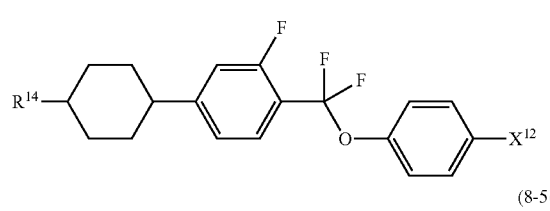

(8-56)
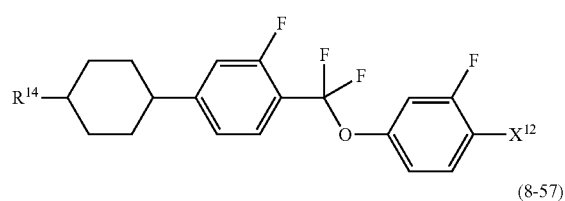

(8-57)

(8-58)
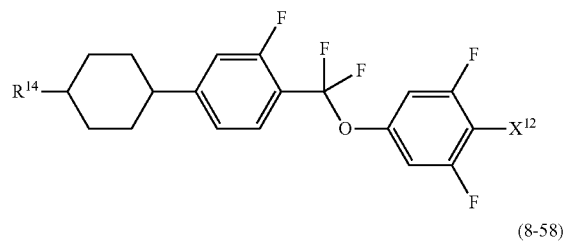

(8-59)

(8-60)
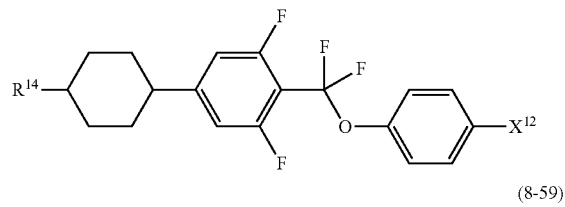

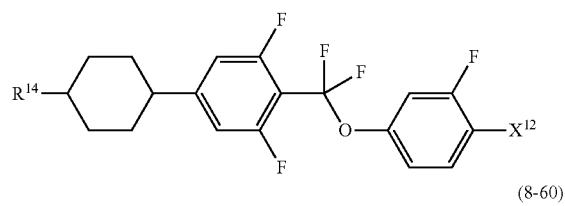

(8-61)
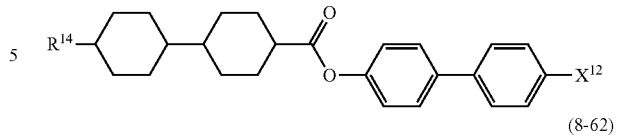

(8-62)
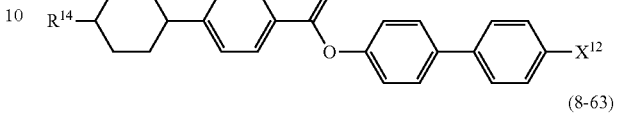

(8-63)
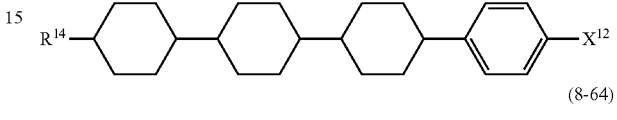

(8-64)
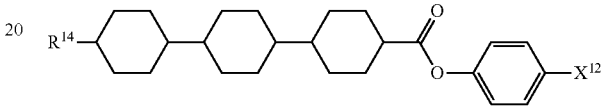

Component D has the positive dielectric anisotropy and a value thereof is large, and therefore is mainly used when a composition for the mode such as the TN mode is prepared. The dielectric anisotropy of the composition can be increased by adding component D thereto. Component D is effective in extending the temperature range of the liquid crystal phase, and adjusting the viscosity or adjusting the optical anisotropy. Component D is also useful for adjustment of the voltage-transmittance curve of the device.

When a composition for the TN mode or the like is prepared, a content of component D is suitably in the range of approximately 1 to approximately 99% by weight, preferably in the range of approximately 10 to approximately 97% by weight, and further preferably in the range of approximately 40 to approximately 95% by weight, based on the weight of the liquid crystal composition. When component D is added to a composition having the negative dielectric anisotropy, the content of component D is preferably approximately 30% by weight or less based on the weight of the composition. When component D is added thereto, the elastic constant of the composition and the voltage-transmittance curve of the device can be adjusted.

The liquid crystal composition satisfying at least one of characteristics such as the high maximum temperature, the low minimum temperature, the small viscosity, the suitable optical anisotropy, the large dielectric anisotropy, the suitable elastic constant and the large specific resistance can be prepared by suitably combining component B, C and D described above. A component different from component B, C and D may be added, when necessary. Example of such a component includes a compound having 2,3-difluoro-1,4-phenylene. The compound has the negative dielectric anisotropy. When such a compound is added to a composition having the positive dielectric anisotropy, the elastic constant of the composition and the voltage-transmittance curve of the device can be adjusted.

When compound (1) is added to a mixture of such components, a stable liquid crystal composition to light can be prepared. Preparation of the liquid crystal composition is performed by a method of dissolving required components at a temperature higher than room temperature, or the like. According to an application, an additive may be added to the composition. Specific examples of the additive include the polymerizable compound, the polymerization initiator, the polymerization inhibitor, the optically active compound, the antioxidant, the ultraviolet light absorber, the light stabilizer, the heat stabilizer and the antifoaming agent. Such additives are well known to those skilled in the art, and described in literature.

The polymerizable compound is added for the purpose of forming the polymer in the composition. The polymerizable compound is polymerized by irradiation with ultraviolet light while voltage is applied between electrodes, thus the polymer is formed in the liquid crystal composition. A suitable pretilt is obtained by the method, and therefore the liquid crystal display device in which the response time is shortened and the image persistence is improved is obtained.

Preferred examples of the polymerizable compound include acrylate, methacrylate, a vinyl compound, a vinyloxy compound, propenyl ether, an epoxy compound (oxirane, oxetane) and vinyl ketone. Further preferred examples include a compound having at least one acryloyloxy, and a compound having at least one methacryloyloxy. Further preferred examples include a compound having both acryloyloxy and methacryloyloxy.

Further preferred examples include compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

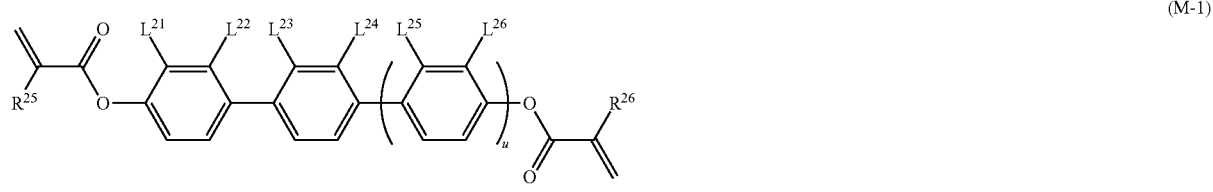

(M-1)

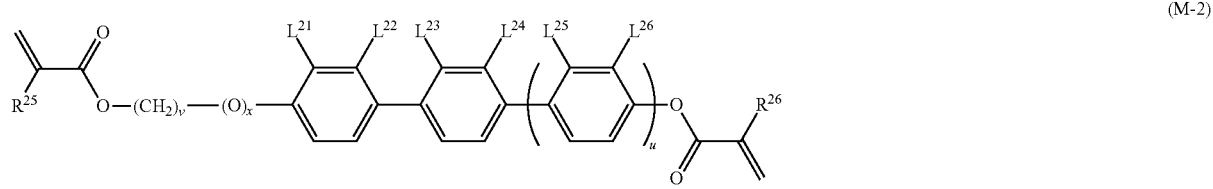

(M-2)

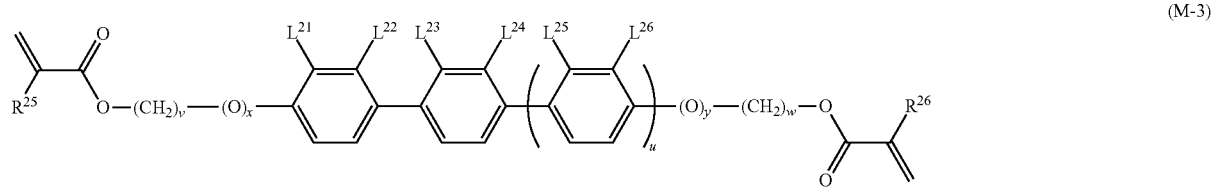

(M-3)

(M-4) (M-5)

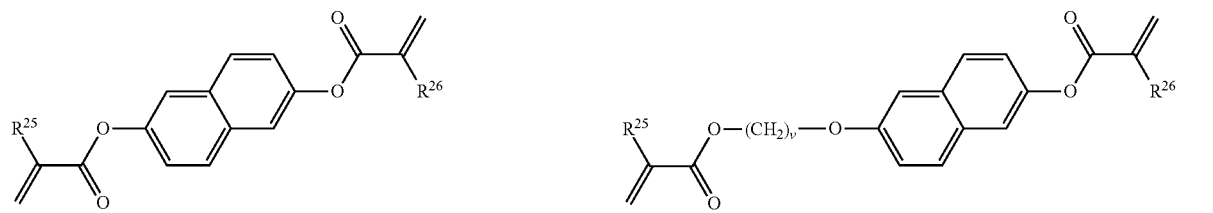

(M-6)

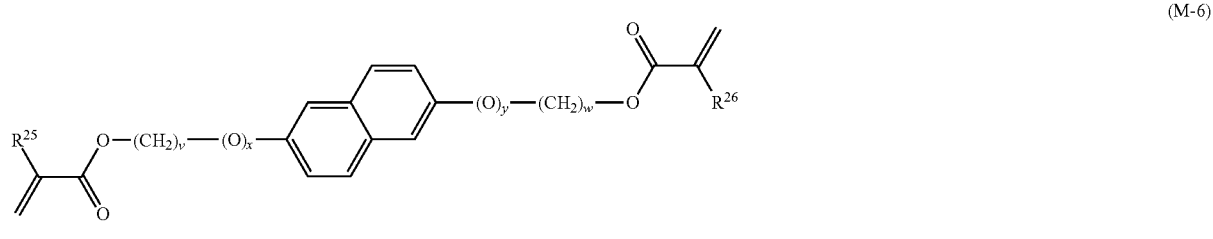

(M-7) (M-8)

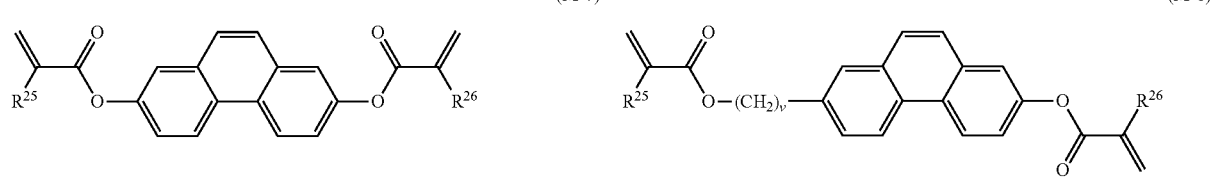

-continued

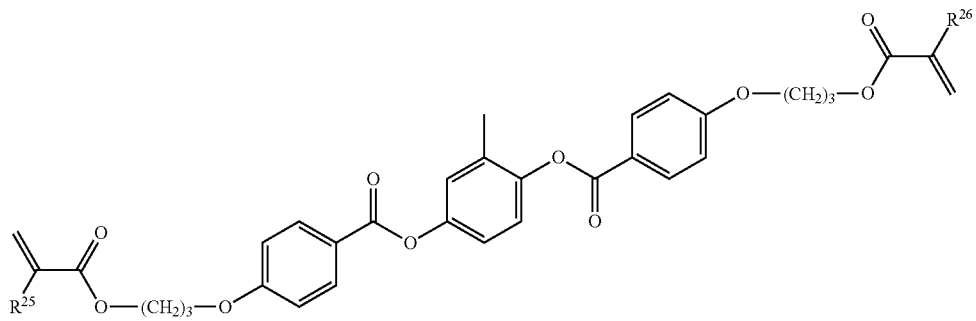
(M-9)

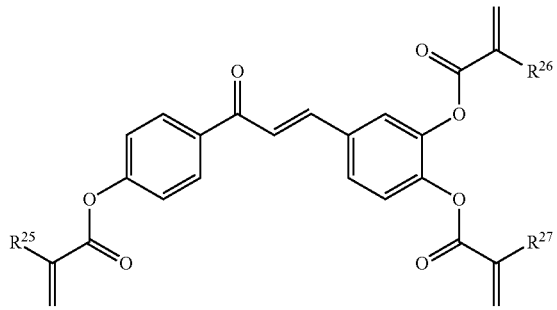
(M-10)

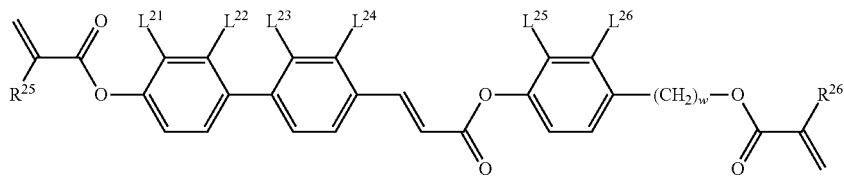
(M-11)

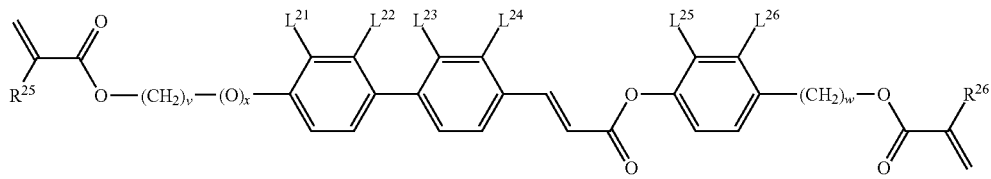
(M-12)

The polymerizable compound can be rapidly polymerized by adding the polymerizable initiator. An amount of a remaining polymerizable compound can be decreased by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/mercaptobenzimidazole mixture, 1-(4-isopropylphenyl)-2-hydroxy-2-methylpropane-1-one, benzyldimethylketal, 2-methyl-1-[4-(methylthio)phenyl]-2-morpholinopropane-1-one, a 2,4-diethylxanthone/methyl p-dimethylaminobenzoate mixture and a benzophenone/methyltriethanolamine mixture.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause a poor display such as the image persistence in the device. In order to prevent such an event, photopolymerization may be performed with no addition of the polymerization initiator. A preferred wavelength of light to be irradiated is in the range of approximately 150 nanometers to approximately 500 nanometers. A further preferred wavelength is in the range of approximately 250 nanometers to approximately 400 nanometers, and a most preferable wavelength is in the range of approximately 300 nanometers to approximately 400 nanometers.

Upon storing the polymerizable compound, the polymerization inhibitor may be added thereto. The polymerizable compound is ordinarily added to the composition without removing the polymerization inhibitor. Examples of the polymerization inhibitor include hydroquinone, a hydroquinone derivative such as methylhydroquinone, 4-tert-butylcatechol, 4-methoxyphenol and phenothiazine.

The optically active compound is effective in inducing a helical structure in liquid crystal molecules to give a required twist angle, thereby being effective in preventing a reverse twist. A helical pitch can be adjusted by adding the optically active compound thereto. Two or more optically active compounds may be added for the purpose of adjusting temperature dependence of the helical pitch. Preferred examples of the optically active compound include compounds (Op-1) to (Op-18) below. In compound (Op-18), ring J is 1,4-cyclohexylene or 1,4-phenylene, and $R^{28}$ is alkyl having 1 to 10 carbons.
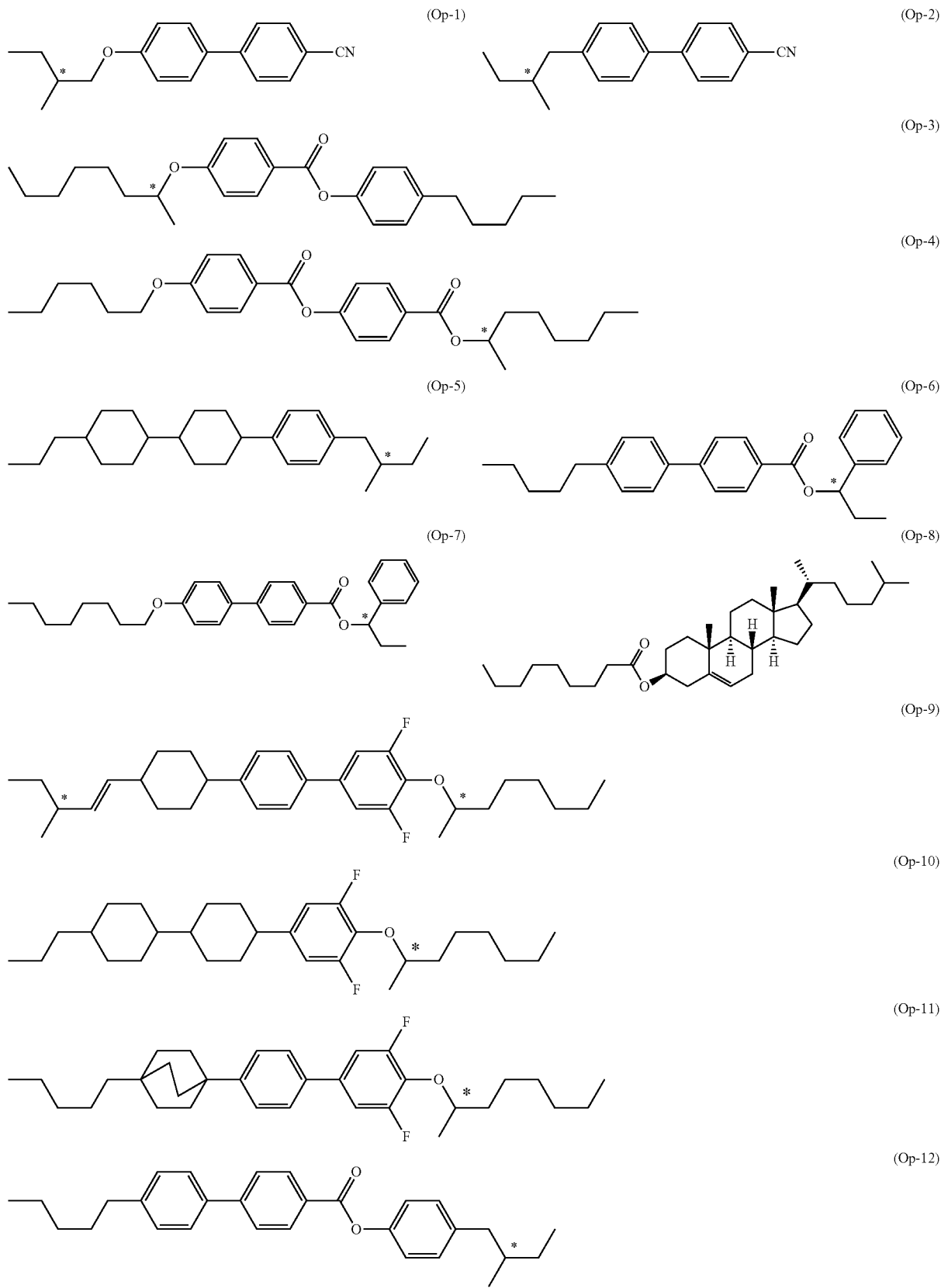

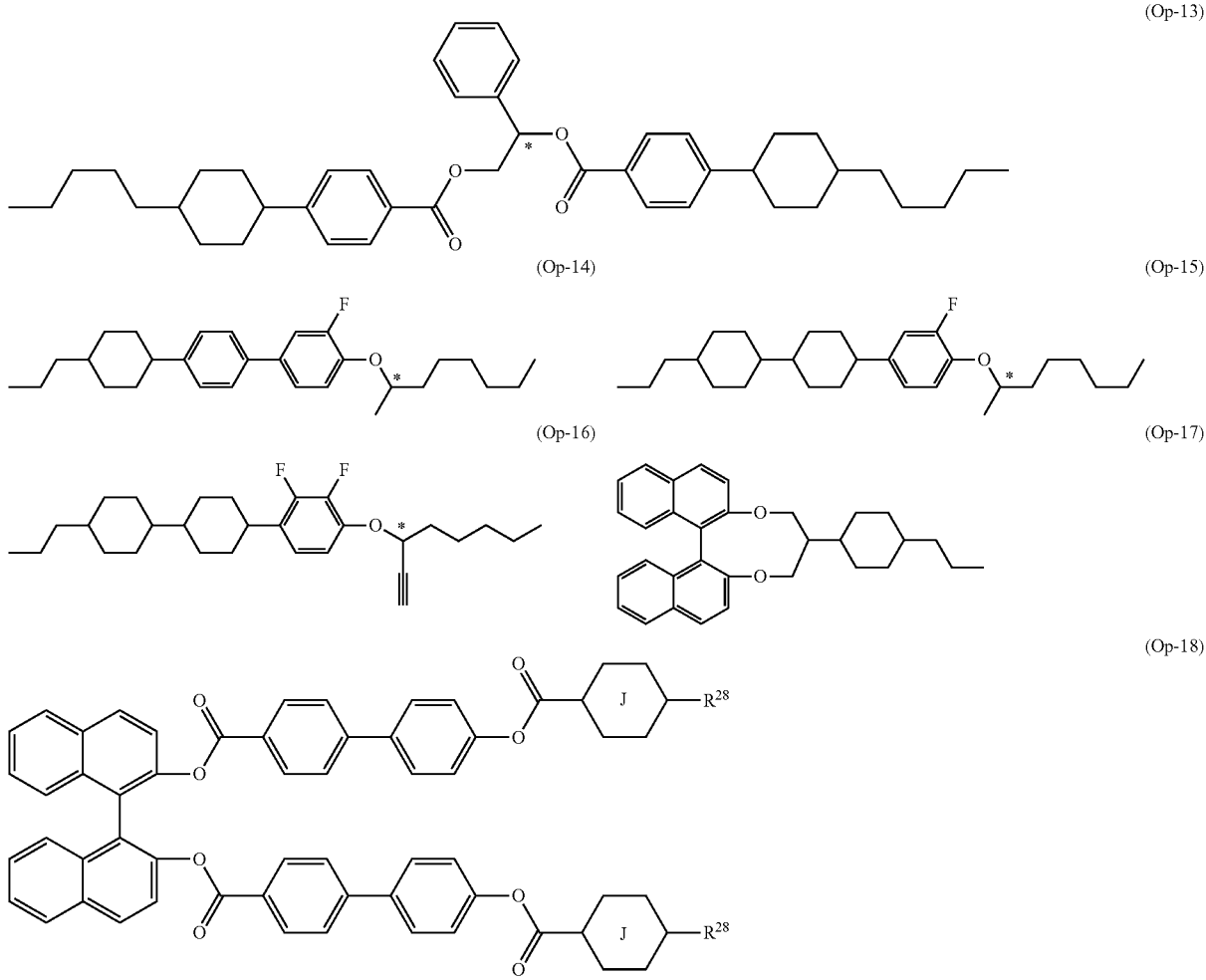

The antioxidant is effective for maintaining the large voltage holding ratio. Preferred examples of the antioxidant include compounds (AO-1) and (AO-2) below; IRGANOX 415, IRGANOX 565, IRGANOX 1010, IRGANOX 1035, IRGANOX 3114 and IRGANOX 1098 (trade names: BASF SE). The ultraviolet light absorber is effective in preventing a decrease of the maximum temperature. Preferred examples of the ultraviolet light absorbent include a benzophenone derivative, a benzoate derivative and a triazole derivative. Specific examples includes compounds (AO-3) and (AO-4) below; TINUVIN329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Preferred examples of the light stabilizer include compounds (AO-5) and (AO-6) below; and TINUVIN 144, TINUVIN 765 and TINUVIN 770DF (trade names: BASF SE). Further preferred light stabilizer is compound (1). The heat stabilizer is also effective for maintaining the large voltage holding ratio, and preferred examples include IRGAFOS 168 (trade name: BASF SE). The antifoaming agent is effective in preventing foam formation. Preferred examples of the antifoaming agent include dimethyl silicone oil and methylphenyl silicone oil.

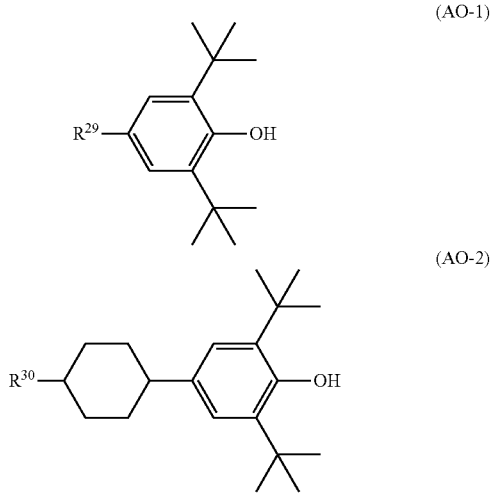

-continued

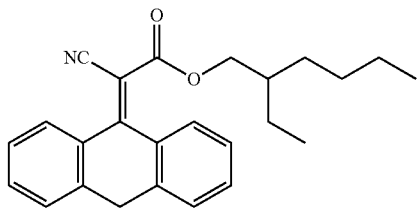
(AO-3)

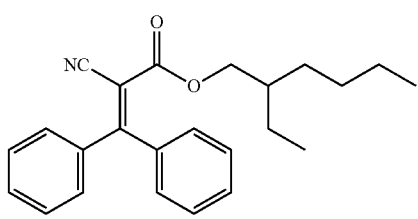
(AO-4)

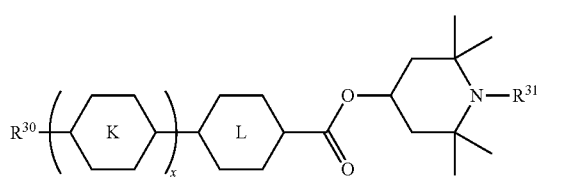
(AO-5)

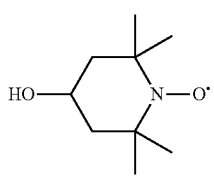
(AO-6)

In compound (AO-1), $R^{29}$ is alkyl having 1 to 20 carbons, alkoxy having 1 to 20 carbons, —COOR$^{32}$ or —CH$_2$CH$_2$COOR$^{32}$, in which $R^{32}$ is alkyl having 1 to 20 carbons. In compounds (AO-2) and (AO-5), $R^{30}$ is alkyl having 1 to 20 carbons. In compound (AO-5), $R^{31}$ is hydrogen, methyl or O. (oxygen radical), and ring K and ring L are 1,4-cyclohexylene or 1,4-phenylene, and x is 0, 1 or 2.

4. Liquid Crystal Display Device

The liquid crystal composition can be used for the liquid crystal display device having an operating mode such as the PC mode, the TN mode, the STN mode, the OCB mode and the PSA mode, and driven by an active matrix (AM mode). The composition can also be used for the liquid crystal display device having the operating mode such as the PC mode, the TN mode, the STN mode, the OCB mode, the VA mode and the IPS mode, and driven by a passive matrix (PM) mode. The AM mode and the PM mode devices can be applied to any of a reflective type, a transmissive type and transflective type.

The composition can also be used for a nematic curvilinear aligned phase (NCAP) device prepared by microencapsulating a nematic liquid crystal, a polymer dispersed liquid crystal display device (PDLCD) and a polymer network liquid crystal display device (PNLCD), in which a three-dimensional network polymer is formed in the liquid crystal. When an amount of adding the polymerizable compound is in the range approximately 0.1 to approximately 2% by weight based on the weight of the liquid crystal composition, the liquid crystal display device having the PSA mode can be prepared. The device having the PSA mode can be driven by the driving mode such as an active matrix mode and a passive matrix mode. Such devices can be applied to any of the reflective type, the transmissive type and the transflective type. The device having the polymer dispersed mode can also be prepared by increasing an amount of adding the polymerizable compound.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. The invention is not limited by the Examples. The invention includes a mixture of a composition in Example 1 and a composition in Example 2. The invention also includes a mixture in which at least two compositions in Examples were mixed. A compound prepared was identified by a method such as an NMR analysis. Characteristics of the compound, the composition and a device were measured by methods described below.

1. Example of Compound (1)

Compound (1) was prepared according to procedures described in Synthesis Examples. Unless otherwise described, a reaction was performed under a nitrogen atmosphere. The compound prepared was identified by methods such as an NMR analysis. Characteristics of the compound were measured by methods as described below.

NMR Analysis

For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using CFCl$_3$ as an internal standard. In the explanation of a nuclear magnetic resonance spectrum, s, d, t, q, quin, sex and m stand for a singlet, a doublet, a triplet, a quartet, a quintet, a sextet and a multiplet, respectively, and br means being broad.

Gas Chromatographic Analysis

GC-2010 Gas Chromatograph made by Shimadzu Corporation was used for measurement. A capillary column DB-1 (length 60 m, bore 0.25 mm, film thickness 0.25 m) made by Agilent Technologies, Inc. was used. Helium was used as a carrier gas, and a flow rate was adjusted to 1 milliliter per minute. A temperature of a sample injector and a detector (FID) part were set to 300° C. and 300° C., respectively. A sample was dissolved in acetone and prepared to be a 1 weight % solution, and then 1 microliter of the solution obtained was injected into the sample injector. A recorder such as GC Solution System made by Shimadzu Corporation was used.

HPLC Analysis

For measurement, Prominence (LC-20 AD; SPD-20A) made by Shimadzu Corporation was used. As a column, YMC-Pack ODS-A (length: 150 mm, inner diameter: 4.6 mm, particle diameter: 5 m) made by YMC GmbH was used. As an eluate, acetonitrile and water were appropriately mixed and used. As a detector, a UV detector, an RI detector, a CORONA detector or the like was appropriately used.

When the UV detector was used, a detection wavelength was adjusted to 254 nanometers. A sample was dissolved in acetonitrile and prepared to be a 0.1 weight % solution, and then 1 microliter of the solution was injected into a sample injector. As a recorder, C-R7Aplus made by Shimadzu Corporation was used.

Ultraviolet-Visible Spectrophotometry

For measurement, PharmaSpec UV-1700 made by Shimadzu Corporation was used. A detection wavelength was adjusted in the range from 190 nanometers to 700 nanometers. A sample was dissolved in acetonitrile, and prepared to be a solution of 0.01 millimole per liter, and measurement was carried out by putting the solution in a quartz cell (optical path length 1 cm).

Sample for Measurement

Upon measuring phase structure and a transition temperature (a clearing point, a melting point, a polymerization starting temperature or the like), a liquid crystal compound itself was used as a sample. Upon measuring characteristics of a liquid crystal compound, such as a maximum temperature, viscosity, optical anisotropy and dielectric anisotropy, a mixture prepared by mixing the compound with a base liquid crystal was used as a sample. Upon measuring characteristics of a liquid crystal composition, the composition was used as was.

Measurement Method

Characteristics were measured by methods described below. Most of the measuring methods are applied as described in the Standard of the Japan Electronics and Information Technology Industries Association (JEITA EIAJ ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a scanning calorimeter, Diamond DSC System, made by PerkinElmer, Inc., or a high-sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to the liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point measuring apparatus equipped with a polarizing microscope and was heated at a rate of 1° C. per minute. Temperature when part of the sample began to change from a nematic phase to an isotropic liquid was measured. A higher limit of a temperature range of the nematic phase may be occasionally abbreviated as "maximum temperature." When the sample was a mixture of a liquid crystal compound and the base liquid crystal, the maximum temperature was expressed using a symbol $T_{NI}$. When the sample was a mixture of a liquid crystal compound and component B, C or D, the maximum temperature was expressed using a symbol NI.

(4) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., $T_c$ was expressed as $T_c \leq -20°$ C. A lower limit of the temperature range of the nematic phase may be occasionally abbreviated as "minimum temperature."

(5) Viscosity (Bulk Viscosity; η; Measured at 20° C.; mPa·s)

A cone-plate (E type) rotational viscometer made by Tokyo Keiki Inc. was used for measurement.

(6) Optical Anisotropy (Refractive Index Anisotropy; Measured at 25° C.; Δn)

Measurement was carried out by an Abbe refractometer having a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=n∥−n⊥.

(7) Specific Resistance (ρ; Measured at 25° C.; Ωcm)

Into a vessel equipped with electrodes, 1.0 milliliter of sample was injected. A DC voltage (10 V) was applied to the vessel, and a DC current after 10 seconds was measured. A specific resistance was calculated from the following equation: (Specific resistance)={(voltage)×(electric capacity of a vessel)}/{(direct current)×(dielectric constant of vacuum)}.

(8) Voltage Holding Ratio (VHR-1; Measured at 25° C.; %)

A TN device used for measurement had a polyimide alignment film and a distance (cell gap) between two glass substrates was 5 micrometers. A sample was put in the device, and then the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(9) Voltage Holding Ratio (VHR-2; Measured at 80° C.; %)

A voltage holding ratio was measured in procedures identical with the procedures described above except that the voltage holding ratio was measured at 80° C. in place of 25° C. The thus obtained results were expressed in terms of VHR-2.

(10) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After 0.2 seconds with no voltage application, voltage was applied repeatedly under conditions of only one rectangular wave (rectangular pulse; 0.2 seconds) and no application (2 seconds). A peak current and a peak time of a transient current generated by the applied voltage were measured. A value of rotational viscosity was obtained from the measured values according to calculating equation (8) on page 40 of the paper presented by M. Imai et al. A value of dielectric anisotropy required for the calculation was determined using the device by which the rotational viscosity was measured and by a method described below.

(11) Dielectric Anisotropy (Δ∈; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in the major axis direction of liquid crystal molecules was measured. Sine waves (0.5 V, 1 kHz) were applied to the device, and after 2 seconds, a dielectric constant (∈⊥) in the minor axis direction of the liquid crystal molecules was measured. A value of dielectric anisotropy was calculated from an equation: Δ∈=∈∥−∈⊥.

(12) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is expressed using a mean value of the thus determined $K_{11}$, $K_{22}$ and $K_{33}$.

(13) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 90% transmittance.

(14) Response Time (τ; Measured at 25° C.; Ms)

An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 micrometers and a twist angle was 80 degrees. Rectangular waves (60 Hz, 5 V, 0.5 seconds) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr; millisecond) is a time taken to change 90% of transmissivity to 10%. A fall time (τf: millisecond) is a time taken to change 10% of transmissivity to 90%. Response time was expressed by a sum of the thus obtained rise time and fall time.

Synthesis Example 1

Synthesis of bis(2,2,6,6-tetramethylpiperidine-4-yl)-1,1'-biphenyl-4,4'-dicarboxylate (No. 85)

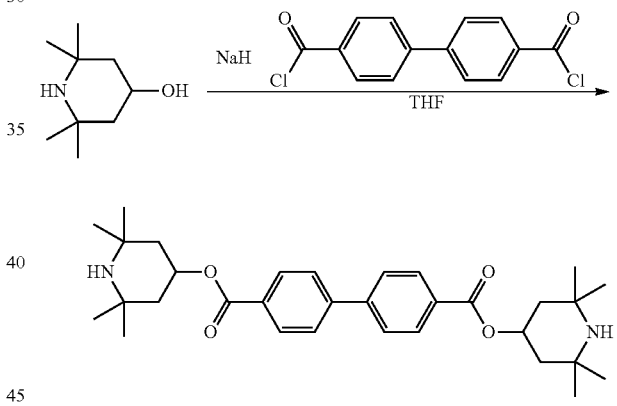

First Step

A mixture of 2,2,6,6-tetramethyl-4-piperidinol (15.00 g, 95.39 mmol) and NaH (60%, 3.80 g, 95.01 mmol) was heated under reflux in THF for 2 hours. The resulting reaction mixture was cooled to −10° C. or lower, and then a THF solution of 1,1'-biphenyl-4,4'-dicarbonyl dichloride (12.00 g, 43.00 mmol) was slowly added dropwise thereto while the mixture was maintained at the temperature. The resulting reaction mixture was stirred at room temperature for 1 hour, and then quenched with water. The resulting mixture was subjected to extraction with methyl t-butyl ether (MTBE). Silica gel was added to organic layers combined, and then filtered off. A solvent was distilled off from the resulting solution to give bis(2,2,6,6-tetramethyl-piperidine-4-yl)-1,1'-biphenyl-4,4'-dicarboxylate (No. 85) (6 g, yield: 26.7%).

$^1$H-NMR (δ ppm; CDCl$_3$): 8.12 (dd, 4H), 7.69 (dd, 4H), 5.48 (tt, 2H), 2.08 (dd, 4H), 1.57 (br, 2H), 1.36-1.31 (m, 16H), 1.21 (s, 12H).

Synthesis Example 2

Synthesis of bis(2,2,6,6-tetramethylpiperidine-4-yl) naphthalene-2,6-dicarboxylate (No. 8)

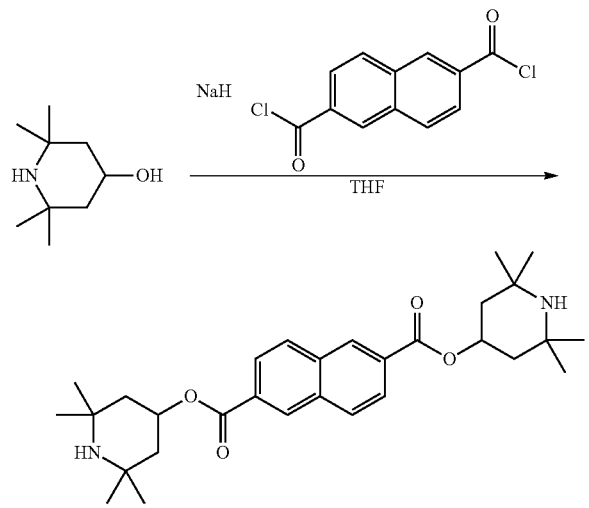

First Step

A mixture of 2,2,6,6-tetramethyl-4-piperidinol (13.70 g, 87.12 mmol) and NaH (60%, 2.09 g, 87.09 mmol) was heated under reflux in THF for 2 hours. The resulting reaction mixture was cooled to −10° C. or lower, and then a THF solution of naphthalene-2,6-dichloride dicarboxylic acid (10 g, 39.51 mmol) was slowly added dropwise thereto while the mixture was maintained at the temperature. The resulting reaction mixture was stirred at room temperature for 1 hour, and then quenched with water. The resulting mixture was subjected to extraction with MTBE. Silica gel was added to organic layers combined, and then filtered off. A solvent was distilled off from the resulting solution to give bis(2,2,6,6-tetramethylpiperidine-4-yl)naphthalene-2,6-dicarboxylate (No. 8) (5 g, yield: 25.6%).

$^1$H-NMR (δ ppm; CDCl$_3$): 8.60 (s, 2H), 8.11 (dd, 2H), 8.00 (d, 2H), 5.52 (tt, 2H), 2.12 (dd, 4H), 1.55 (br, 2H), 1.37 (t, 4H), 1.32 (s, 12H), 1.22 (s, 12H).

Synthesis Example 3

Synthesis of tetrakis(2,2,6,6-tetramethylpiperidine-4-yl)-1,1'-biphenyl-3,3',4,4'-tetracarboxylate

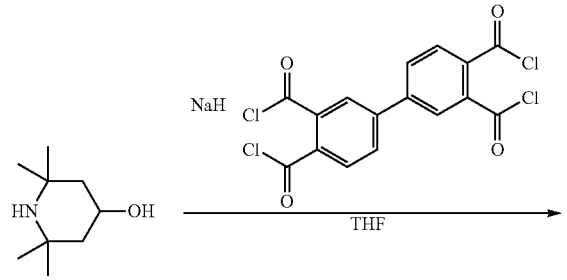

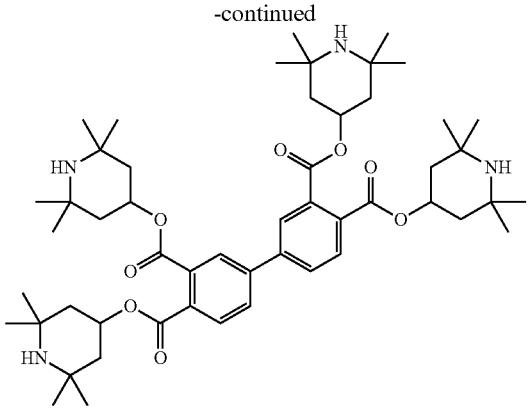

First Step

A mixture of 2,2,6,6-tetramethyl-4-piperidinol (6.85 g, 43.56 mmol) and NaH (60%, 1.05 g, 43.56 mmol) was heated under reflux in THF for 2 hours. The reaction mixture was cooled to −10° C. or lower, and then a THF solution of 1,1'-biphenyl-3,3',4,4'-tetracarboxylic acid tetrachloride (8.00 g, 19.80 mmol) was slowly added dropwise thereto while the mixture was maintained at the temperature. The resulting reaction mixture was stirred at room temperature for 1 hour, and then quenched with water. The resulting mixture was subjected to extraction with MTBE. Silica gel was added to organic layers combined, and then filtered off. A solvent was distilled off from the resulting solution to give tetrakis(2,2,6,6-tetramethylpiperidine-4-yl)-1,1'-biphenyl-3,3',4,4'-tetracarboxylate (No. 105) (3.5 g, yield: 20.0%).

$^1$H-NMR (δ ppm; CDCl$_3$): 7.87 (dd, 2H), 7.83 (dd, 2H), 7.73 (dd, 2H), 5.52-5.42 (m, 4H), 2.12 (ddd, 8H), 1.35-1.20 (m, 60H).

Synthesis Example 4

Synthesis of bis(2,2,6,6-tetramethylpiperidine-4-yl) 3-fluoro-1,1'-biphenyl-4,4'-dicarboxylate (No. 86)

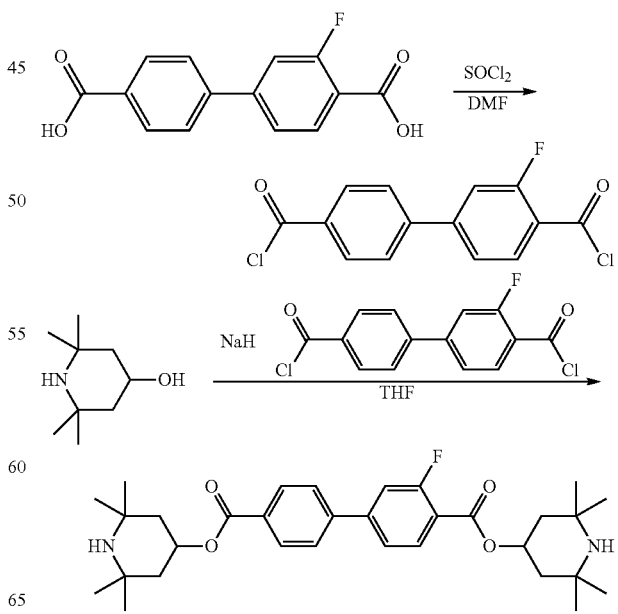

First Step

A mixture of 3-fluoro-1,1'-biphenyl-4,4'-dicarboxylic acid (12 g, 46.11 mmol), thionyl chloride (150 mL) and DMF (0.2 mL) was stirred under reflux for 3 hours. Then, thionyl chloride was distilled off from the resulting mixture, and then the resulting residue was purified by recrystallization to give 3-fluoro-1,1'-biphenyl-4,4'-dicarboxylic acid dichloride (11.8 g, yield: 86.2%).

Second Step

A mixture of 2,2,6,6-tetramethyl-4-piperidinol (13.75 g, 87.44 mmol) and NaH (60%, 2.10 g, 87.38 mmol) was heated under reflux in THF for 2 hours. The resulting reaction mixture was cooled to −10° C. or lower, and then a THF solution of 3-fluoro-1,1'-biphenyl-4,4'-dicarboxylic acid dichloride (11.8 g, 39.72 mmol) obtained in the first step was slowly added dropwise thereto while the mixture was maintained at the temperature. The resulting reaction mixture was stirred at room temperature for 1 hour, and then quenched with water. The resulting mixture was subjected to extraction with MTBE. Silica gel was added to organic layers combined, and then filtered off. A solvent was distilled off from the resulting solution to give bis(2,2,6,6-tetramethylpiperidine-4-yl)3-fluoro-1,1'-biphenyl-4,4'-dicarboxylate (No. 86) (6 g, yield: 28.1%).

$^1$H-NMR (δ ppm; CDCl$_3$): 8.12 (dd, 2H), 8.00 (dd, 1H), 7.66 (dd, 2H), 7.46 (dd, 1H), 7.39 (dd, 1H), 5.48 (tt, 2H), 2.10 (ddd, 4H), 1.62 (br, 1H), 1.37-1.17 (m, 29H).

Synthesis Example 5

Synthesis of bis(2,2,6,6-tetramethylpiperidine-4-yl)-1,1'-binaphthalene-4,4'-dicarboxylate (No. 225)

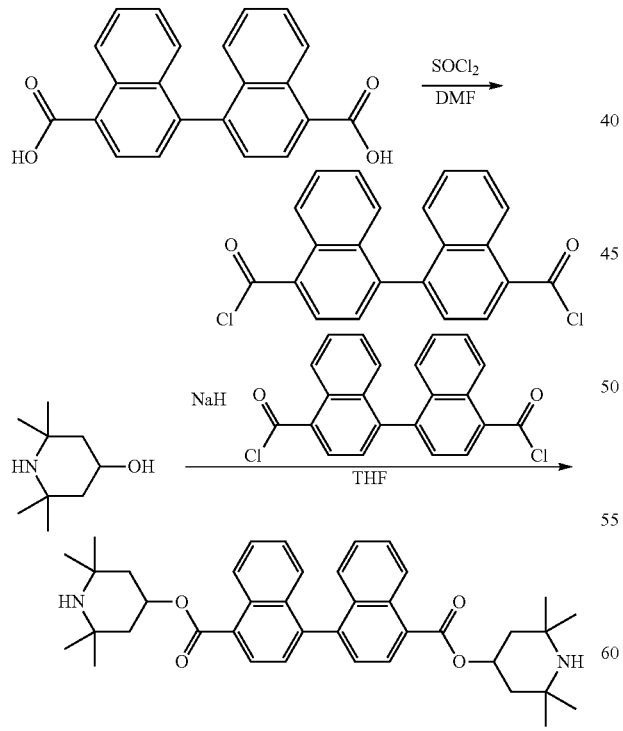

First Step

A mixture of 1,1'-binaphthalene-4,4'-dicarboxylic acid (10 g, 130 mL), thionyl chloride (130 mL) and DMF (0.3 mL) was stirred under reflux for 3 hours. Then, thionyl chloride was distilled off from the resulting mixture, and then the resulting residue was purified by recrystallization to give 1,1'-binaphthalene-4,4'-dicarbonyl dichloride (9.80 g, yield: 88.5%).

Second Step

A mixture of 2,2,6,6-tetramethyl-4-piperidinol (8.95 g, 56.91 mmol) and NaH (60%, 1.37 g, 57.09 mmol) was heated under reflux in THF for 2 hours. The resulting reaction mixture was cooled to −10° C. or lower, and then a THF solution of 1,1'-binaphthalene-4,4'-dicarbonyl dichloride (9.80 g, 25.84 mmol) obtained in the first step was slowly added dropwise thereto while the mixture was maintained at the temperature. The resulting reaction mixture was stirred at room temperature for 1 hour, and then quenched with water. The resulting mixture was subjected to extraction with MTBE. Silica gel was added to organic layers combined, and then filtered off. A solvent was distilled off from the resulting solution to give bis(2,2,6,6-tetramethylpiperidine-4-yl)-1,1'-binaphthalene-4,4'-dicarboxylate (No. 225) (4.3 g, yield: 26.8%).

$^1$H-NMR (δ ppm; CDCl$_3$): 8.99 (d, 2H), 8.24 (d, 2H), 7.61 (ddd, 2H), 7.49 (d, 2H), 7.38-7.32 (m, 4H), 5.63 (tt, 2H), 2.21 (ddd, 4H), 1.64 (br, 2H), 1.43-1.37 (m, 16H), 1.24 (s, 12H).

Comparative Example 1

Comparison of Solubility at Low Temperature

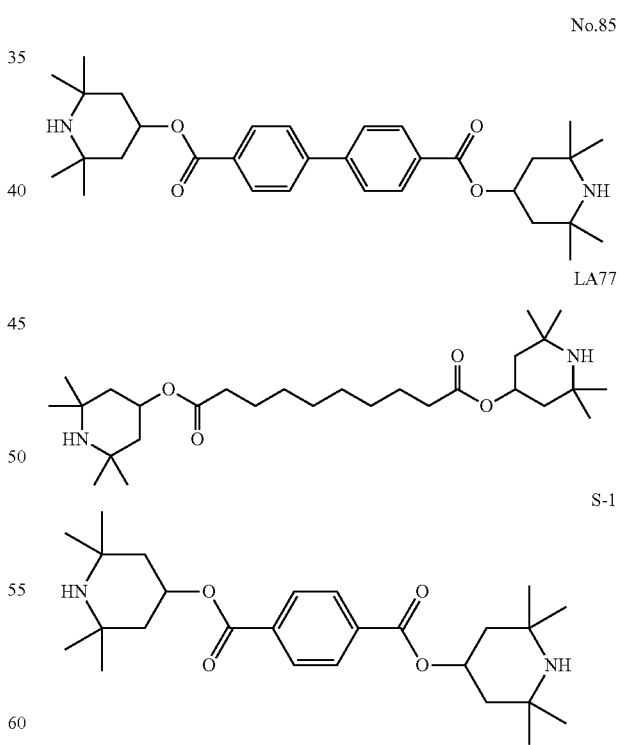

Comparison of solubility at a low temperature was made among compound (No. 85) of the invention, compound (LA77) and comparative compound (S-1). Compound (LA77) is a hindered amine light stabilizer made by ADEKA Corporation. To liquid crystal composition (A) described below, compound (No. 85) was added at a ratio of 0.1%, and the resulting mixture was heated at 50° C. for 30 minutes. The resulting solution was stored at −20° C. for 20 days. Then, whether or not a crystal precipitated was visually observed. On the other hand, comparative compound (LA77) and comparative compound (S-1) made by ADEKA Corporation were also observed in a manner similar to the above method. The results are shown in Table 2. With regard to the symbol in Table 2, a symbol "○" represents that no crystal precipitated, and a symbol "x" represents that the crystal precipitated. Table 2 shows that the solubility of compound (No. 85) of the invention in liquid crystal composition (A) is satisfactory. In addition, components and ratios thereof in liquid crystal composition (A) were as described below.

Liquid Crystal Composition (A)

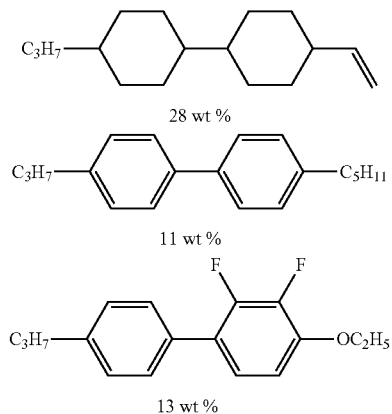

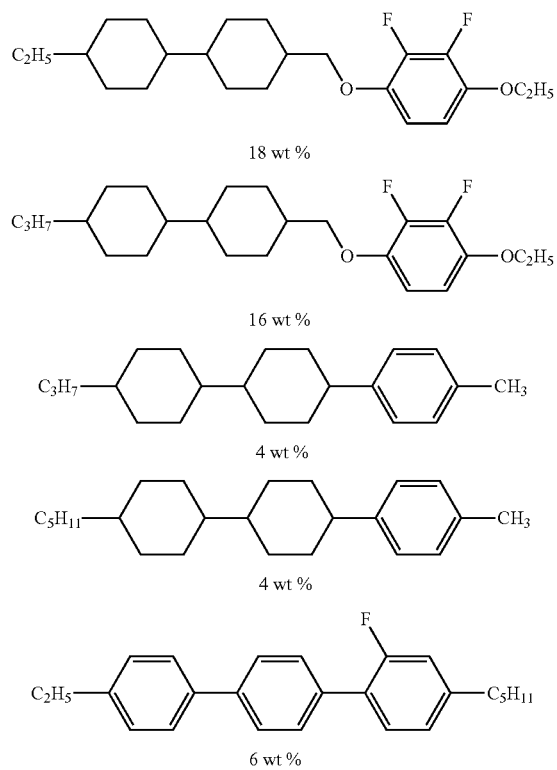

Characteristics of base liquid crystal A were as described below: NI=76.0° C.; Δn=0.107; Δ∈=−3.0.

TABLE 2

| Compounds | Structural formula | Solubility (−20° C. for 20 days) |
|---|---|---|
| Compound (No. 85) | | ○ |
| Comparative compound (LA77) | | x |

TABLE 2-continued
Comparison of solubility in liquid crystal composition (A)
| Compounds | Structural formula | Solubility (−20° C. for 20 days) |
|---|---|---|
| Comparative compound (S-1) | 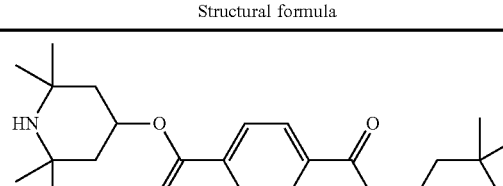 | X |
Compounds (No. 1) to (No. 291) shown below can be prepared according to synthesis methods described in Synthesis Examples 1 to 5.
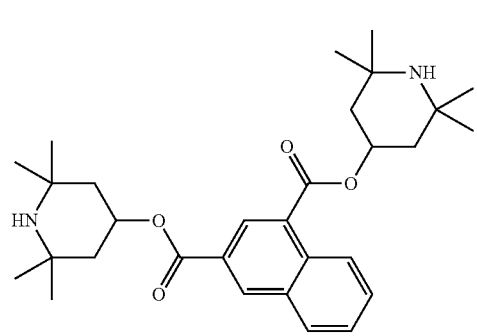
1
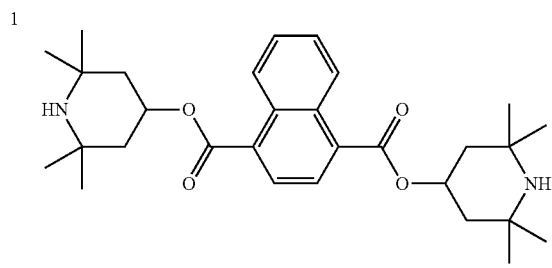
2
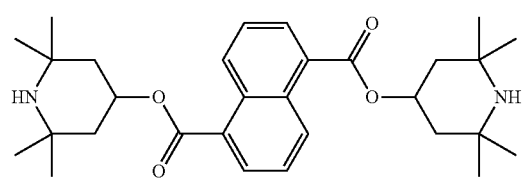
3
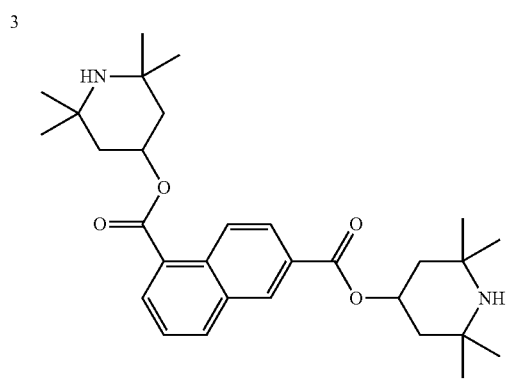
4
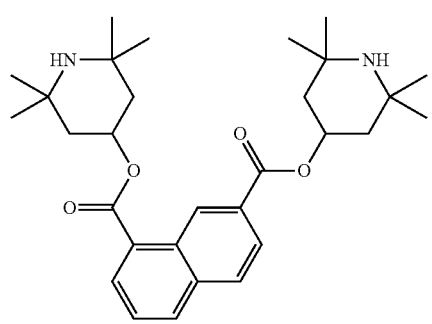
5
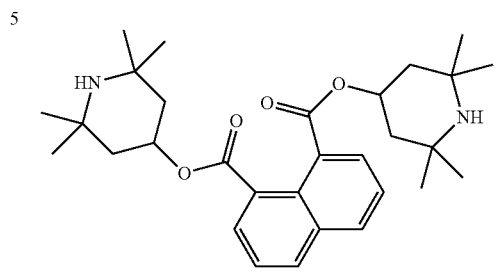
6

| 7 | 8 |
|---|---|
| 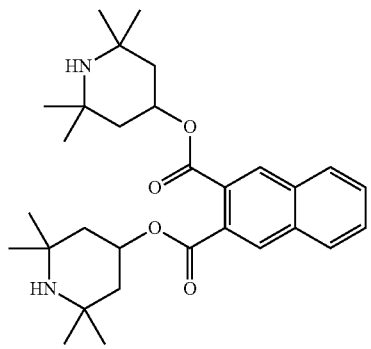 | 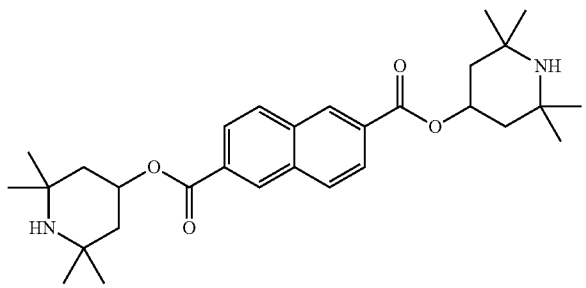 |
| 9 | 10 |
| 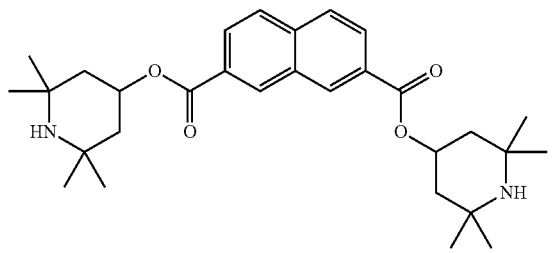 | 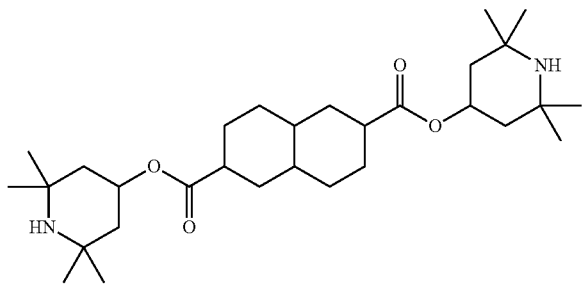 |
| 11 | 12 |
| 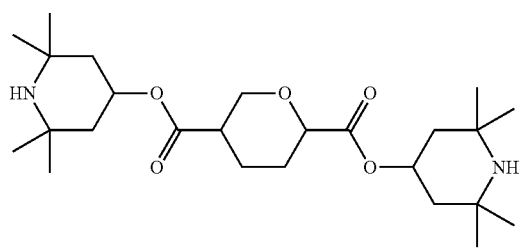 | 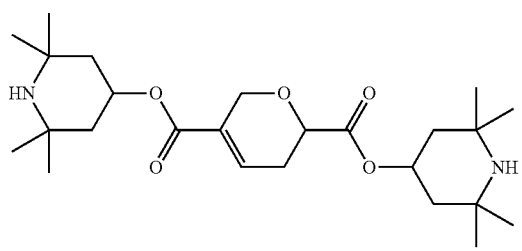 |
| 13 | 14 |
| 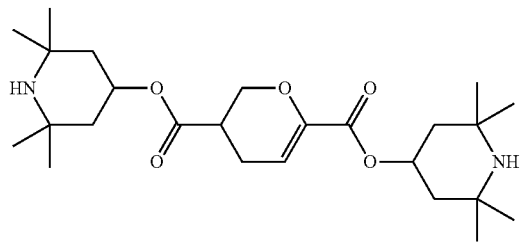 | 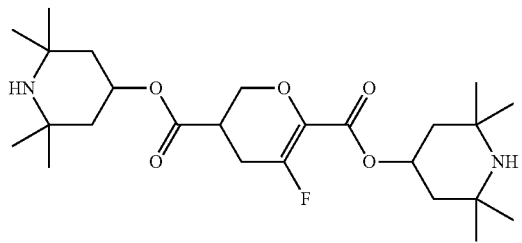 |
| 15 | 16 |
| 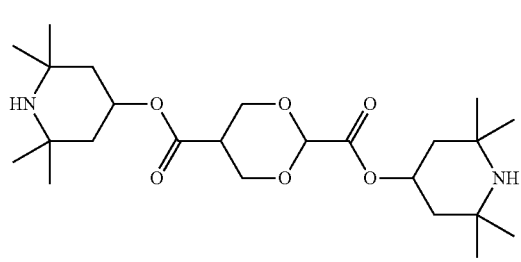 | 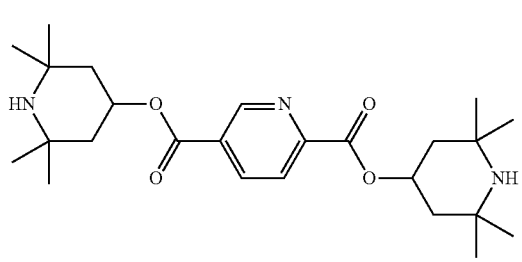 |

-continued
17
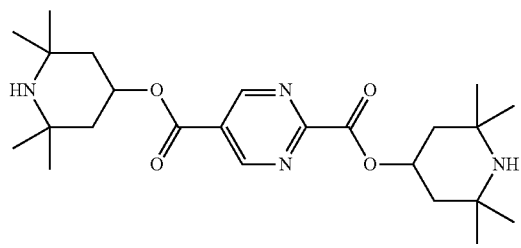
18
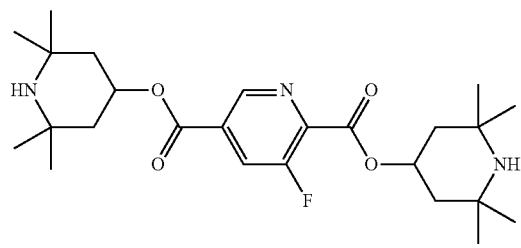
19
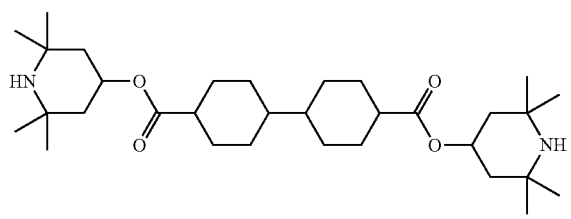
20
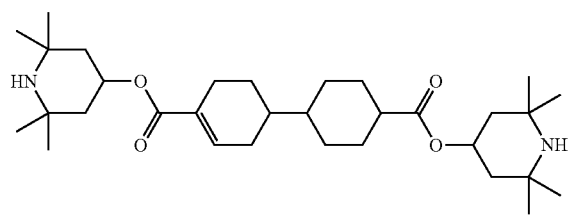
21
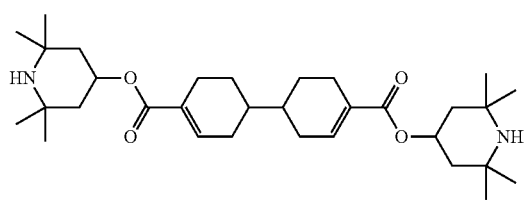
22
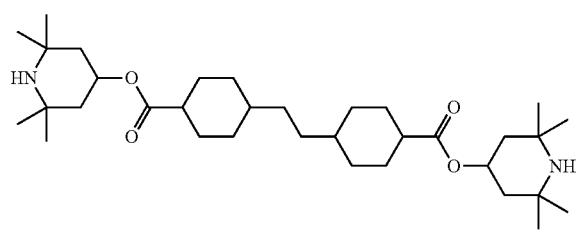
23
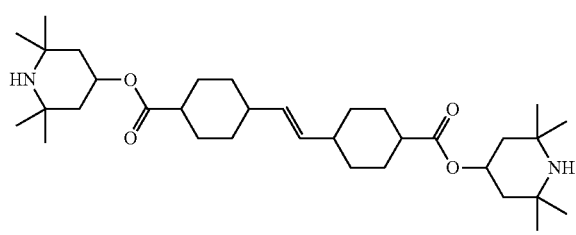
24
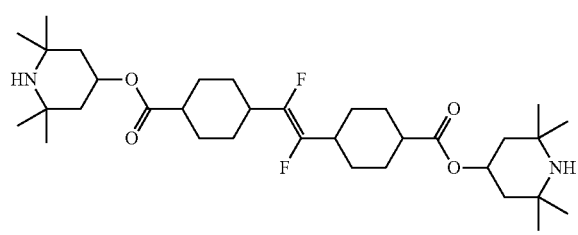
25
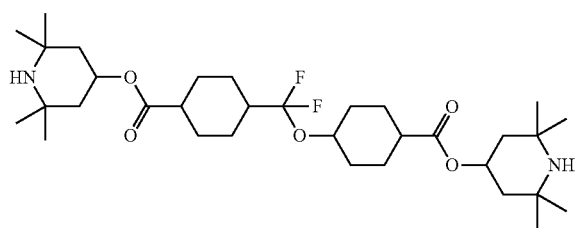
26
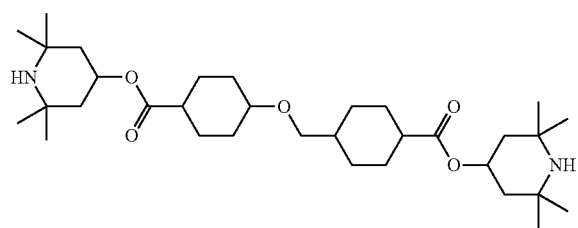
27
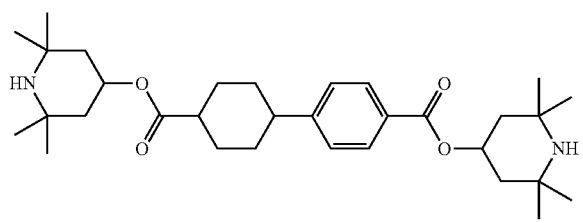
28
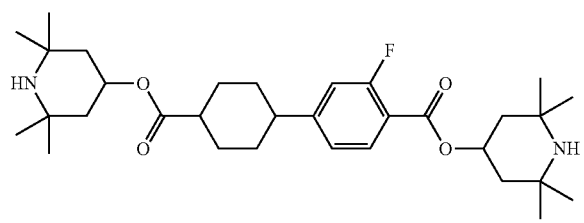

-continued
29
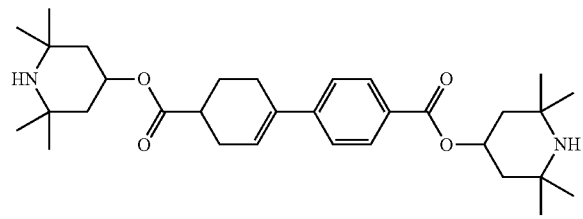
30
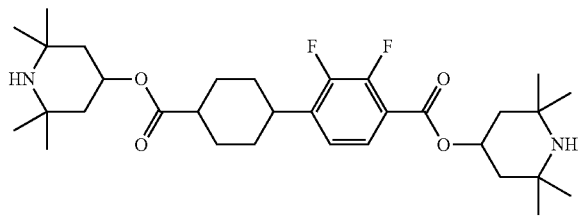
31
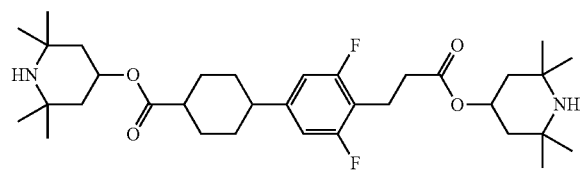
32
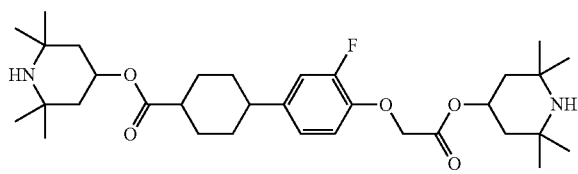
33
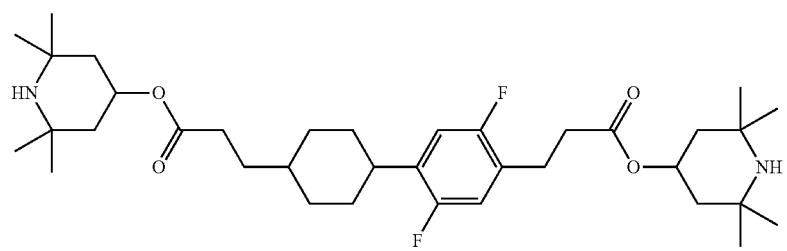
34
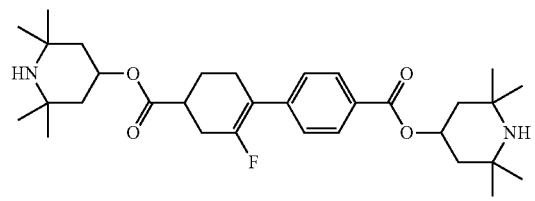
35
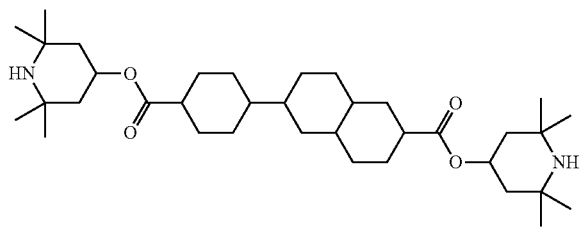
36
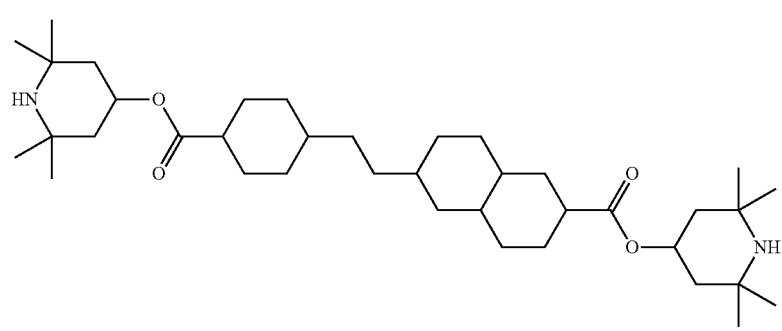
37
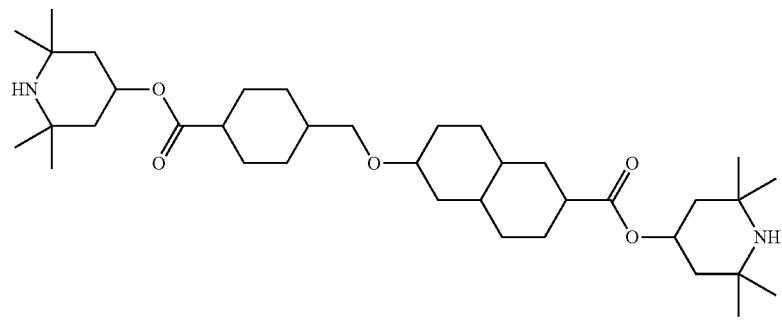

-continued
38
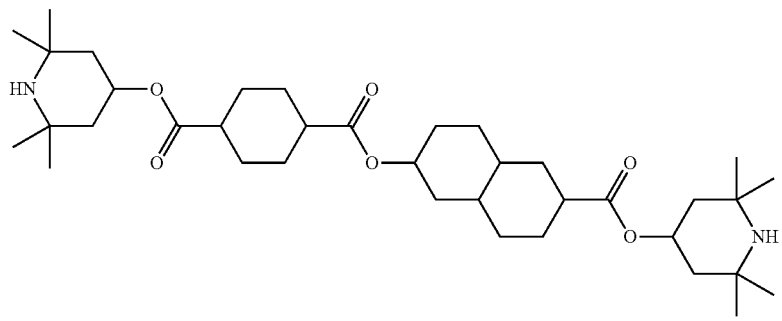
39
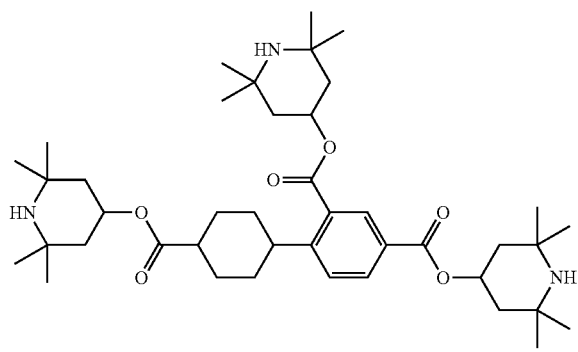
40
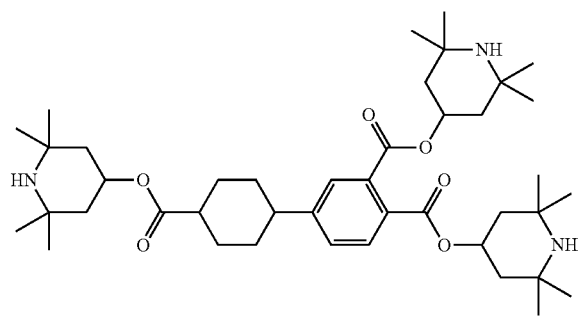
41
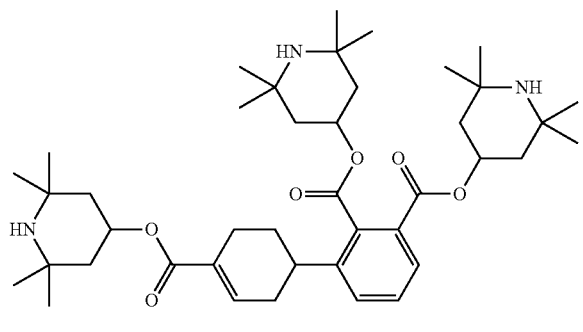
42
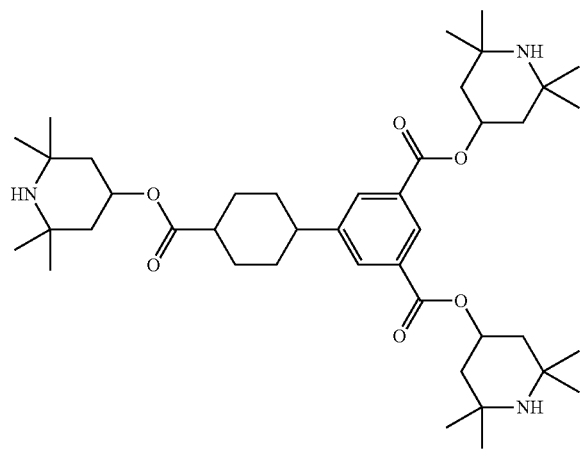
43
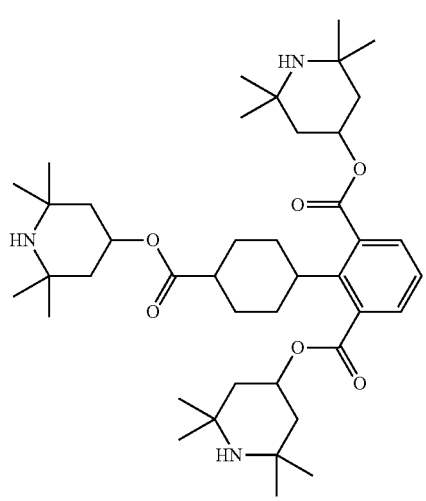
44
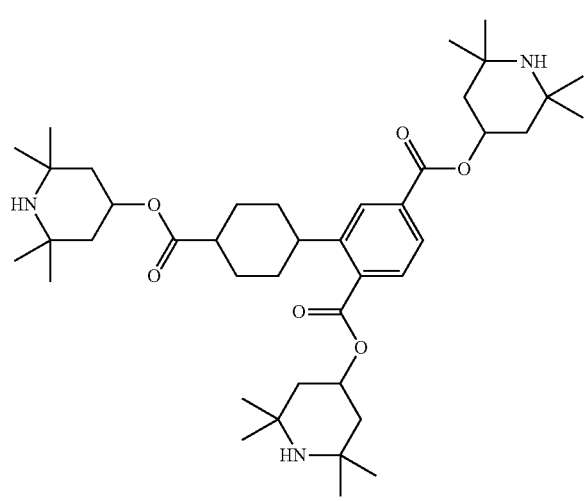

-continued
45
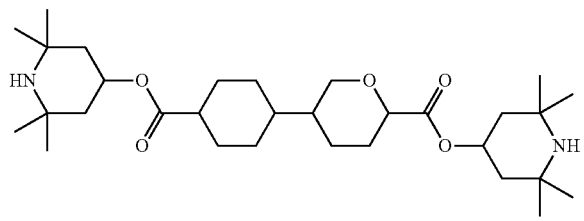
46
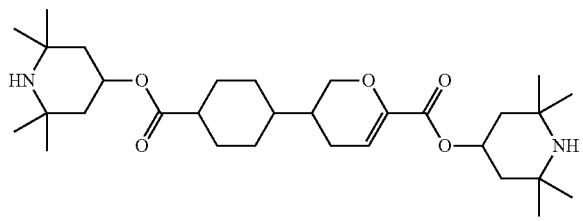
47
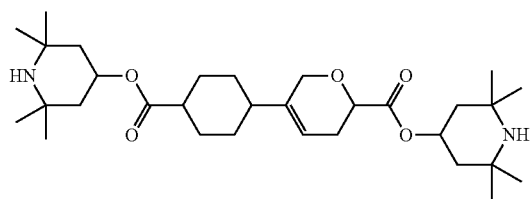
48
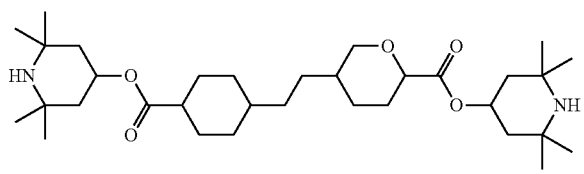
49
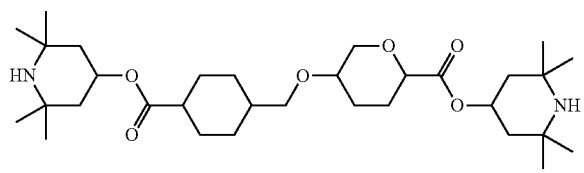
50
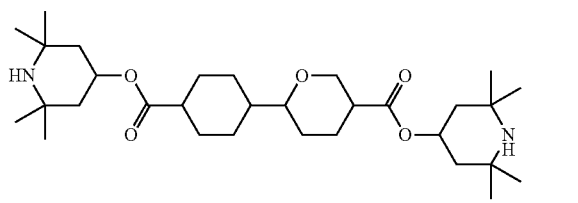
51
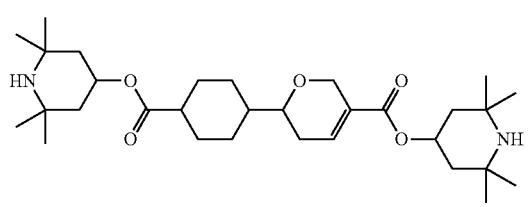
52
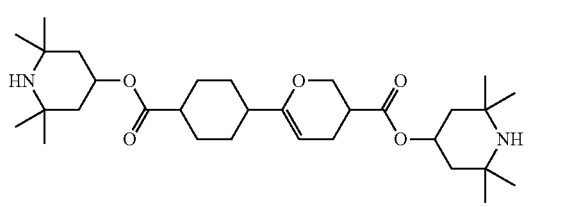
53
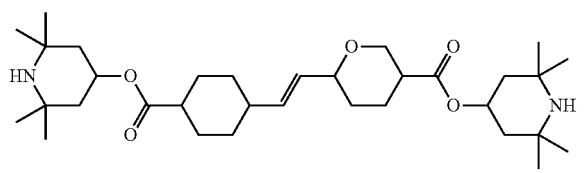
54
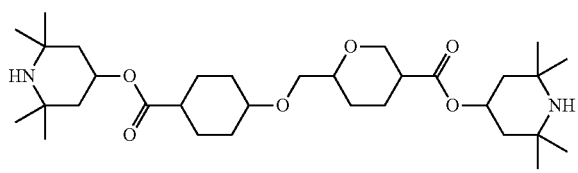
55
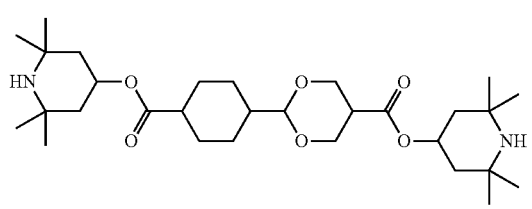
56
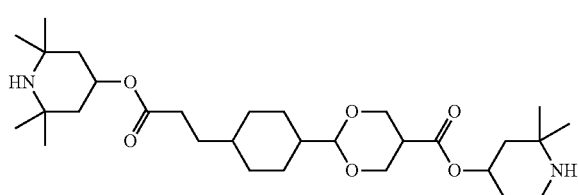
57
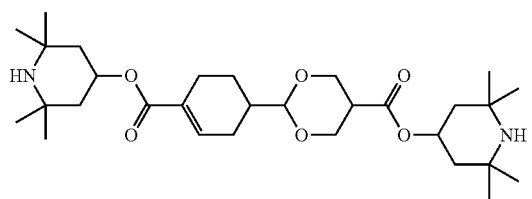
58
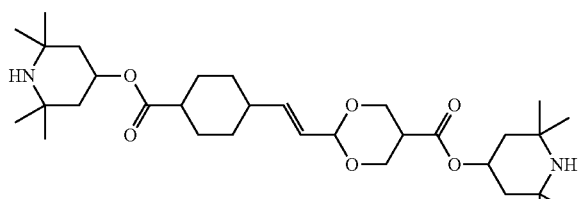

-continued
59
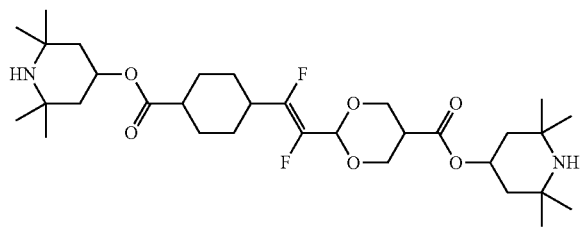
60
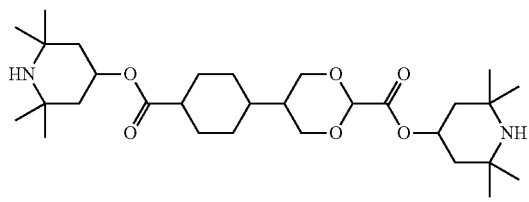
61
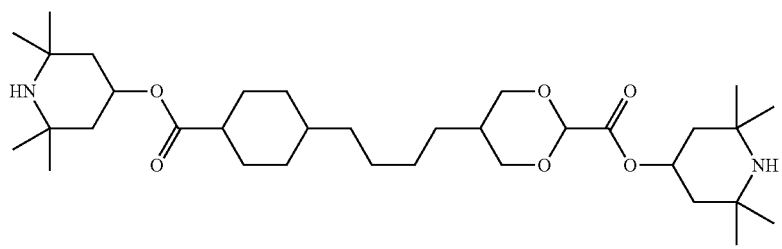
62
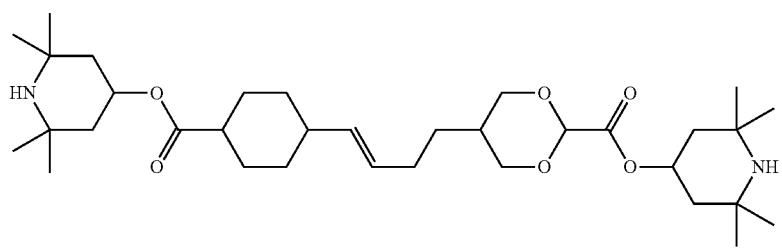
63
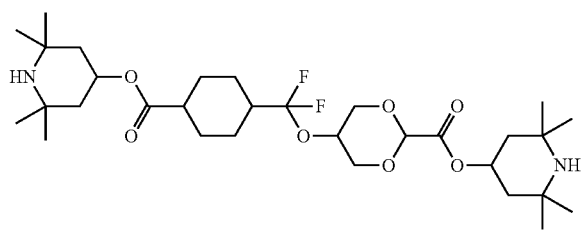
64
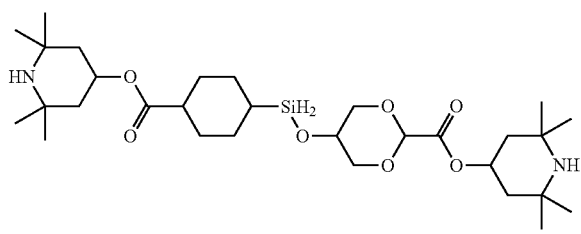
65
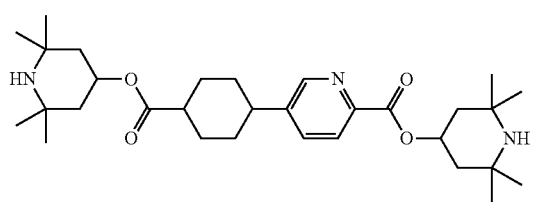
66
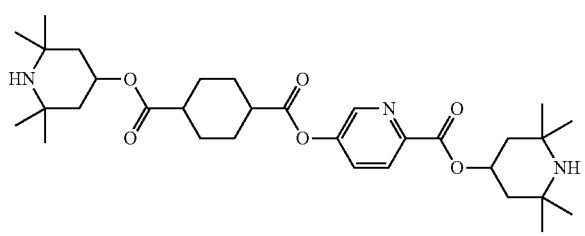
67
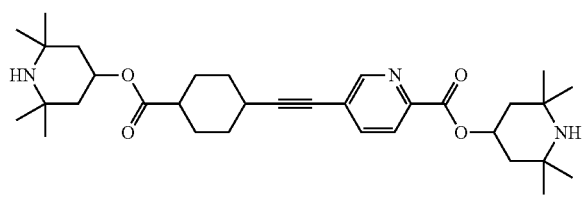
68
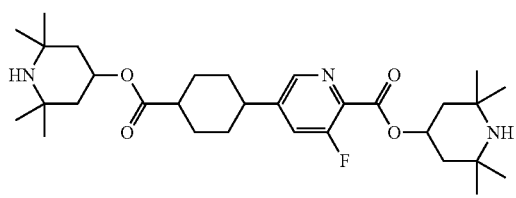

-continued
69
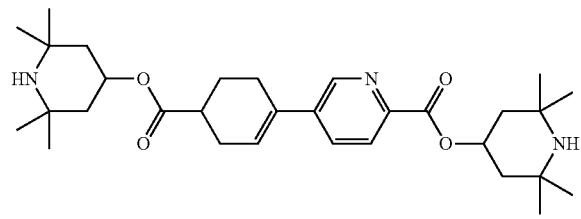
70
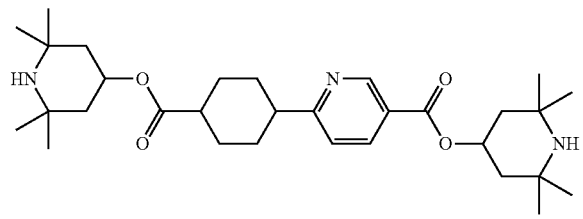
71
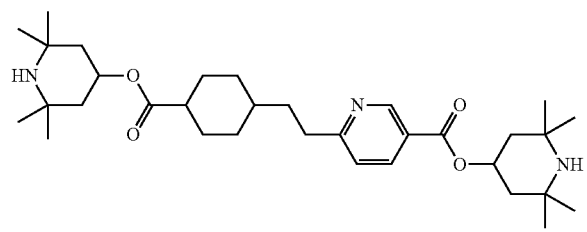
72
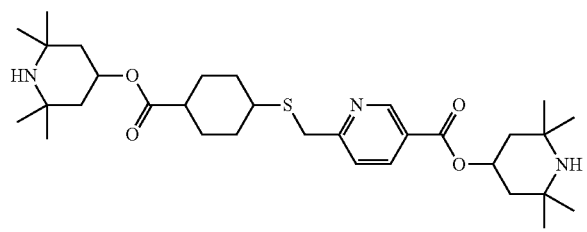
73
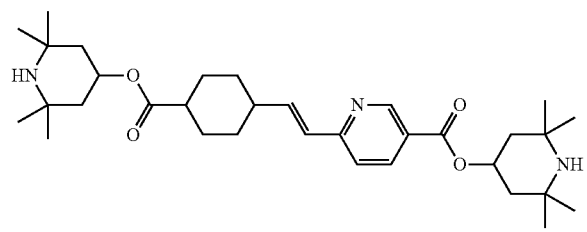
74
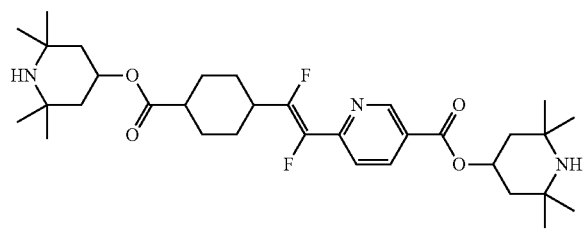
75
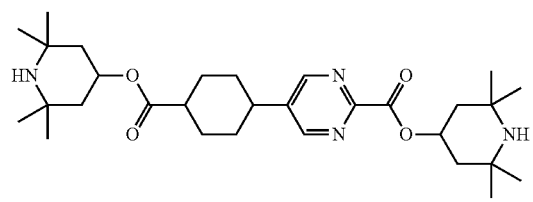
76
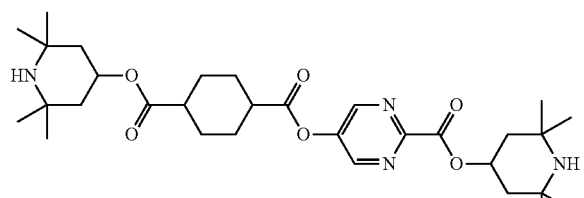
77
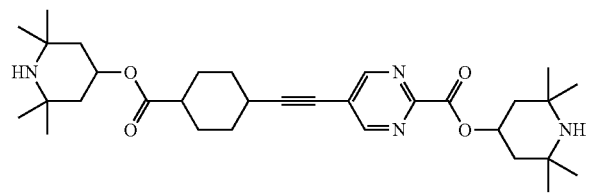
78
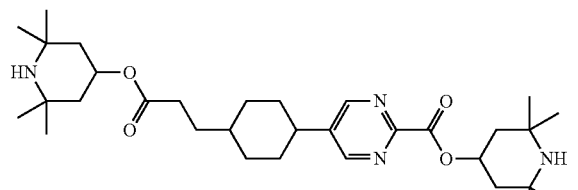
79
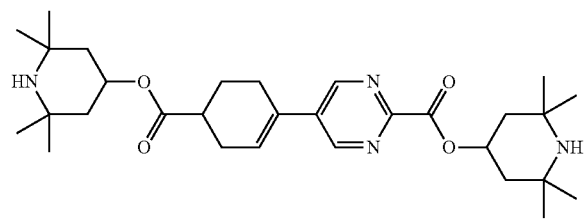
80
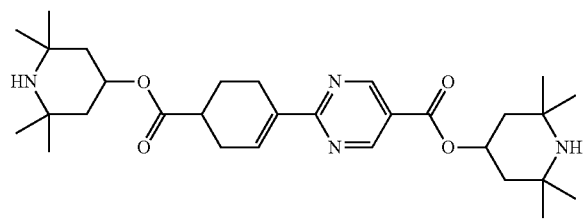

-continued
81
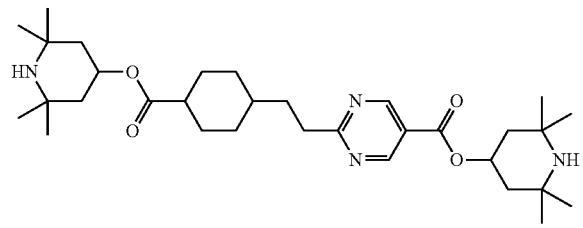
82
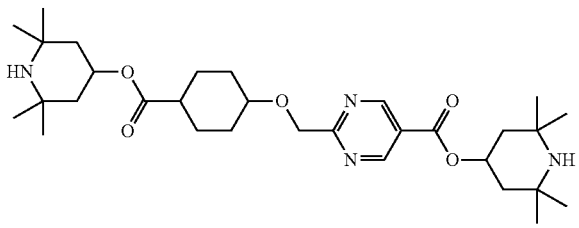
83
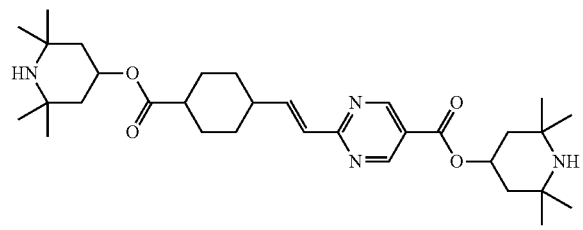
84
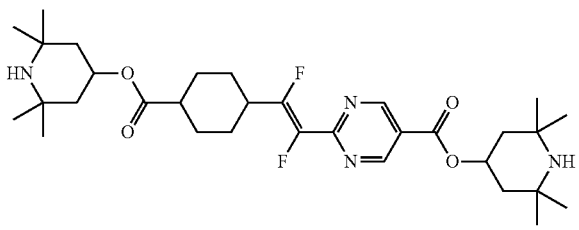
85
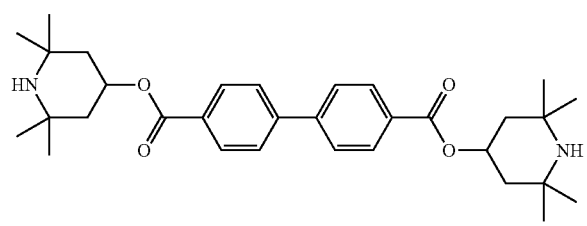
86
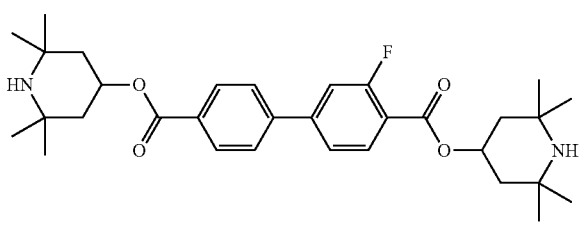
87
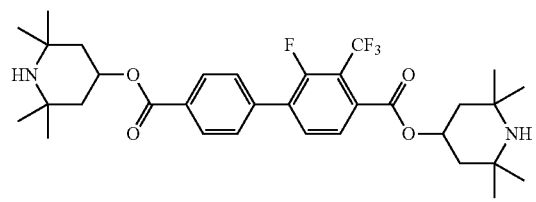
88
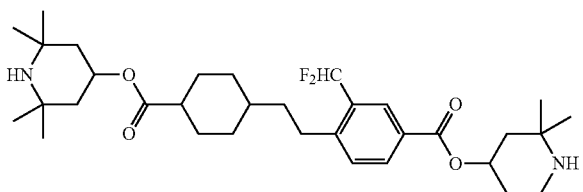
89
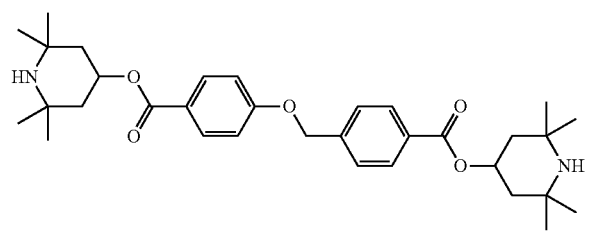
90
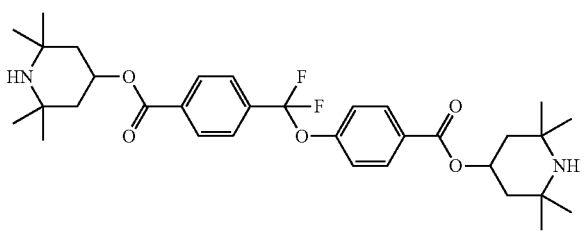
91
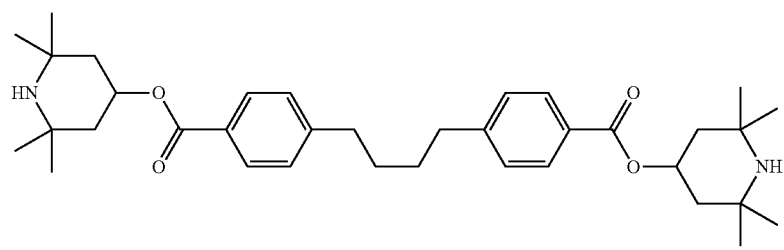

-continued
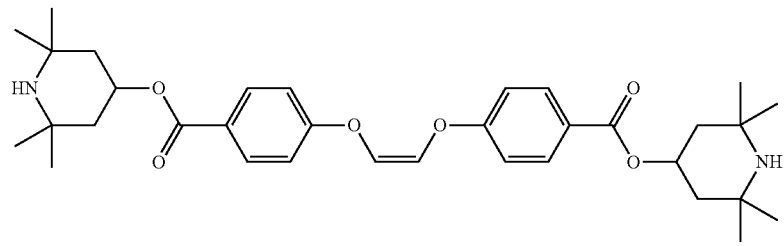
92
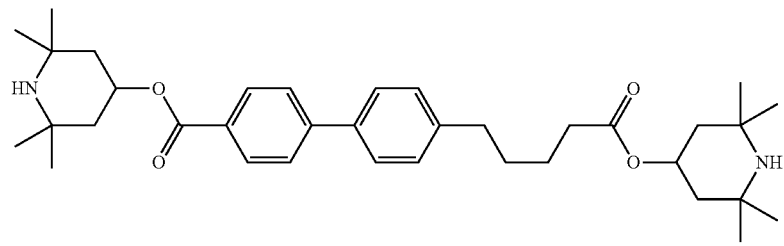
93
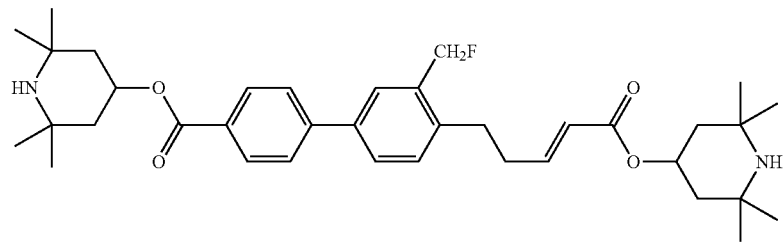
94
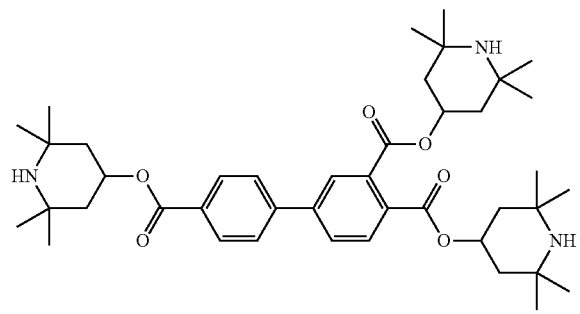
95
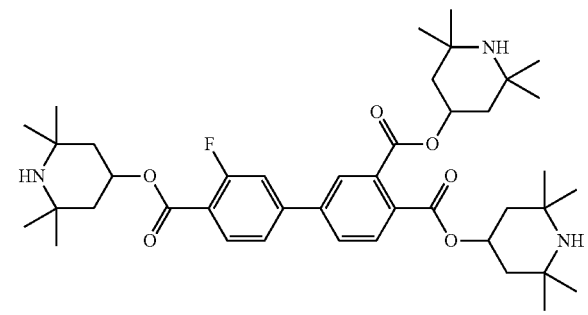
96
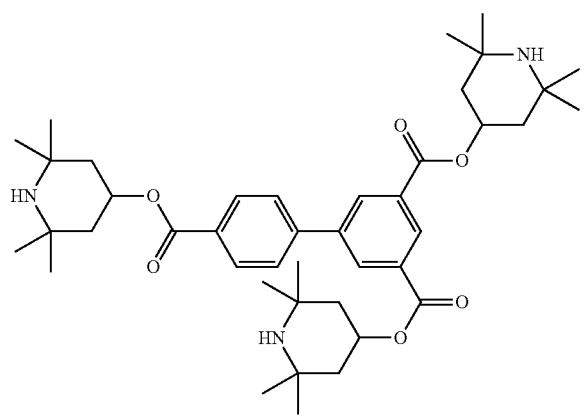
98

99 100
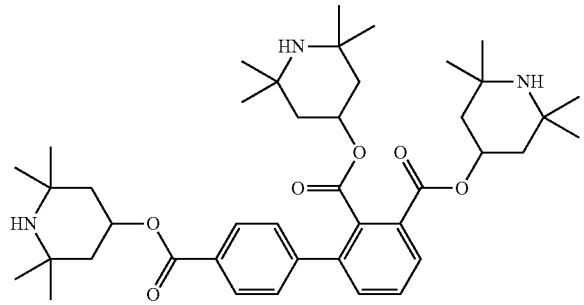
101 102
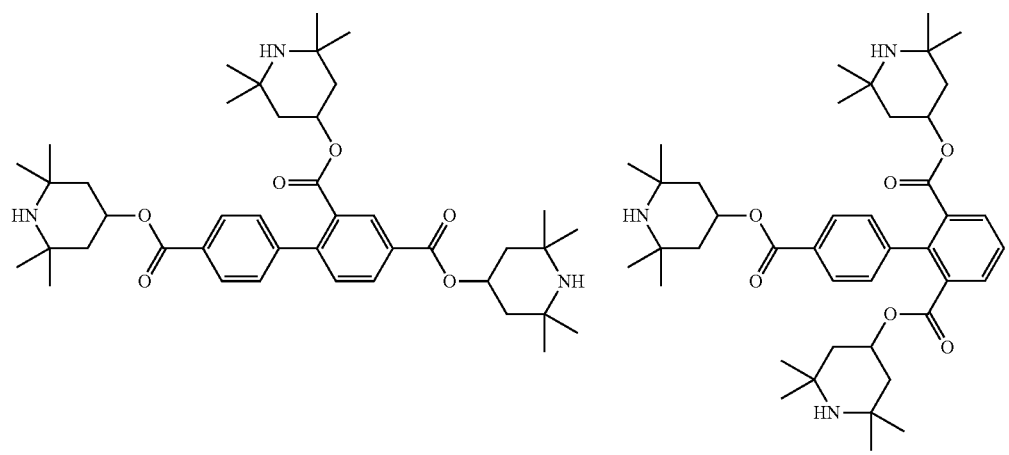
103 104
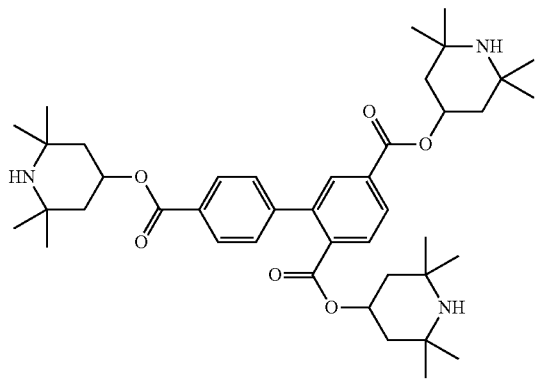
105 106
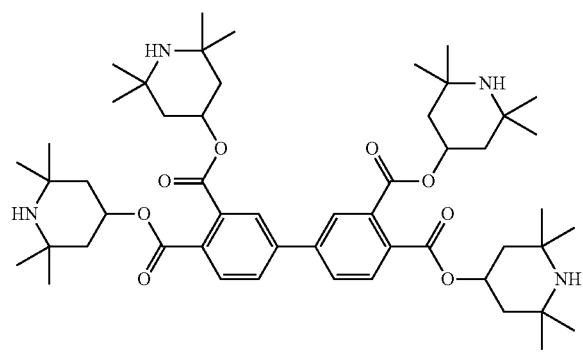

107
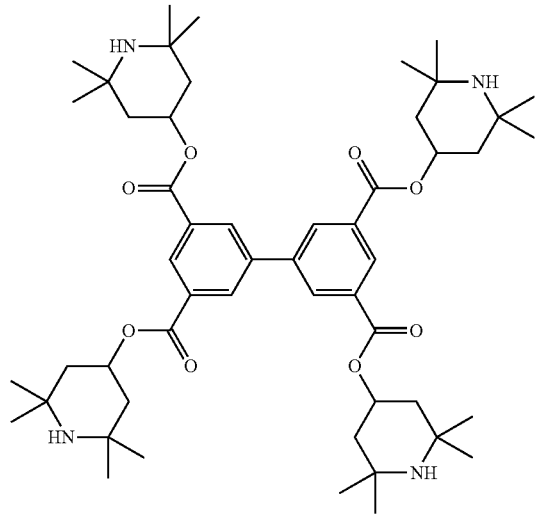
108
109
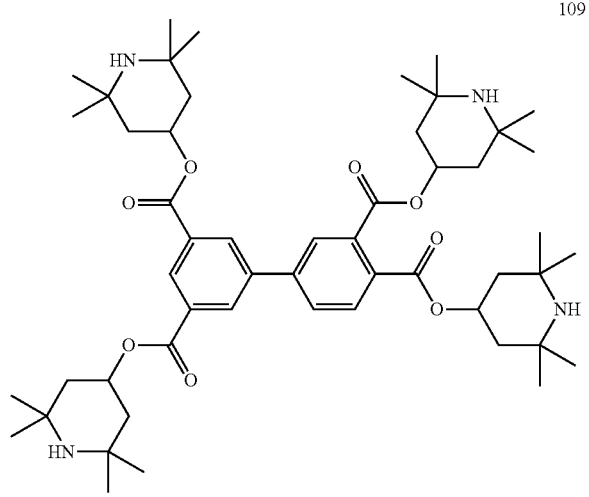
110
111
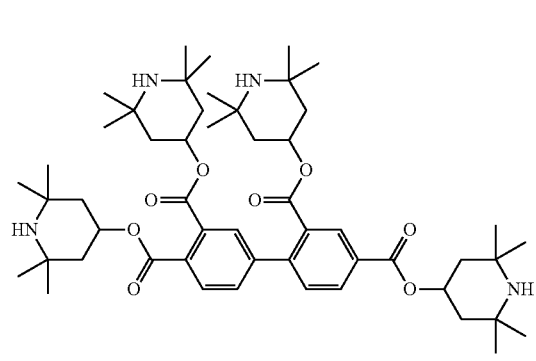
112
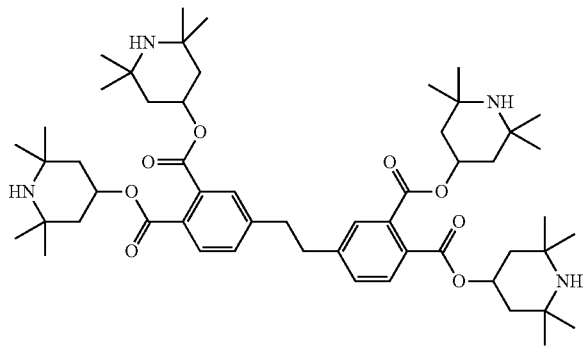

-continued
113
114
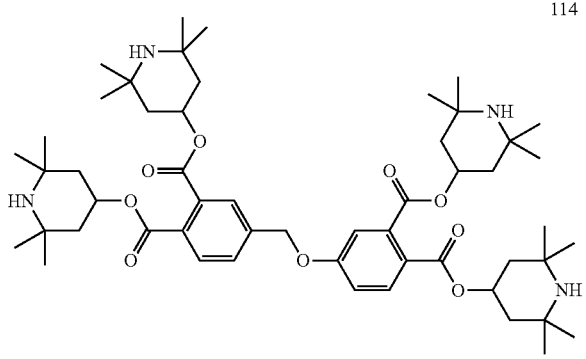
115
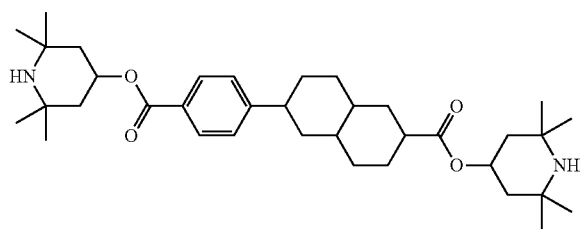
116
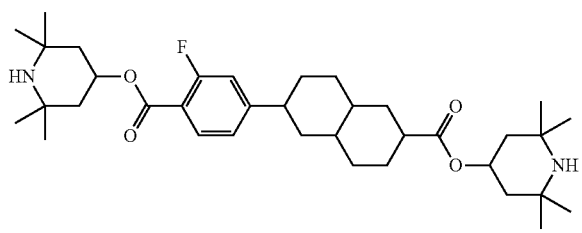
117
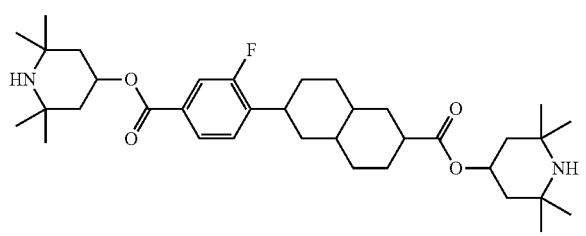
118
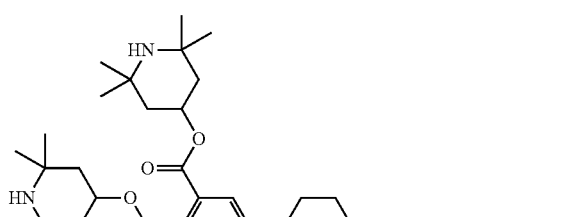
119
120
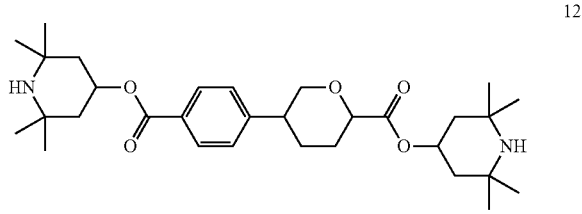
121
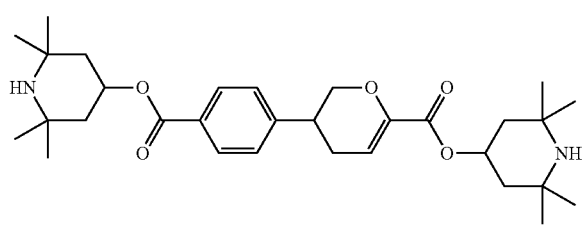
122
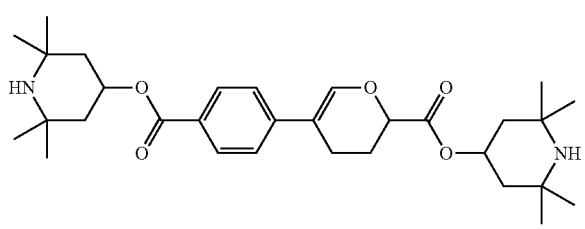
123
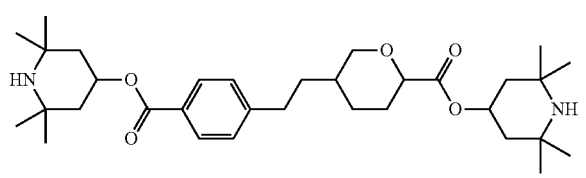
124
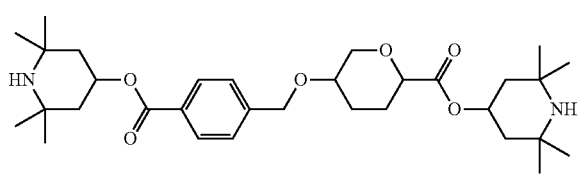

-continued
125
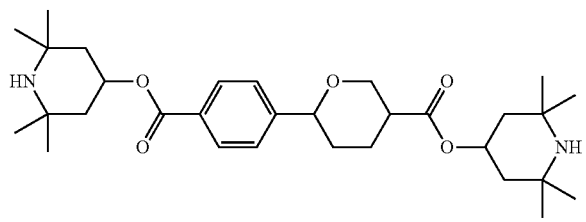
126
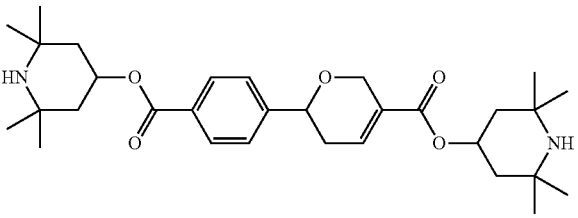
127
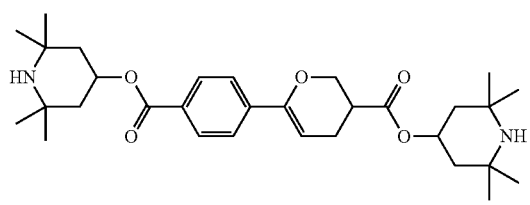
128
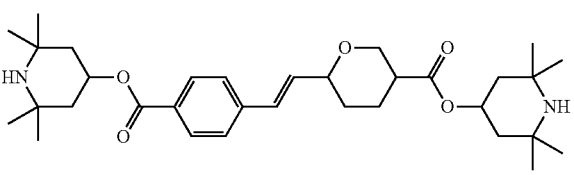
129
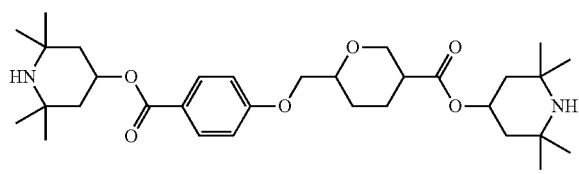
130
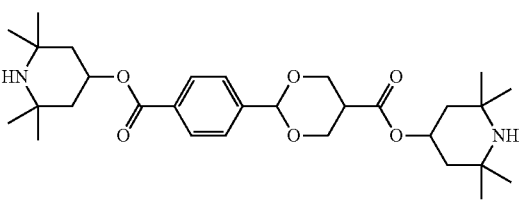
131
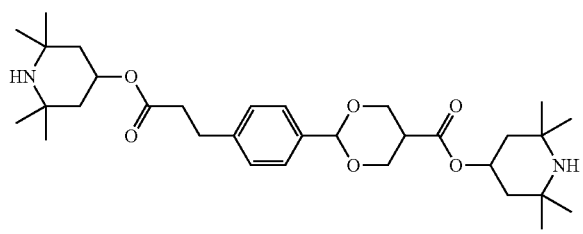
132
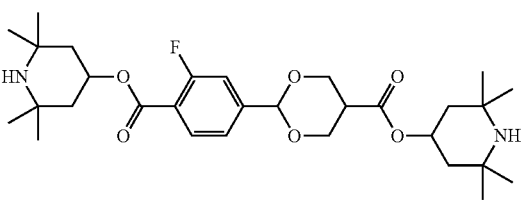
133
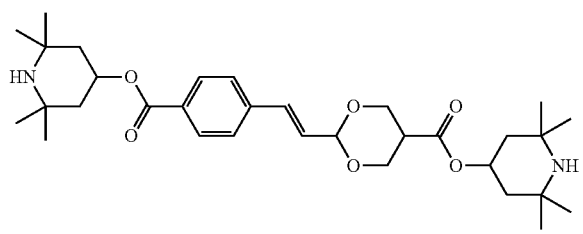
134
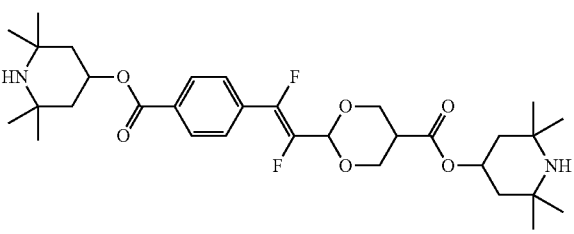
135
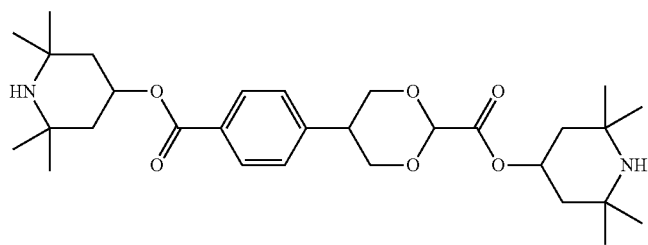

-continued
136
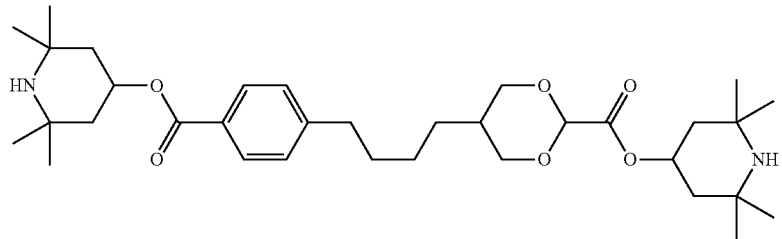
137
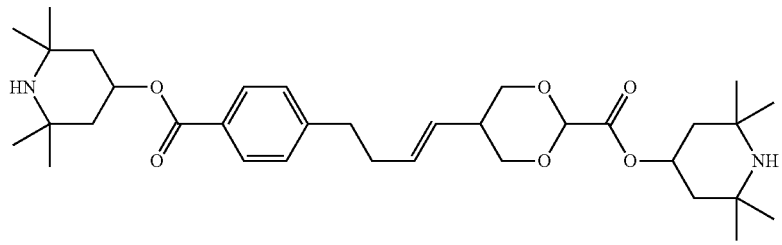
138
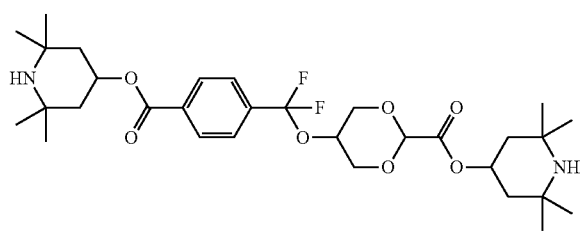
139
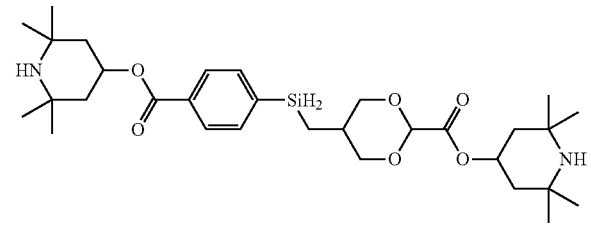
140
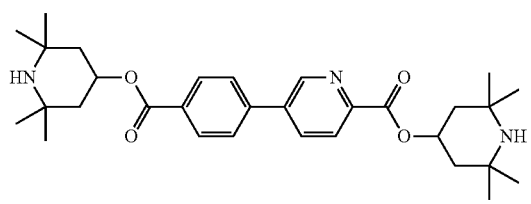
141
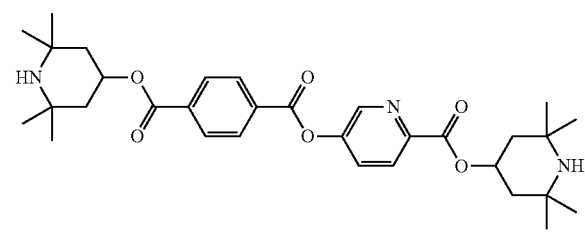
142
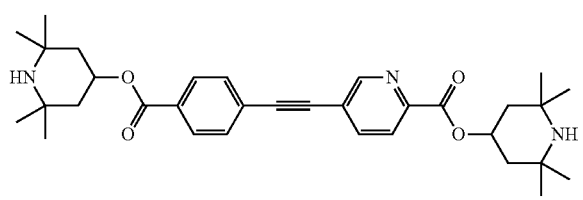
143
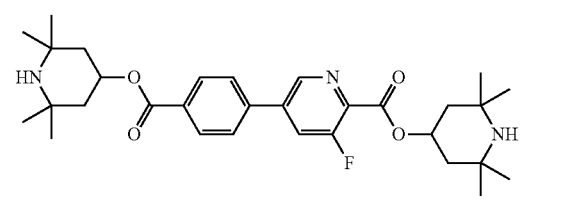
144
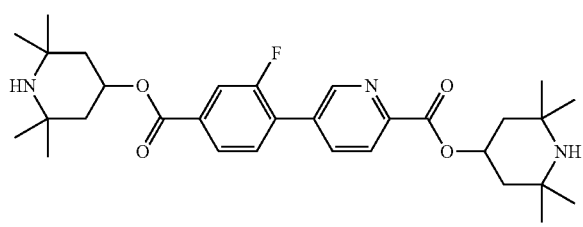
145
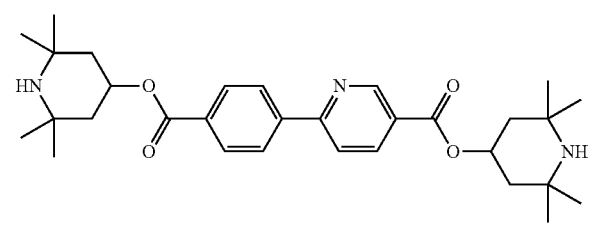

-continued
146
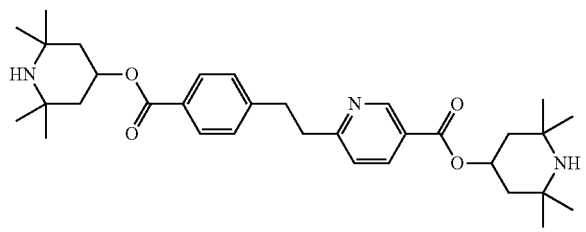
147
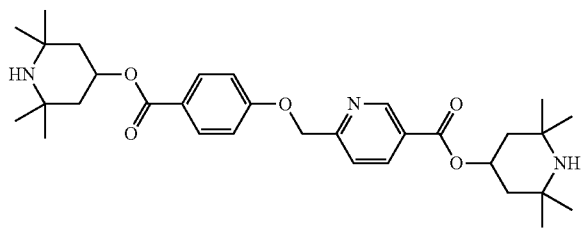
148
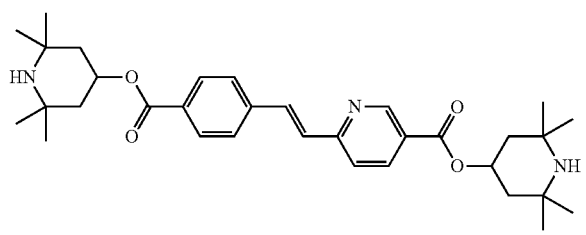
149
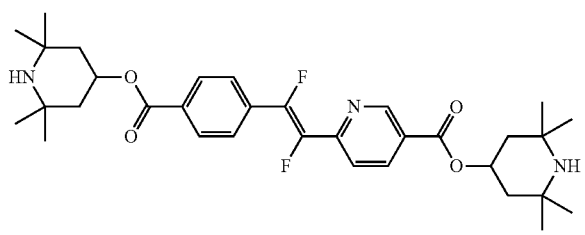
150
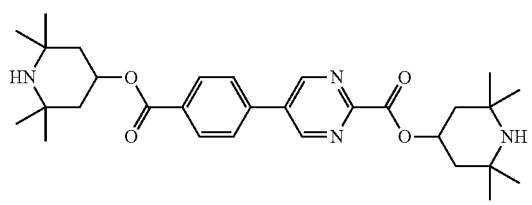
151
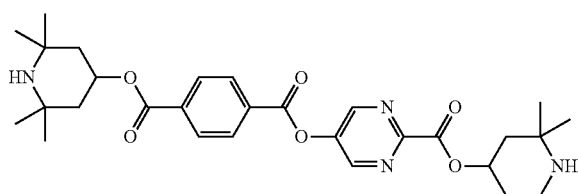
152
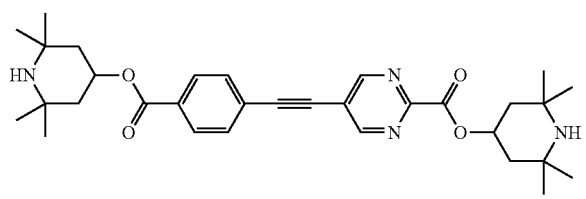
153
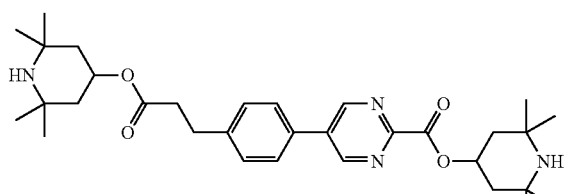
154
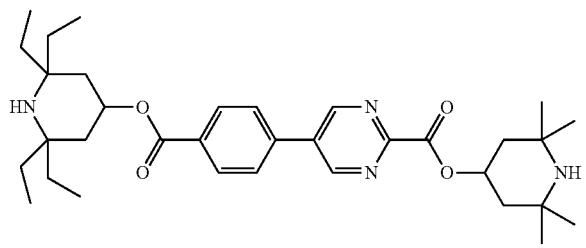
155
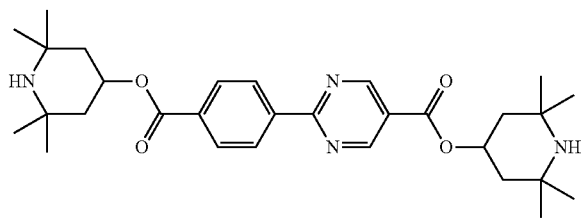
156
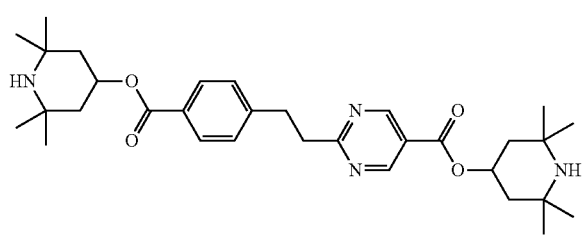
157
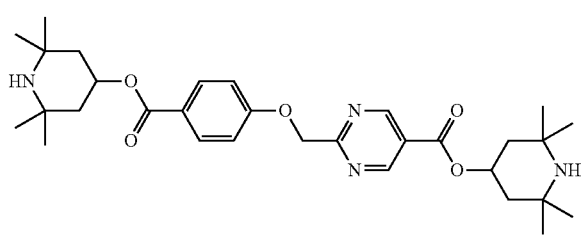

-continued
158
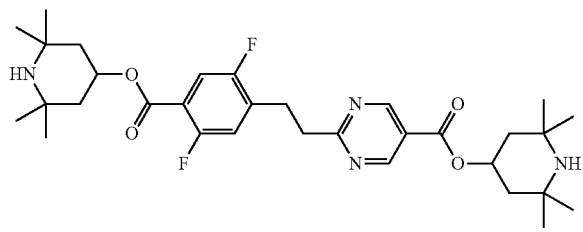
159
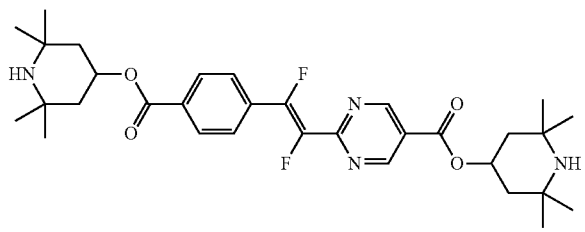
160
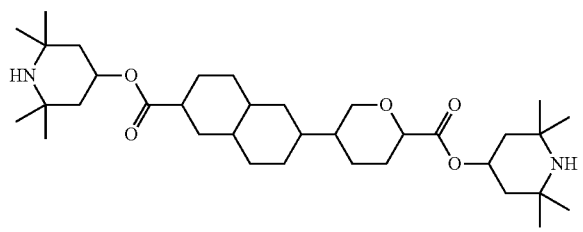
161
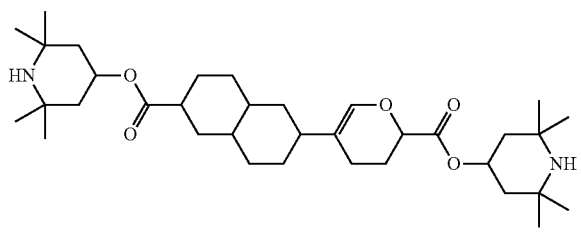
162
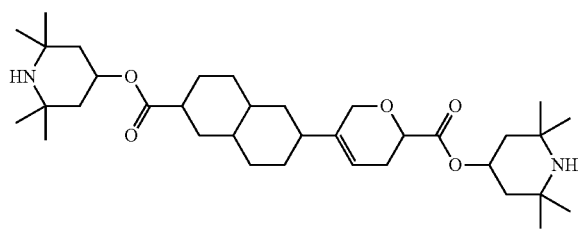
163
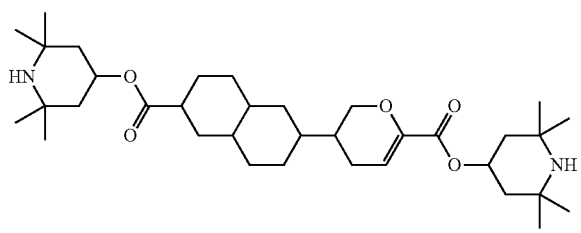
164
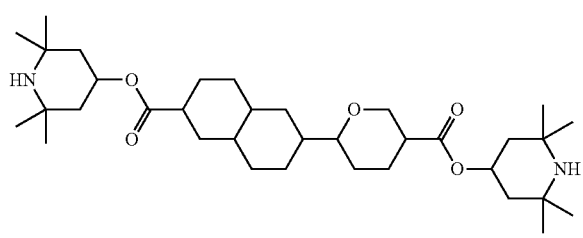
165
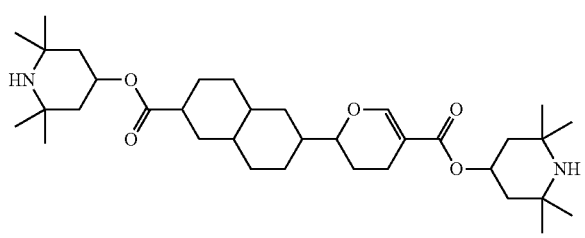
166
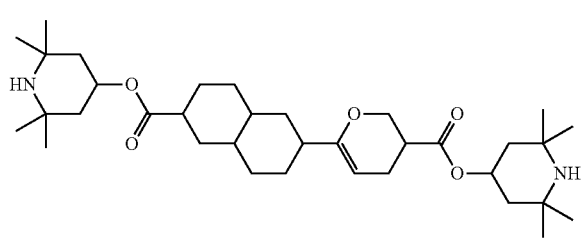
167
168
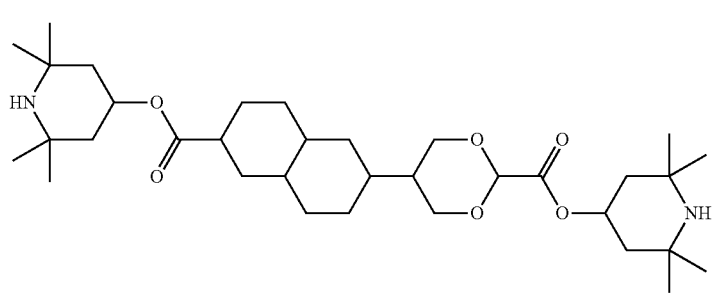

169
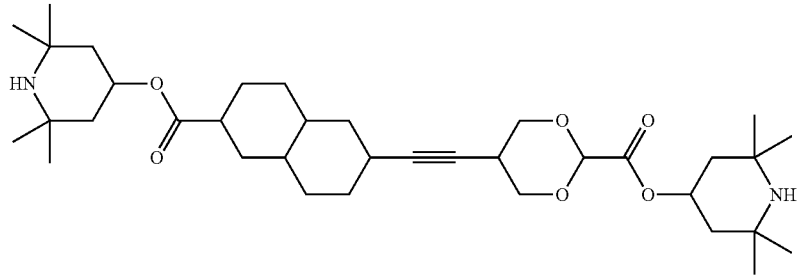
170
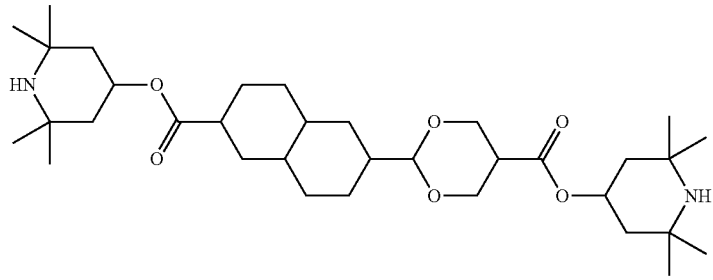
171
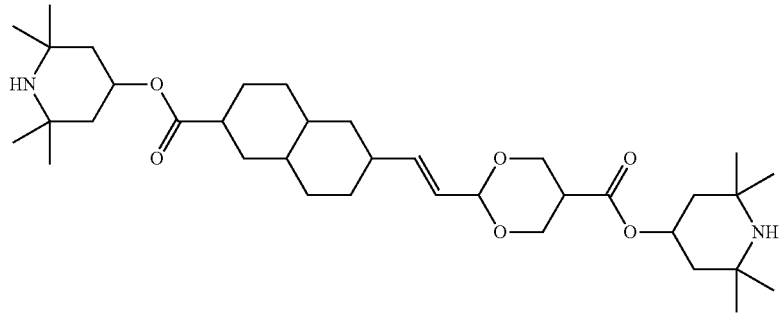
172
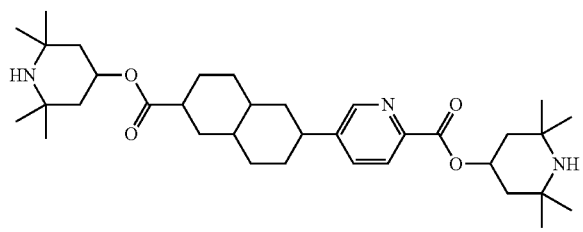
173
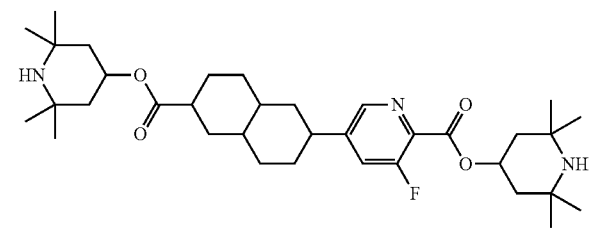
174
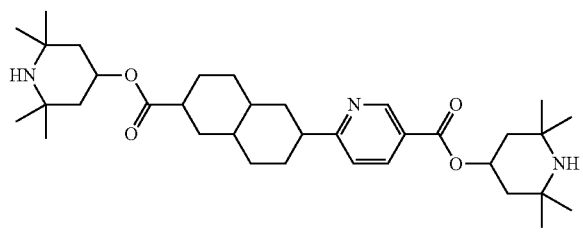
175
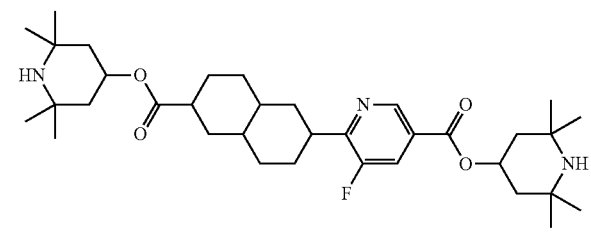

-continued
176
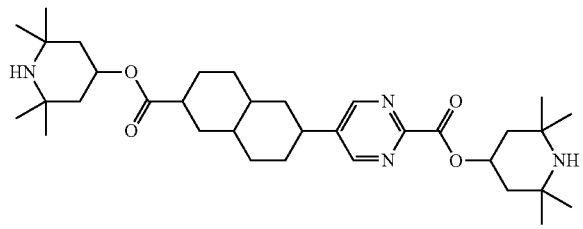
177
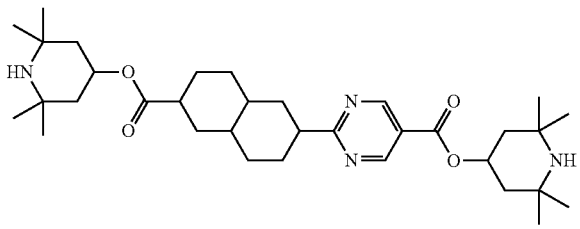
178
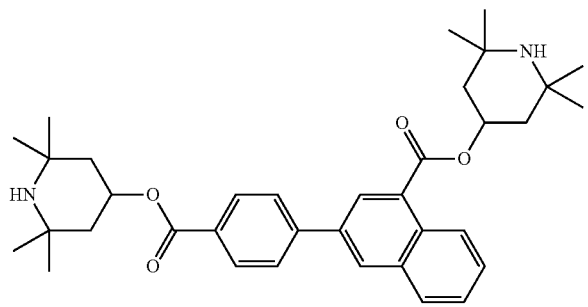
179
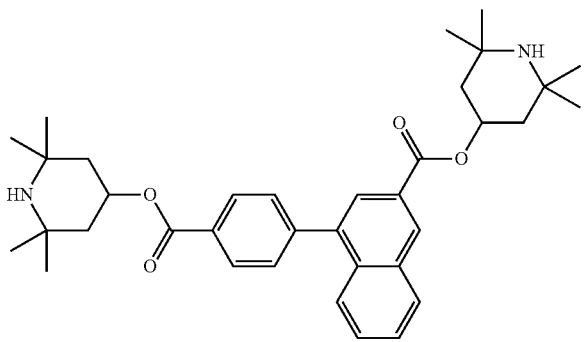
180
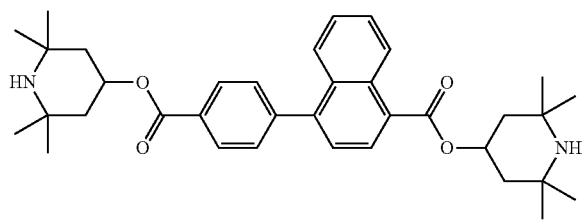
181
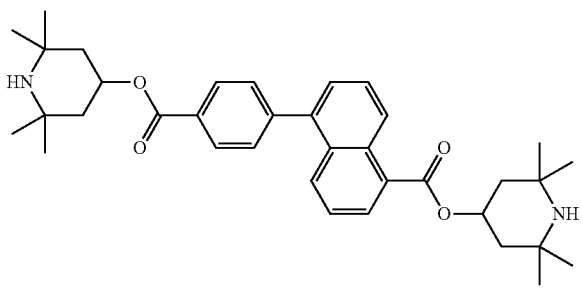
182
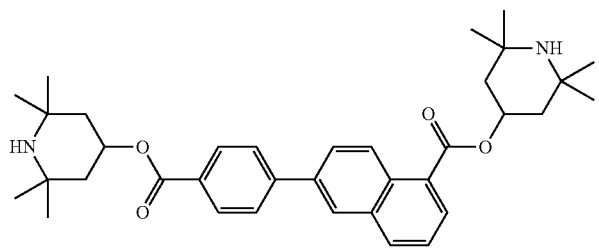
183
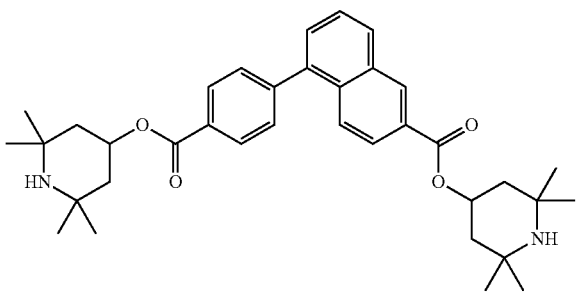
184
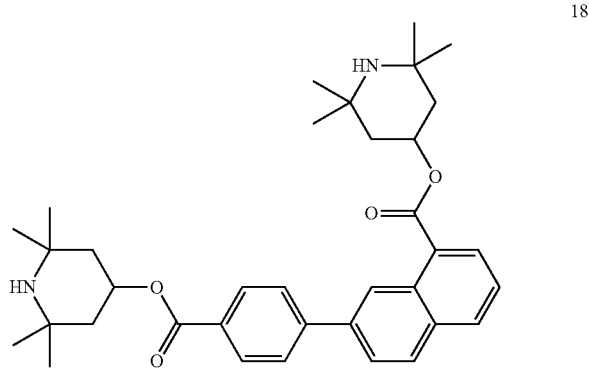
185

-continued
186
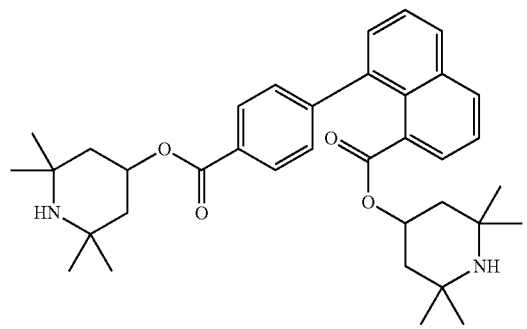
187
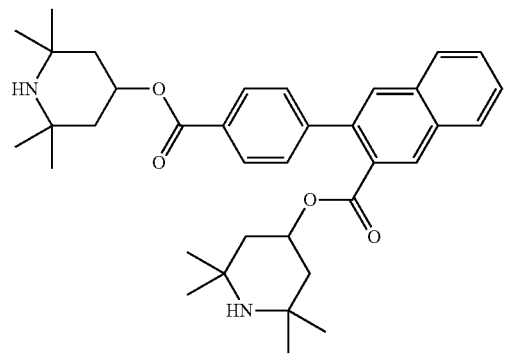
188
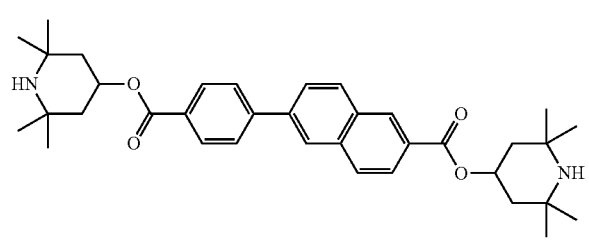
189
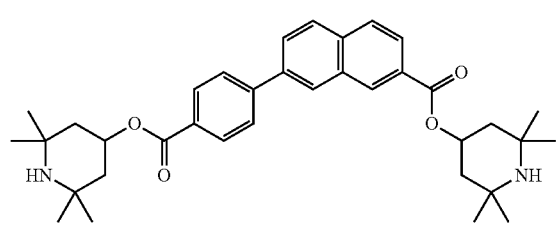
190
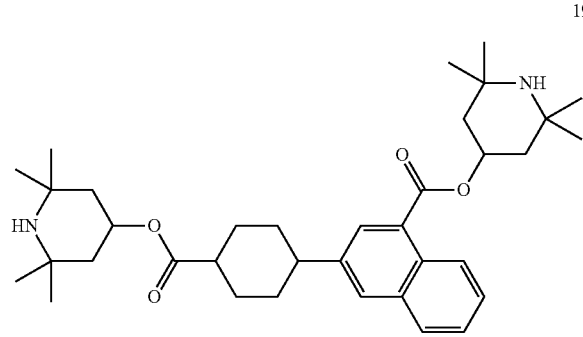
191
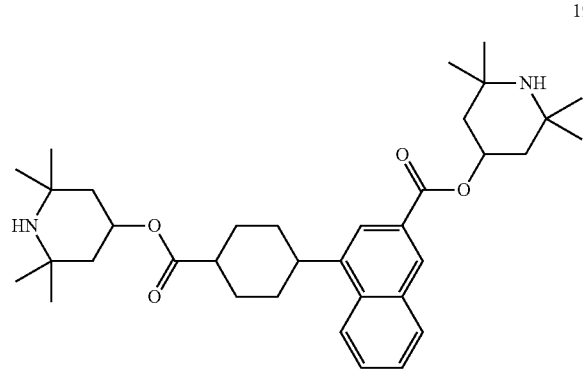
192
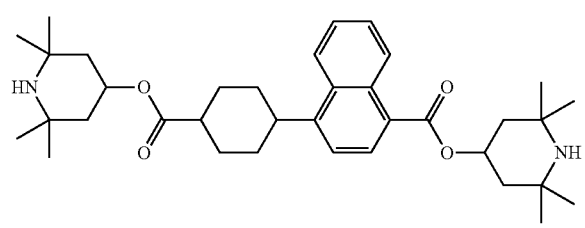
193
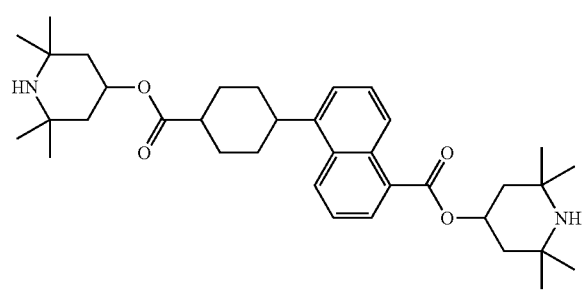
194
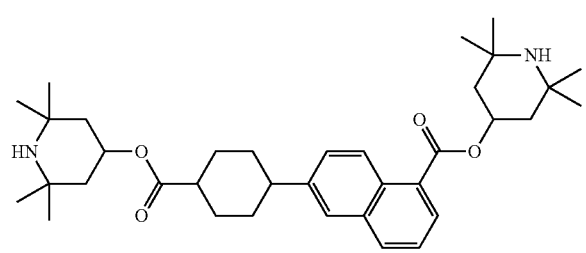
195
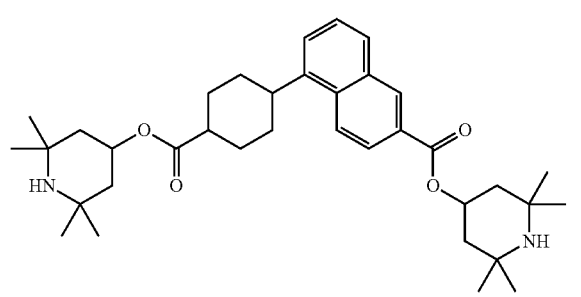

196 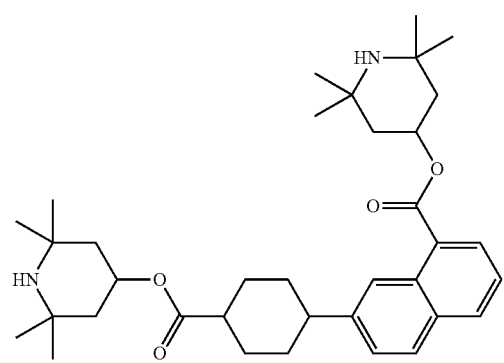
197 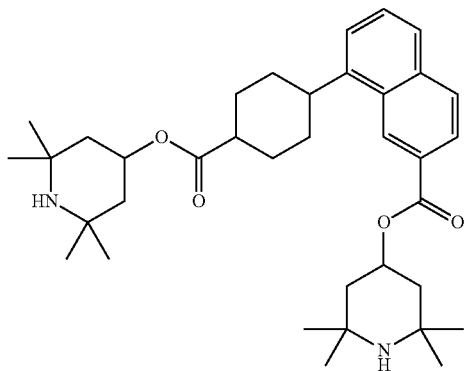
198 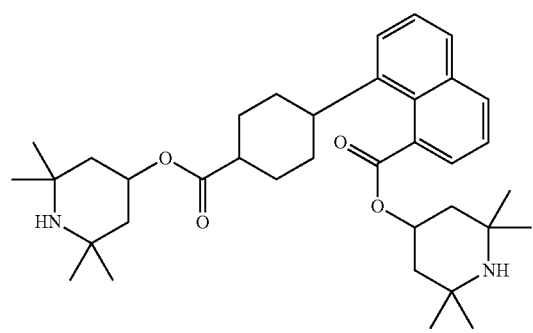
199 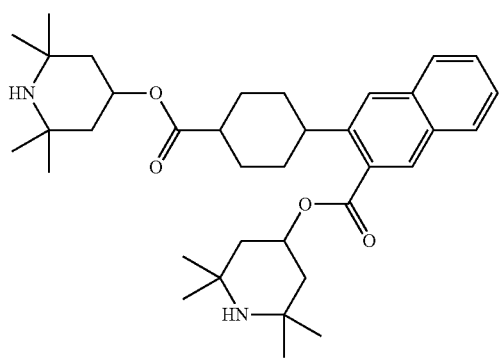
200 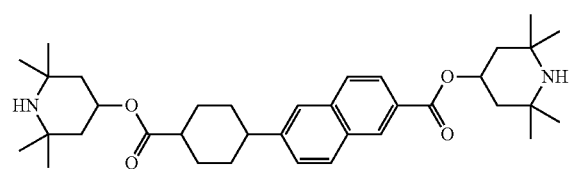
201 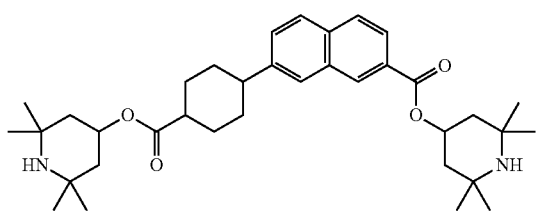
202 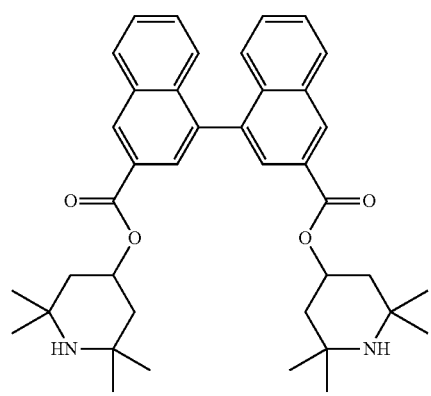
203 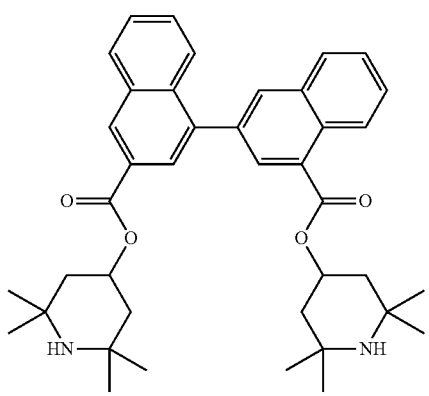

204
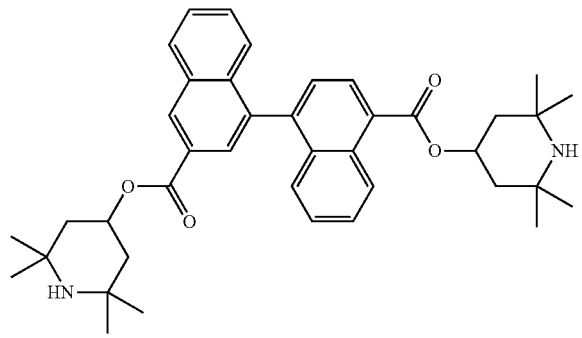
205
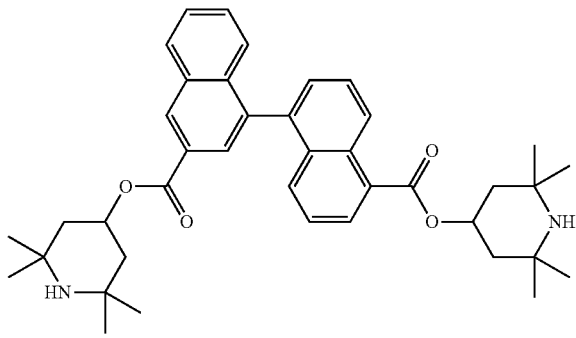
206
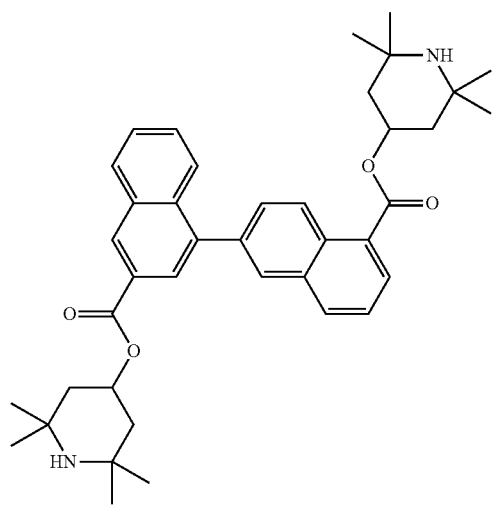
207
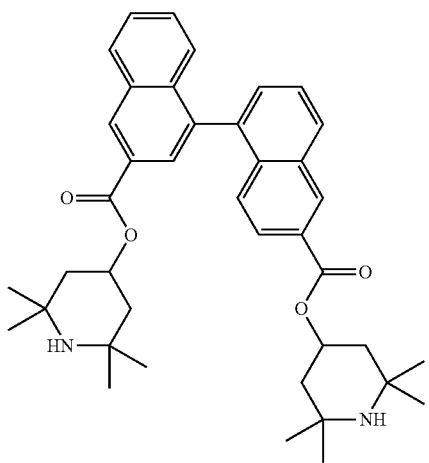
208
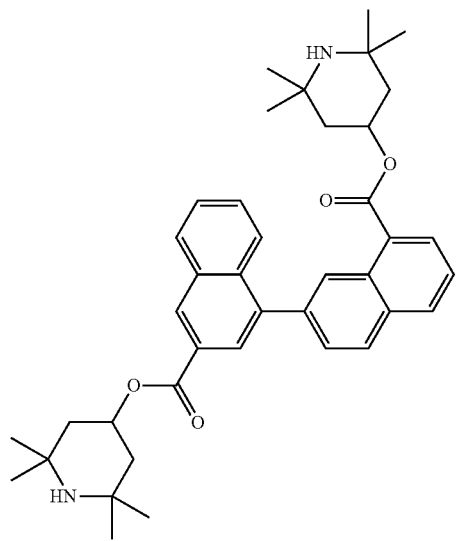
209
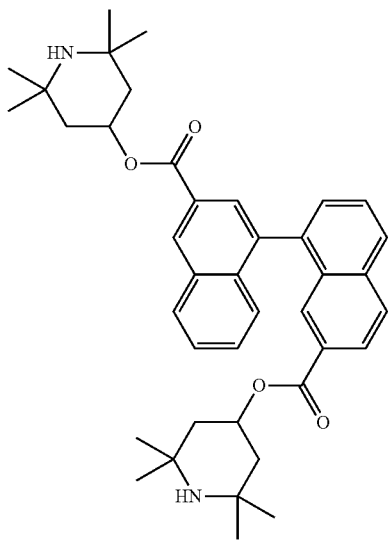

210 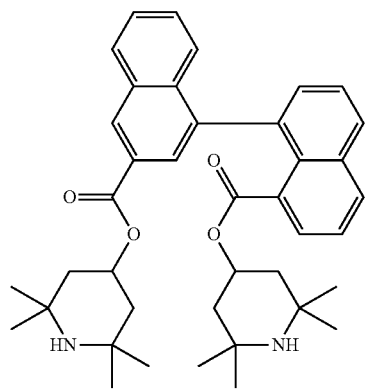
211 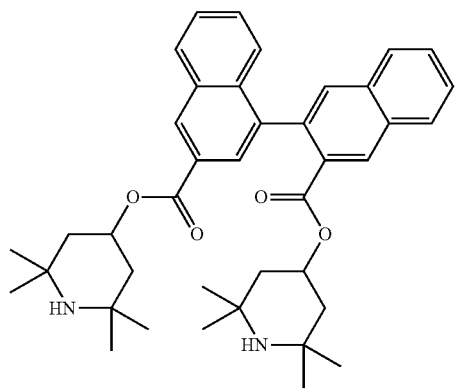
212 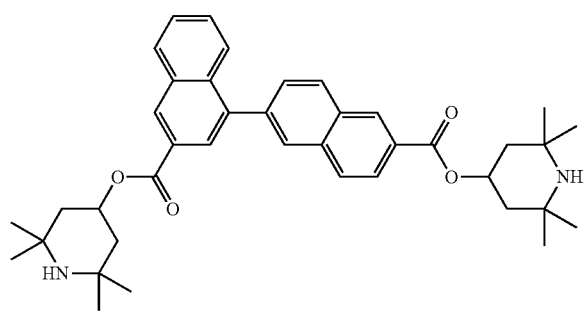
213 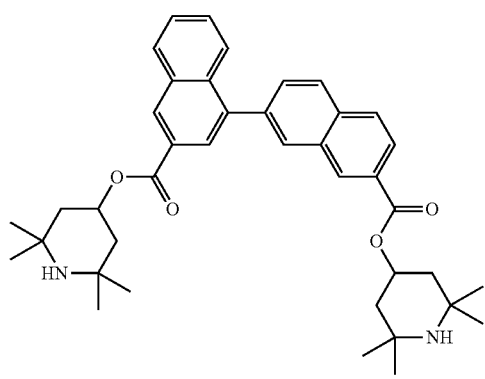
214 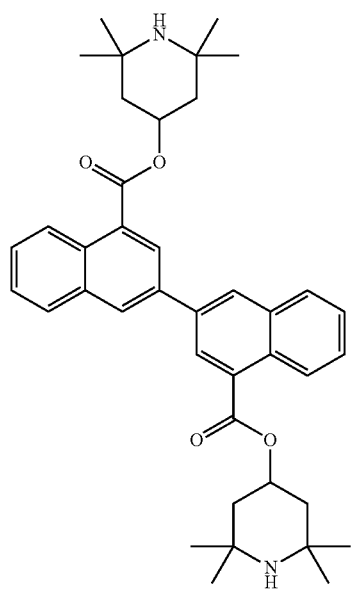
215 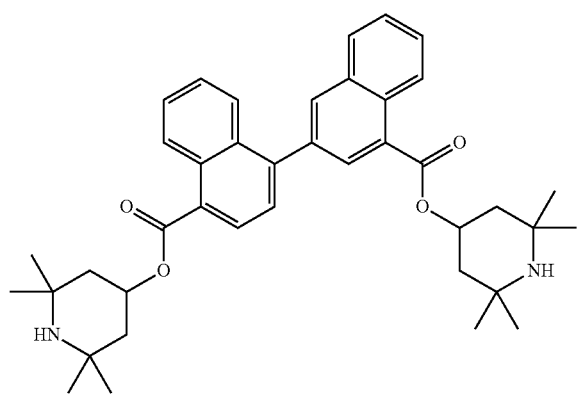

-continued
216 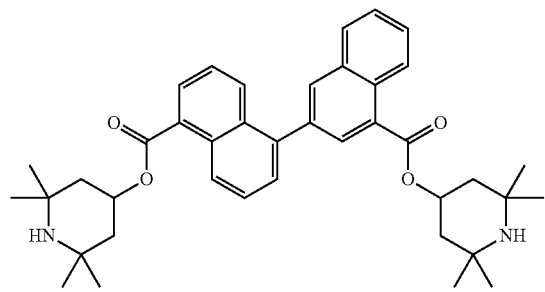
217 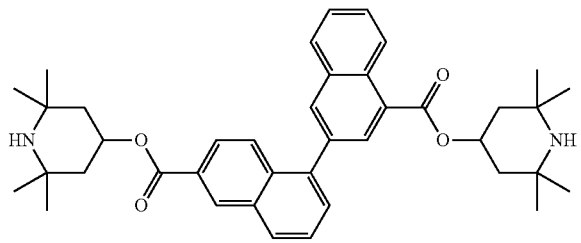
218 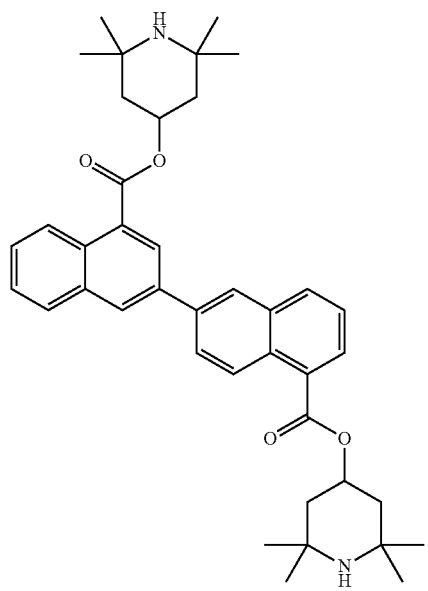
219 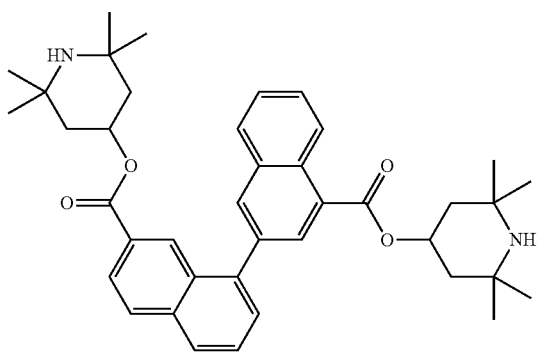
220 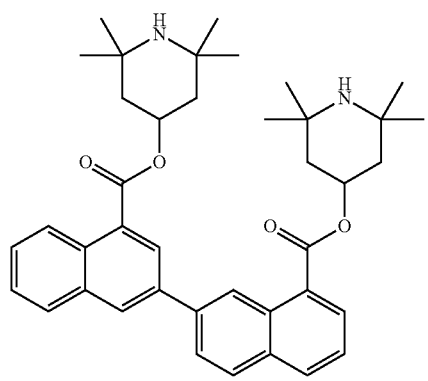
221 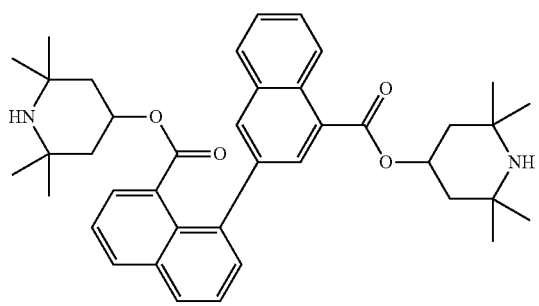

-continued
222
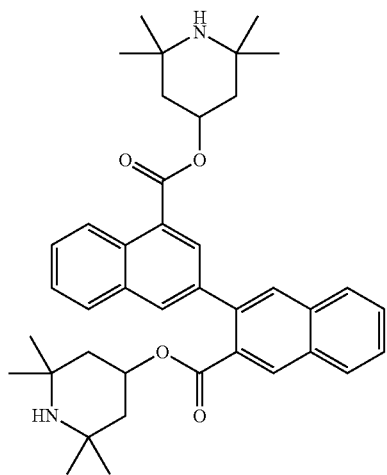
223
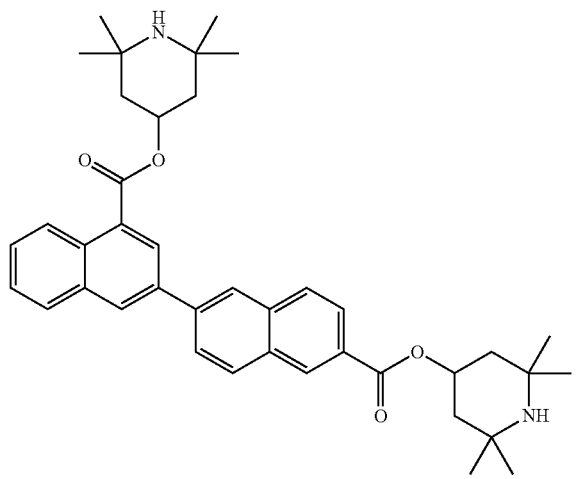
224
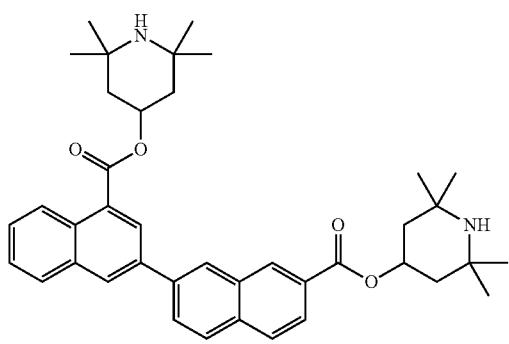
225
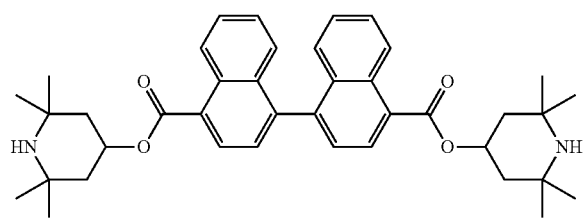
226
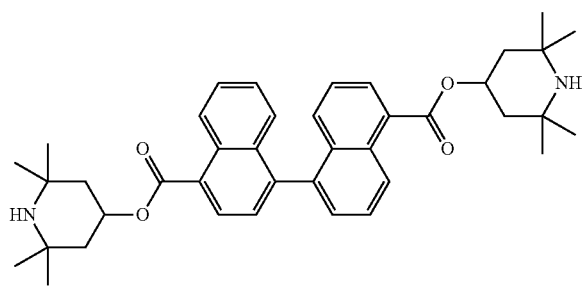
227
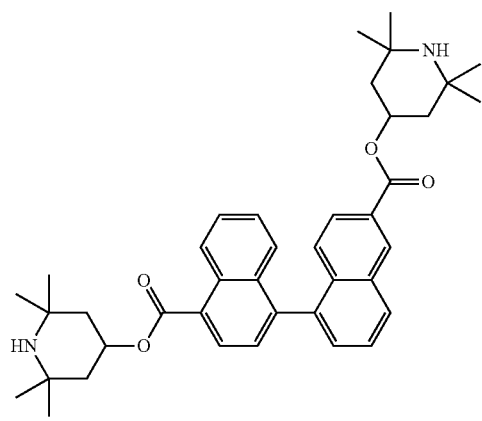

-continued
228 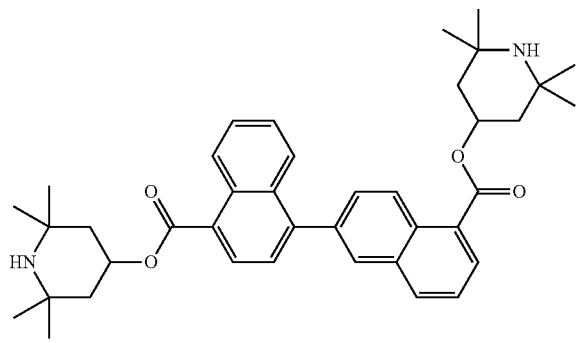
229 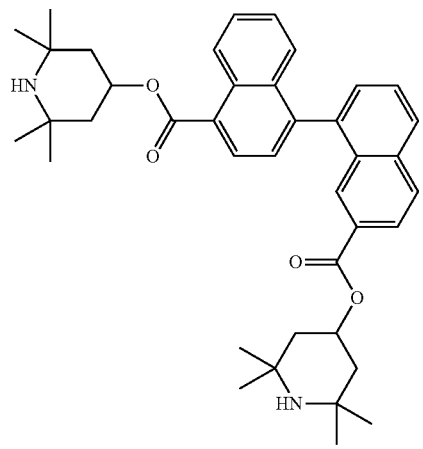
230 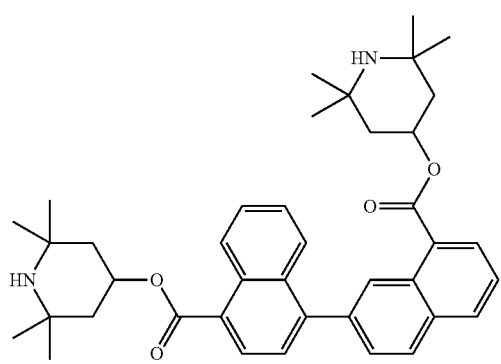
231 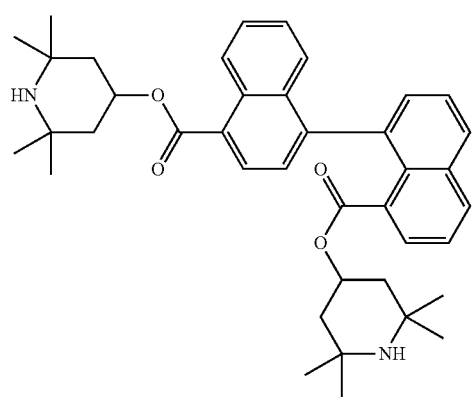
232 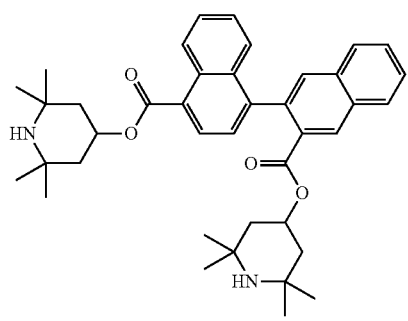
233 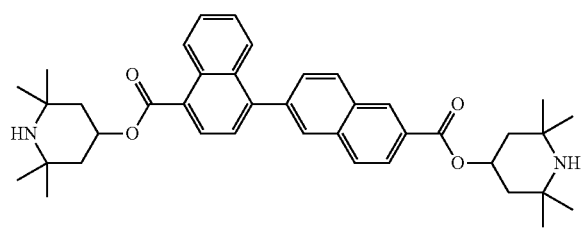
234 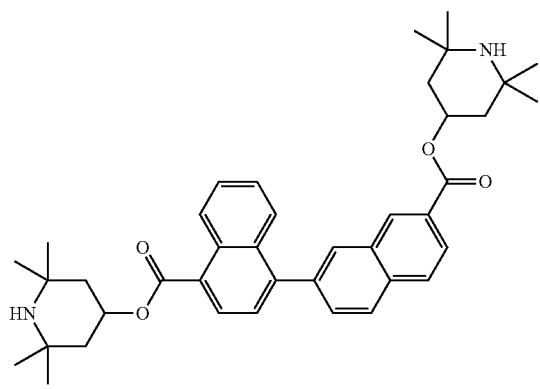
235 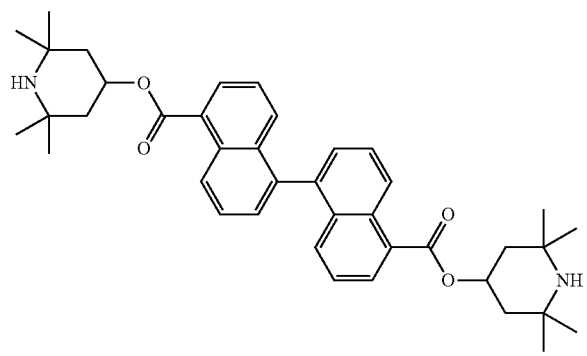

-continued
| 236 | 237 |
|---|---|
| 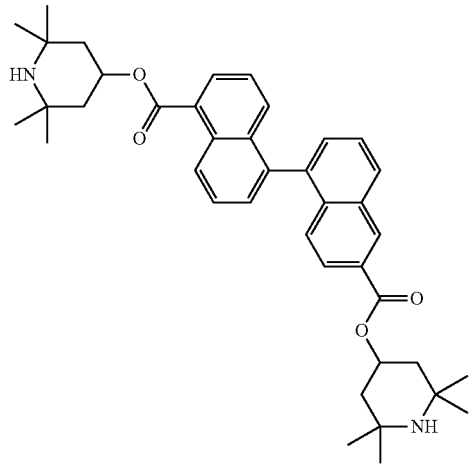 | 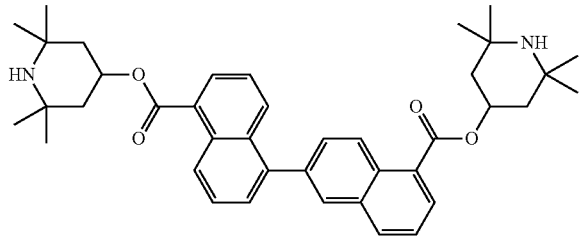 |
| 238 | 239 |
| 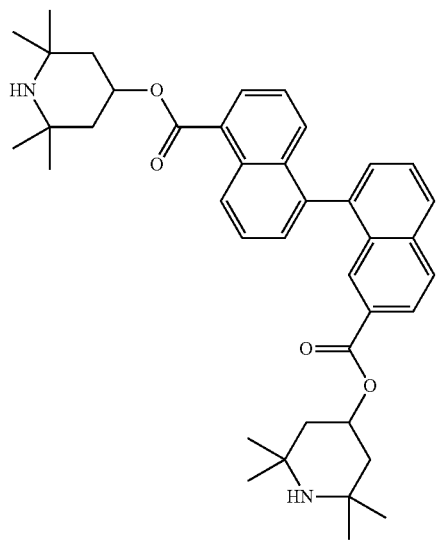 | 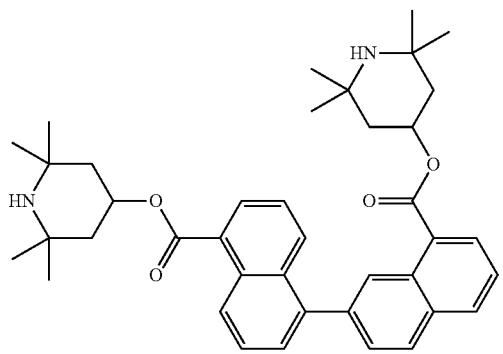 |
| 240 | 241 |
| 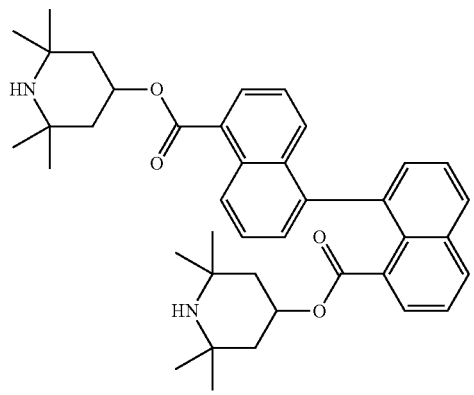 | 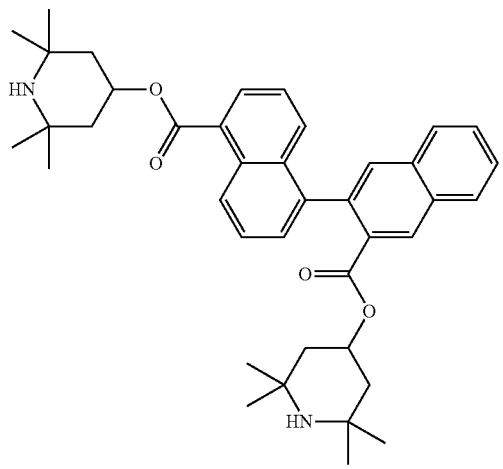 |

242
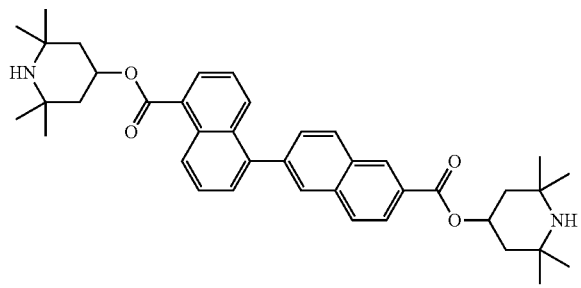
243
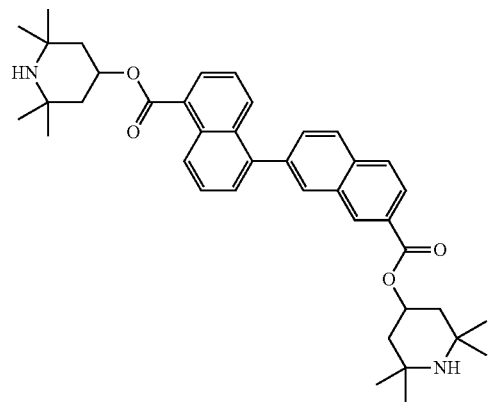
244
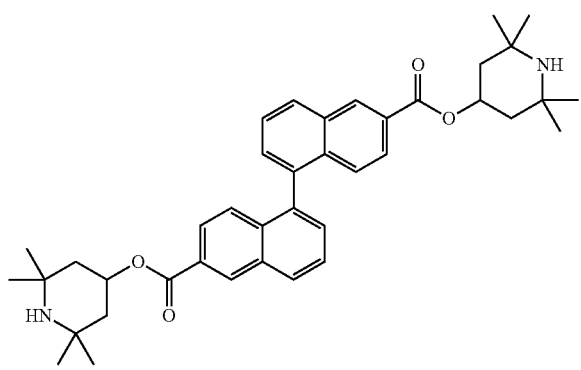
245
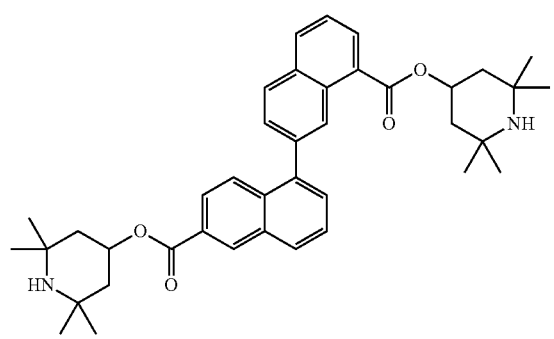
246
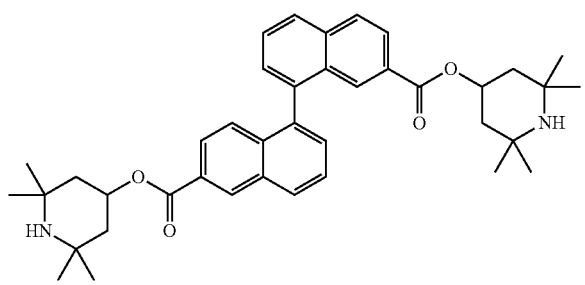
247
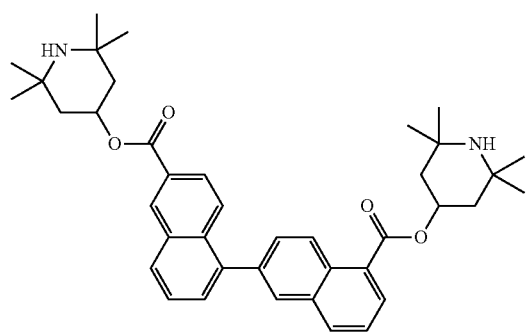
248
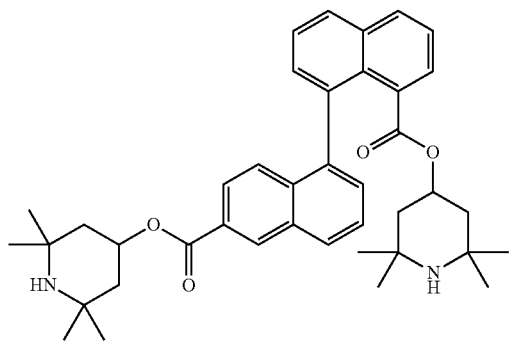
249
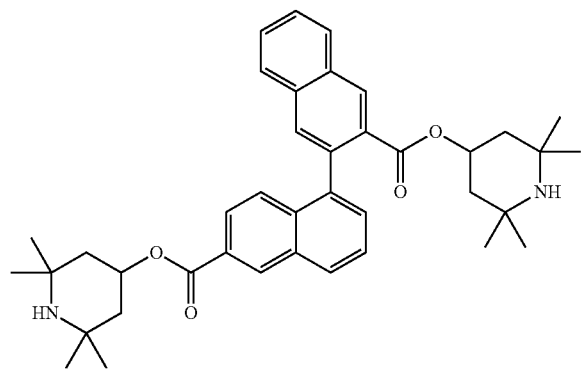

-continued
250
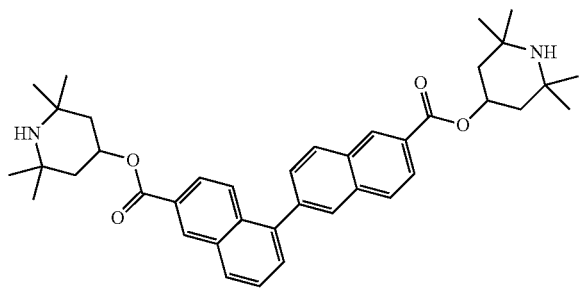
251
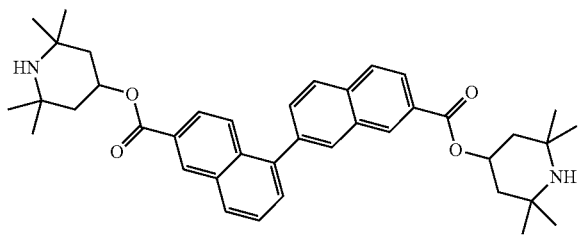
252
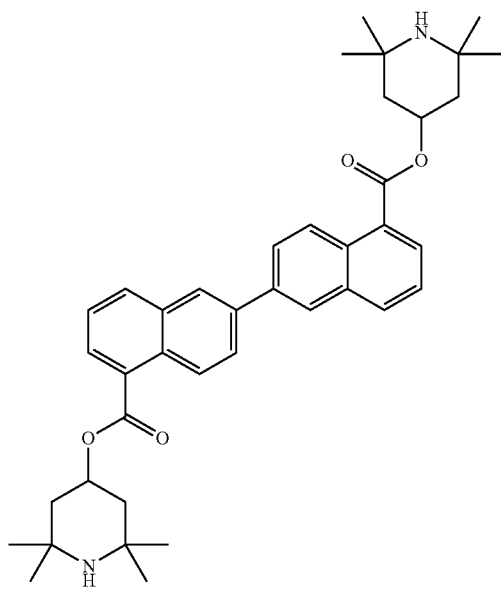
253
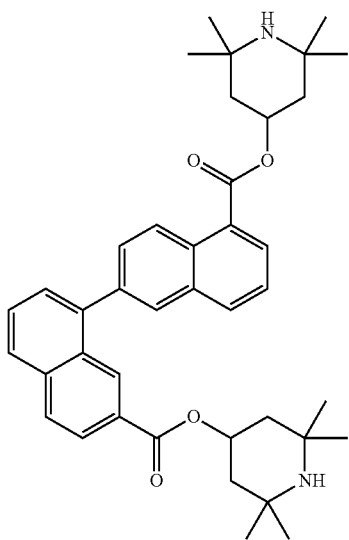
254
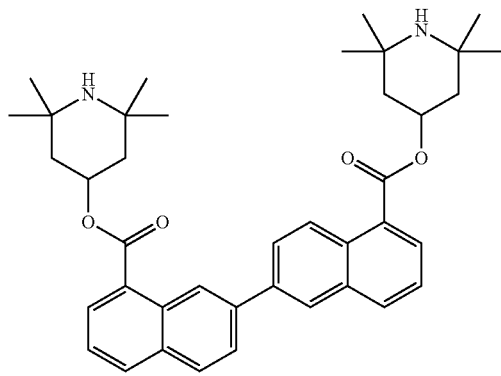
255
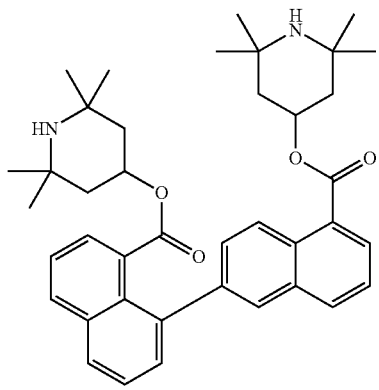

-continued
256
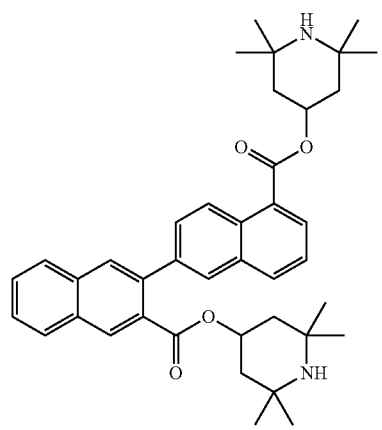
257
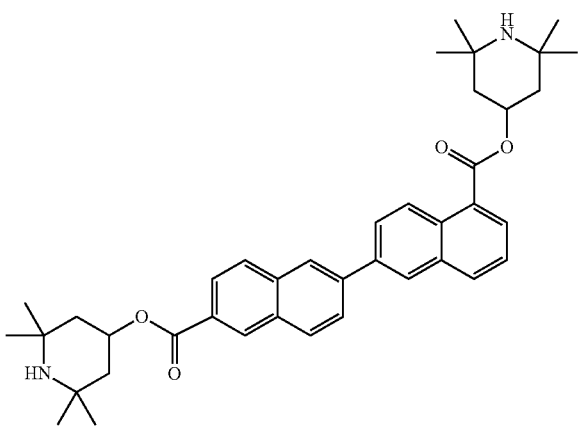
258
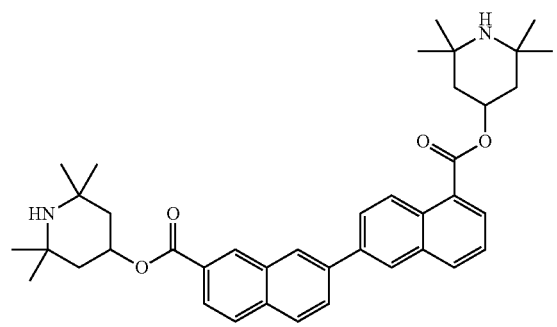
259
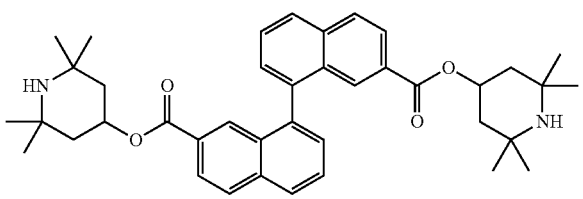
260
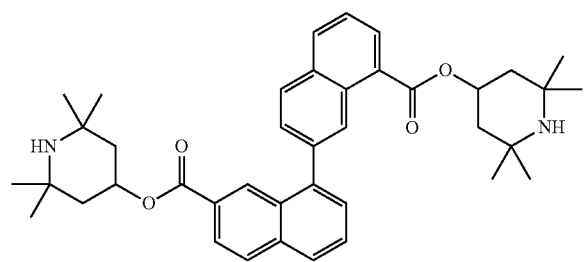
261
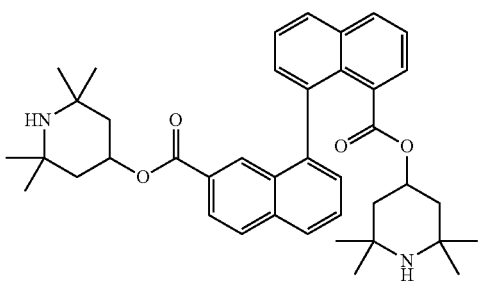
262
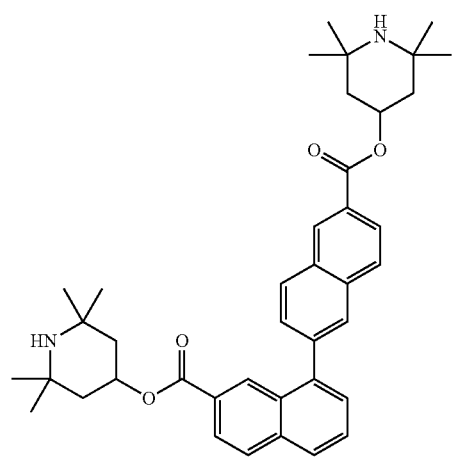
263
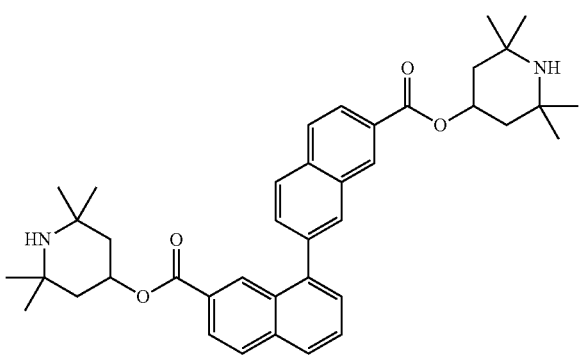

-continued
264
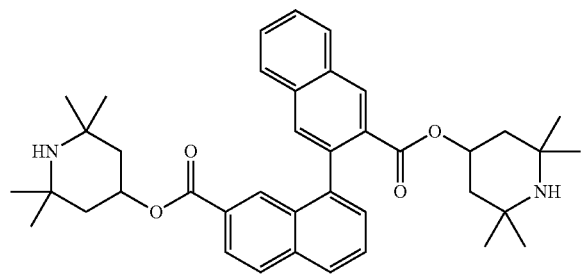
265
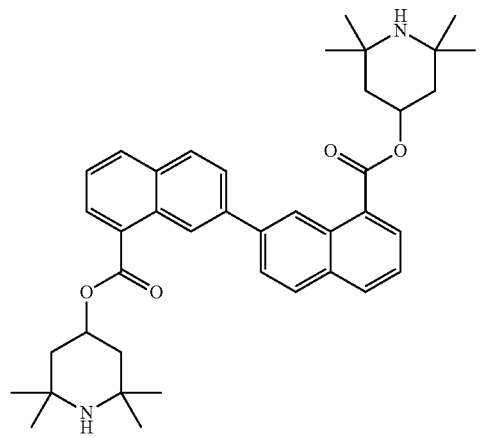
266
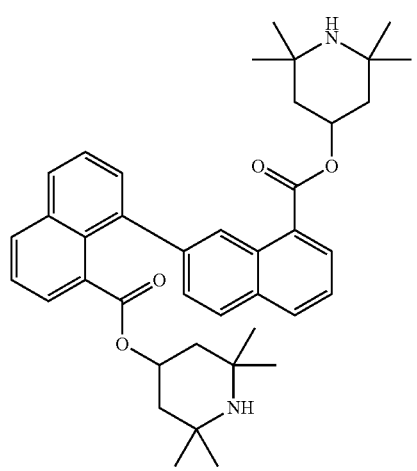
267
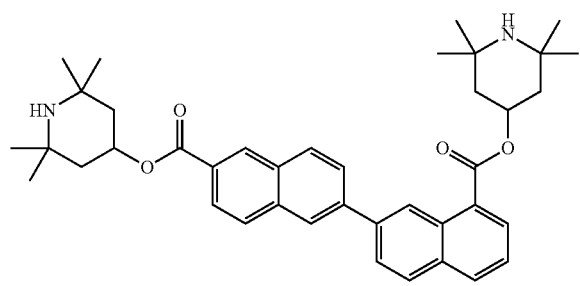
268
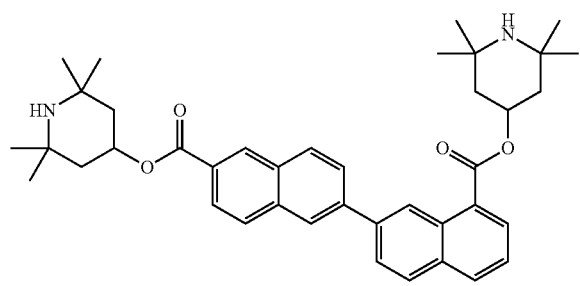
269
270
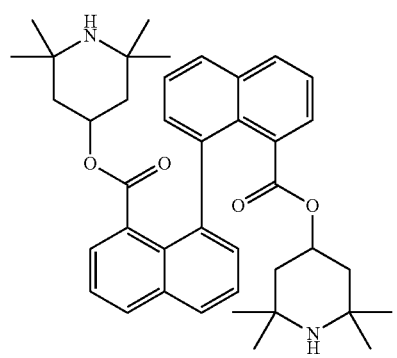
271
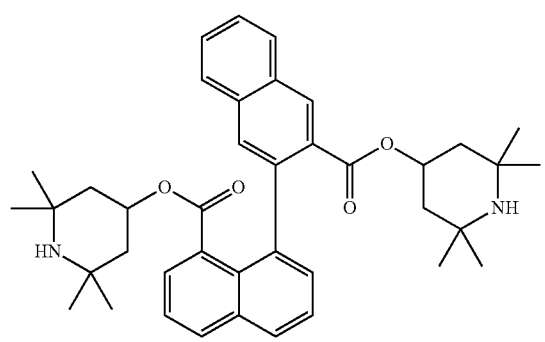

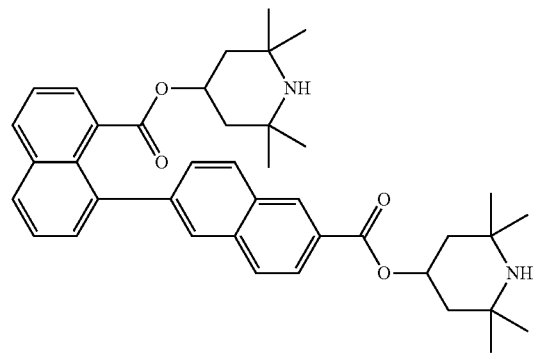 272
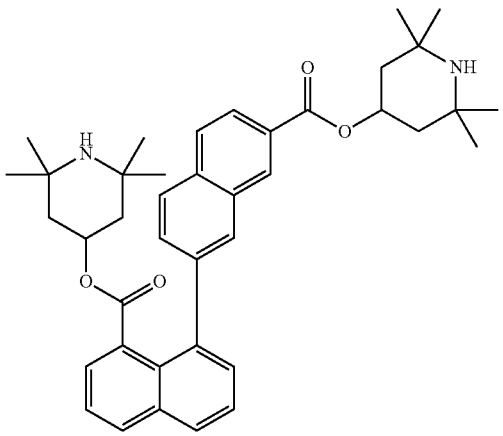 273
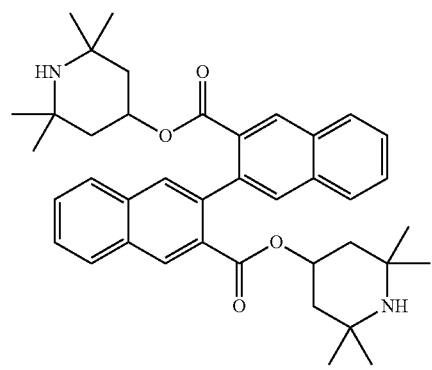 274
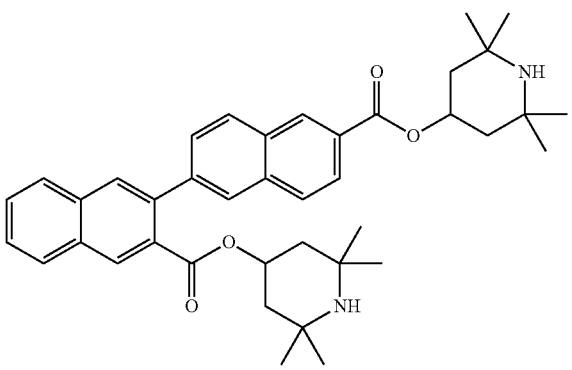 275
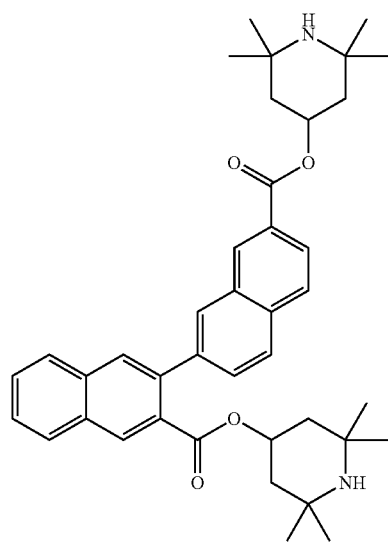 276

277
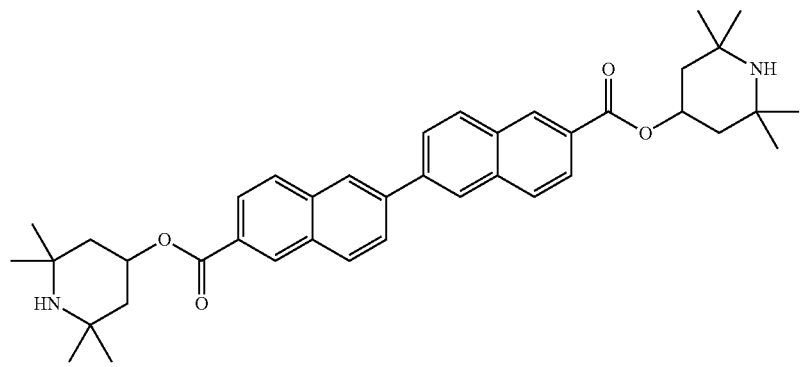
278
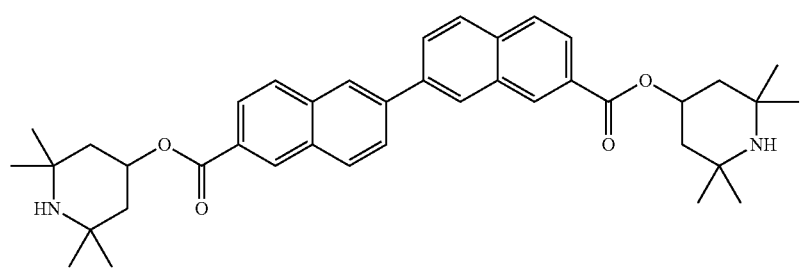
279
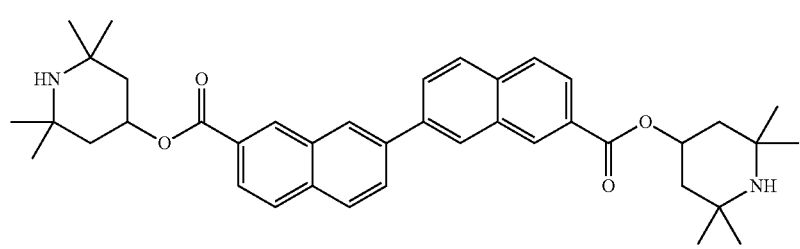
280
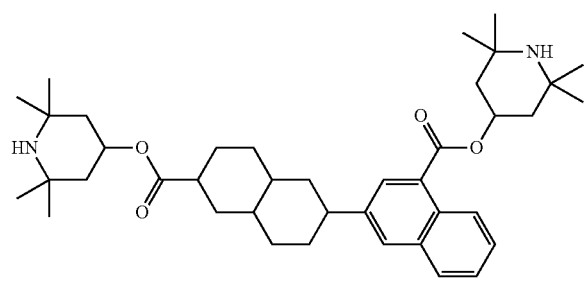
281
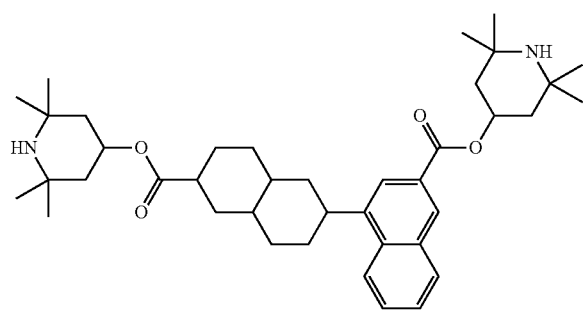
282
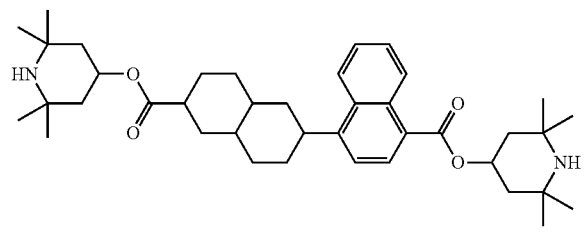
283
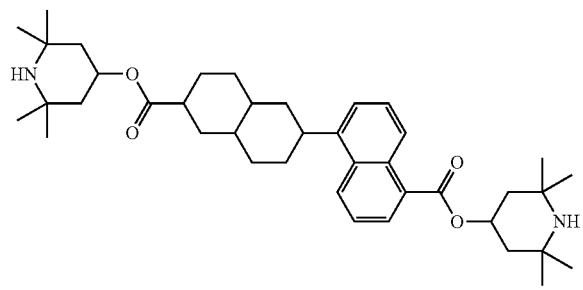

284
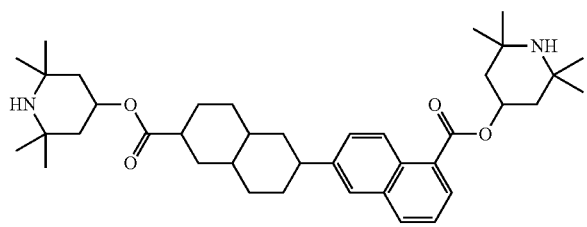
285
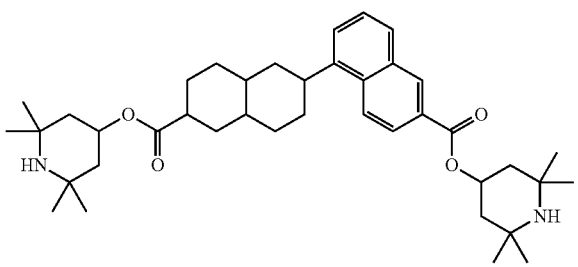
286
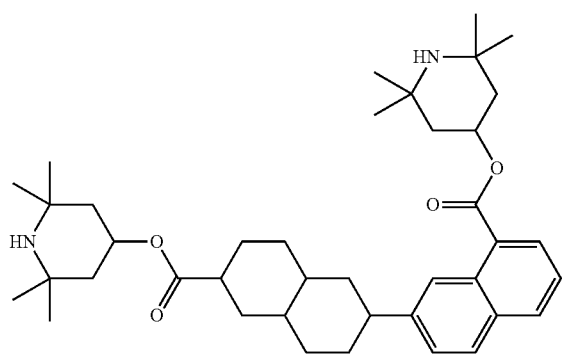
287
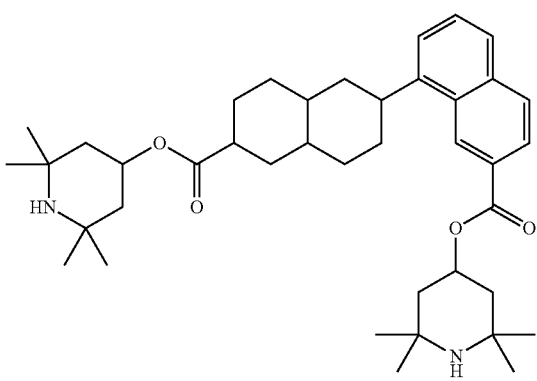
288
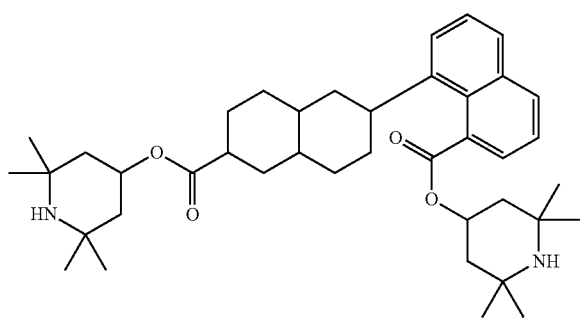
289
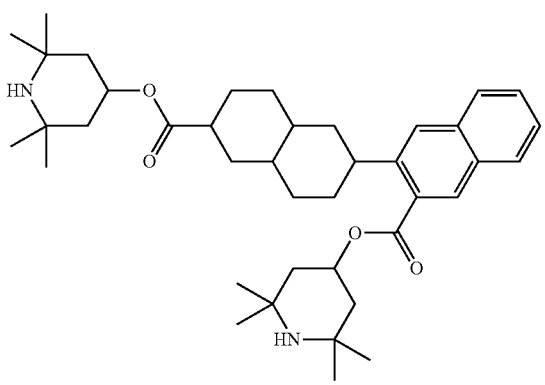
290
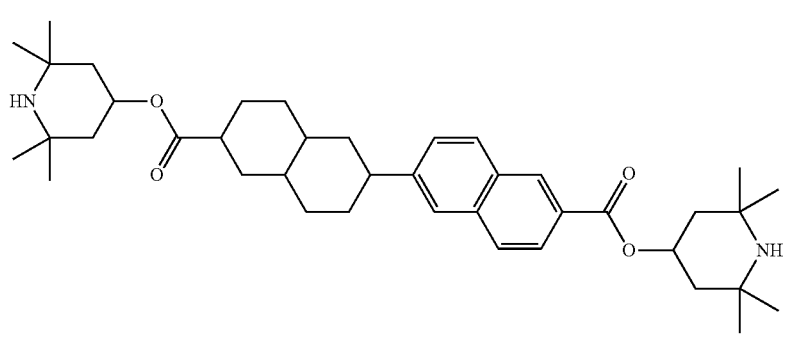

-continued

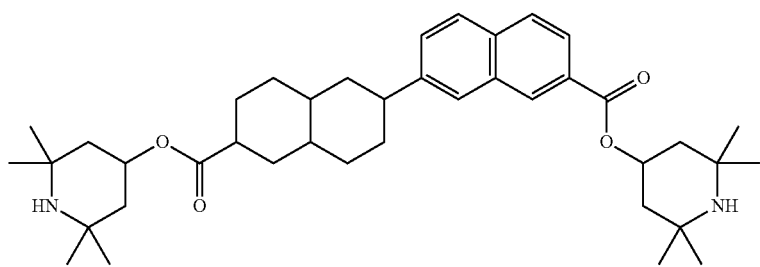

2. Example of Liquid Crystal Composition

The compounds in Examples were described using symbols according to the definitions in Table 3 below. In Table 3, a configuration of 1,4-cyclohexylene is trans. A parenthesized number next to a symbolized compound in Examples corresponds to the number of a compound. A symbol (-) means any other liquid crystal compound. A ratio (percentage) of a liquid crystal compound is expressed in terms of weight percent (% by weight) based on the weight of the liquid crystal composition. Values of characteristics of the liquid crystal composition were summarized in a last part. The characteristics were measured according to the methods described above, and measured values were directly described (without extrapolation).

TABLE 3

Method for Description of Compounds using Symbols
R—(A$_1$)—Z$_1$— . . . —Z$_n$—(A$_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right-terminal Group —R' | Symbol |
|---|---|
| —$C_nH_{2n+1}$ | -n |
| —$OC_nH_{2n+1}$ | —On |
| —COOCH$_3$ | —EMe |
| —CH=CH$_2$ | —V |
| —CH=CH—$C_nH_{2n+1}$ | —Vn |
| —$C_nH_{2n}$—CH=CH$_2$ | —nV |
| —$C_mH_{2m}$—CH=CH—$C_nH_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |

| 3) Bonding Group —Z$_n$— | Symbol |
|---|---|
| —$C_nH_{2n}$— | n |
| —COO— | E |
| —CH=CH— | V |
| —CH$_2$O— | 1O |
| —OCH$_2$— | O1 |
| —CF$_2$O— | X |
| —C≡C— | T |

| 4) Ring Structure —A$_n$— | Symbol |
|---|---|
| ⬡ | H |

TABLE 3-continued
Method for Description of Compounds using Symbols
R—(A$_1$)—Z$_1$— . . . —Z$_n$—(A$_n$)—R'
| | |
|---|---|
| 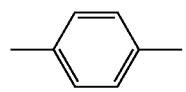 | B |
| 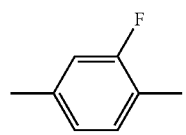 | B(F) |
| 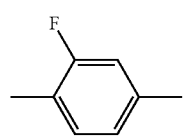 | B(2F) |
| 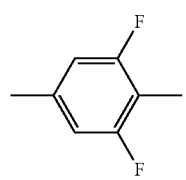 | B(F,F) |
| 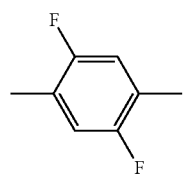 | B(2F,5F) |
| 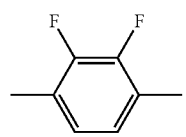 | B(2F,3F) |
| 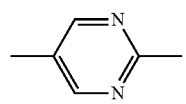 | Py |
| 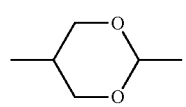 | G |
| 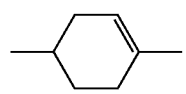 | ch |
5) Examples of Description
Example 1  3-HB—CL
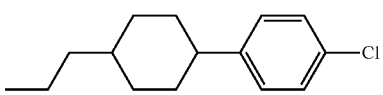

TABLE 3-continued

Method for Description of Compounds using Symbols
R—(A₁)—Z₁— . . . —Zₙ—(Aₙ)—R'

Example 2 5-HHBB(F,F)—F

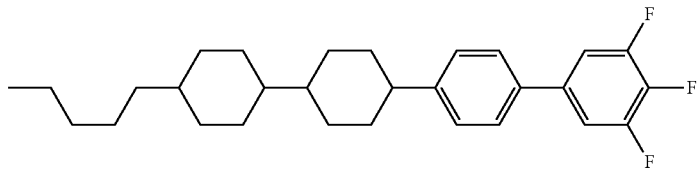 [SMILES: CCCCCC1CCC(C2CCC(c3ccc(-c4cc(F)c(F)c(F)c4)cc3)CC2)CC1]

Example 3 3-HB—O2

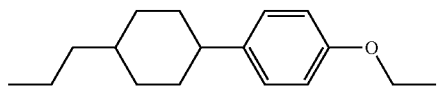

Example 4 3-HBB(F,F)—F

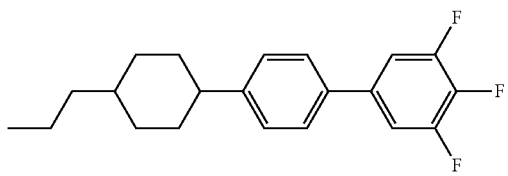 [SMILES: CCCC1CCC(c2ccc(-c3cc(F)c(F)c(F)c3)cc2)CC1]

Example 1

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 11% |
| 4-PyBB-F | (6-80) | 11% |
| 5-PyBB-F | (6-80) | 11% |
| 5-HBB(F)B-2 | (4-5) | 8% |
| 5-HBB(F)B-3 | (4-5) | 9% |

To the composition described above, compound (No. 85) below was added at a ratio of 0.15% by weight.

(No.85)

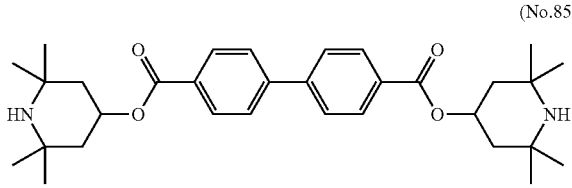

NI=96.6° C.; η=39.4 mPa·s; Δn=0.190; Δ∈=8.4.

Example 2

| | | |
|---|---|---|
| 2-HB-C | (8-1) | 7% |
| 3-HB-C | (8-1) | 12% |
| 3-HB-O2 | (2-5) | 13% |
| 2-BTB-1 | (2-10) | 3% |
| 3-HHB-F | (6-1) | 4% |
| 3-HHB-1 | (3-1) | 8% |

-continued

| | | |
|---|---|---|
| 3-HHB-O1 | (3-1) | 5% |
| 3-HHB-3 | (3-1) | 13% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |

To the composition described above, compound (No. 8) below was added at a ratio of 0.1% by weight.

(No.8)

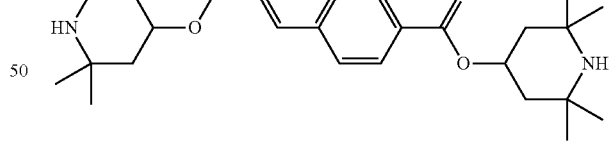

NI=99.4° C.; η=18.6 mPa·s; Δn=0.100; Δ∈=4.9.

Example 3

| | | |
|---|---|---|
| 7-HB(F,F)-F | (5-4) | 3% |
| 3-HB-O2 | (2-5) | 7% |
| 2-HHB(F)-F | (6-2) | 9% |
| 3-HHB(F)-F | (6-2) | 9% |
| 5-HHB(F)-F | (6-2) | 9% |
| 2-HBB(F)-F | (6-23) | 10% |
| 3-HBB(F)-F | (6-23) | 10% |
| 5-HBB(F)-F | (6-23) | 16% |

| | | |
|---|---|---|
| 2-HBB-F | (6-22) | 4% |
| 3-HBB-F | (6-22) | 4% |
| 5-HBB-F | (6-22) | 4% |
| 3-HBB(F,F)-F | (6-24) | 5% |
| 5-HBB(F,F)-F | (6-24) | 10% |

To the composition described above, compound (No. 105) below was added at a ratio of 0.05% by weight.

(No.105)

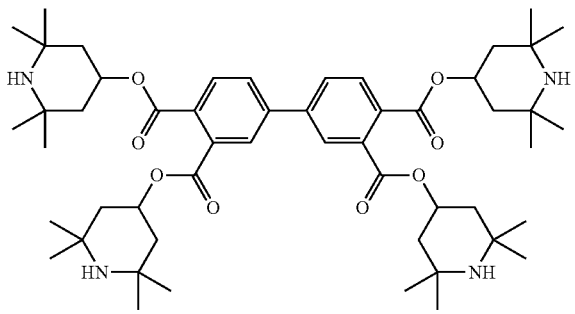

NI=84.9° C.; η=25.1 mPa·s; Δn=0.117; Δ∈=5.8.

Example 4

| | | |
|---|---|---|
| 3-HHB(F,F)-F | (6-3) | 9% |
| 3-H2HB(F,F)-F | (6-15) | 7% |
| 4-H2HB(F,F)-F | (6-15) | 8% |
| 5-H2HB(F,F)-F | (6-15) | 9% |
| 3-HBB(F,F)-F | (6-24) | 21% |
| 5-HBB(F,F)-F | (6-24) | 20% |
| 3-H2BB(F,F)-F | (6-27) | 9% |
| 5-HHBB(F,F)-F | (7-6) | 3% |
| 5-HHEBB-F | (7-17) | 2% |
| 3-HH2BB(F,F)-F | (7-15) | 4% |
| 1O1-HBBH-4 | (4-1) | 4% |
| 1O1-HBBH-5 | (4-1) | 4% |

To the composition described above, compound (No. 225) below was added at a ratio of 0.05% by weight.

(No.225)

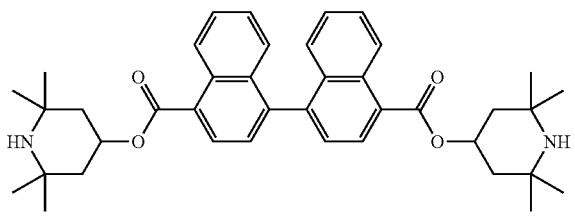

NI=99.5° C.; η=35.3 mPa·s; Δn=0.117; Δ∈=9.0.

Example 5

| | | |
|---|---|---|
| 5-HB-F | (5-2) | 12% |
| 6-HB-F | (5-2) | 9% |
| 7-HB-F | (5-2) | 7% |

| | | |
|---|---|---|
| 2-HHB-OCF3 | (6-1) | 6% |
| 3-HHB-OCF3 | (6-1) | 8% |
| 4-HHB-OCF3 | (6-1) | 7% |
| 5-HHB-OCF3 | (6-1) | 5% |
| 3-HH2B-OCF3 | (6-4) | 5% |
| 5-HH2B-OCF3 | (6-4) | 4% |
| 3-HHB(F,F)-OCF2H | (6-3) | 3% |
| 3-HHB(F,F)-OCF3 | (6-3) | 5% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |

To the composition described above, compound (No. 86) below was added at a ratio of 0.15% by weight.

(No.86)

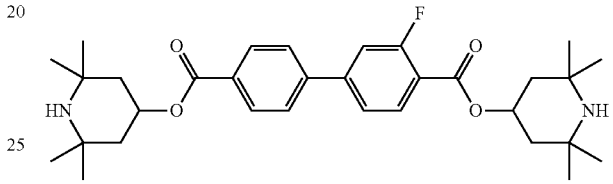

NI=85.8° C.; η=14.6 mPa·s; Δn=0.092; Δ∈=4.4.

Example 6

| | | |
|---|---|---|
| 3-HB-CL | (5-2) | 4% |
| 5-HB-CL | (5-2) | 4% |
| 3-HHB-OCF3 | (6-1) | 5% |
| 3-H2HB-OCF3 | (6-13) | 5% |
| 5-H4HB-OCF3 | (6-19) | 15% |
| V-HHB(F)-F | (6-2) | 5% |
| 3-HHB(F)-F | (6-2) | 5% |
| 5-HHB(F)-F | (6-2) | 7% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 10% |
| 3-HBEB(F,F)-F | (6-39) | 5% |

To the composition described above, compound (No. 85) below was added at a ratio of 0.1% by weight.

(No.85)

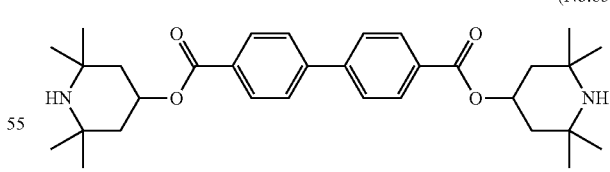

NI=72.4° C.; η=26.0 mPa·s; Δn=0.097; Δ∈=8.3.

Example 7

| | | |
|---|---|---|
| 5-HB-CL | (5-2) | 5% |
| 7-HB(F)-F | (5-3) | 7% |
| 3-HB-O2 | (2-5) | 7% |
| 3-HH-EMe | (2-2) | 23% |

| | | |
|---|---|---|
| 3-HHEB-F | (6-10) | 8% |
| 5-HHEB-F | (6-10) | 7% |
| 3-HHEB(F,F)-F | (6-12) | 10% |
| 4-HHEB(F,F)-F | (6-12) | 5% |
| 4-HGB(F,F)-F | (6-103) | 6% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 7% |

To the composition described above, compound (No. 8) below was added at a ratio of 0.15% by weight.

(No.8)

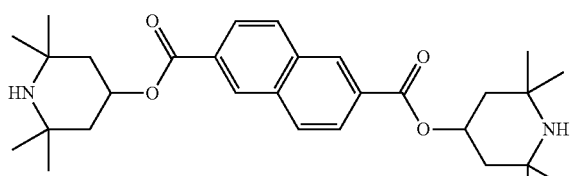

NI=75.1° C.; η=20.2 mPa·s; Δn=0.068; Δ∈=5.9.

Example 8

| | | |
|---|---|---|
| 3-HB-O2 | (2-5) | 12% |
| 5-HB-CL | (5-2) | 13% |
| 3-HBB(F,F)-F | (6-24) | 5% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 8% |
| 5-PyBB-F | (6-80) | 10% |
| 5-HBB(F)B-2 | (4-5) | 11% |
| 5-HBB(F)B-3 | (4-5) | 11% |

To the composition described above, compound (No. 105) below was added at a ratio of 0.1% by weight.

(No.105)

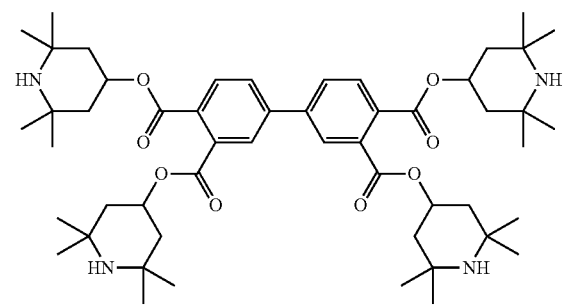

NI=100.6° C.; η=38.9 mPa·s; Δn=0.190; Δ∈=7.6.

Example 9

| | | |
|---|---|---|
| 2-HB-C | (8-1) | 5% |
| 3-HB-C | (8-1) | 12% |
| 3-HB-O2 | (2-5) | 15% |
| 2-BTB-1 | (2-10) | 4% |
| 3-HHB-F | (6-1) | 4% |
| 3-HHB-1 | (3-1) | 8% |
| 3-HHB-O1 | (3-1) | 6% |
| 3-HHB-3 | (3-1) | 14% |
| 3-HHEB-F | (6-10) | 4% |
| 5-HHEB-F | (6-10) | 4% |
| 2-HHB(F)-F | (6-2) | 6% |
| 3-HHB(F)-F | (6-2) | 6% |
| 5-HHB(F)-F | (6-2) | 6% |
| 3-HHB(F,F)-F | (6-3) | 6% |

To the composition described above, compound (No. 225) below was added at a ratio of 0.1% by weight.

(No.225)

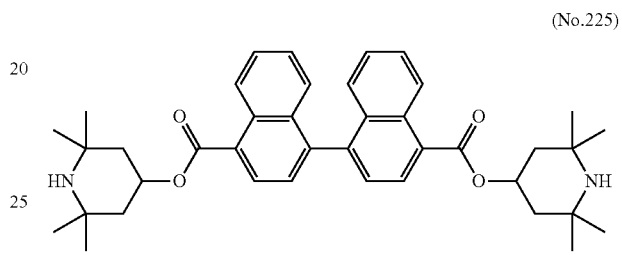

NI=100.3° C.; η=17.6 mPa·s; Δn=0.102; Δ∈=4.6.

Example 10

| | | |
|---|---|---|
| 7-HB(F,F)-F | (5-4) | 5% |
| 3-HB-O2 | (2-5) | 5% |
| 2-HHB(F)-F | (6-2) | 9% |
| 3-HHB(F)-F | (6-2) | 10% |
| 5-HHB(F)-F | (6-2) | 9% |
| 2-HBB(F)-F | (6-23) | 10% |
| 3-HBB(F)-F | (6-23) | 10% |
| 5-HBB(F)-F | (6-23) | 16% |
| 2-HBB-F | (6-22) | 4% |
| 3-HBB-F | (6-22) | 4% |
| 5-HBB-F | (6-22) | 3% |
| 3-HBB(F,F)-F | (6-24) | 5% |
| 5-HBB(F,F)-F | (6-24) | 10% |

To the composition described above, compound (No. 86) below was added at a ratio of 0.05% by weight.

(No.86)

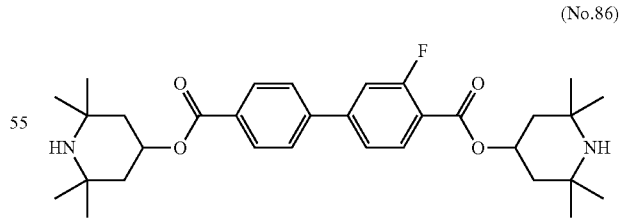

NI=82.9° C.; η=25.5 mPa·s; Δn=0.114; Δ∈=5.7.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

Compound (1) is effective in preventing photolysis of a liquid crystal composition, and has high solubility in the liquid crystal composition. The liquid crystal composition containing compound (1) is stable to light. A liquid crystal display device including the composition has characteristics such as a short response time, a large voltage holding ratio, a large contrast ratio and a long service life, and therefore can be used for a liquid crystal projector, a liquid crystal television and so forth.

What is claimed is:

1. A liquid crystal composition, containing at least one compound selected from the group of compounds represented by formula (1), and at least one compound represented by formulas (2) to (4):

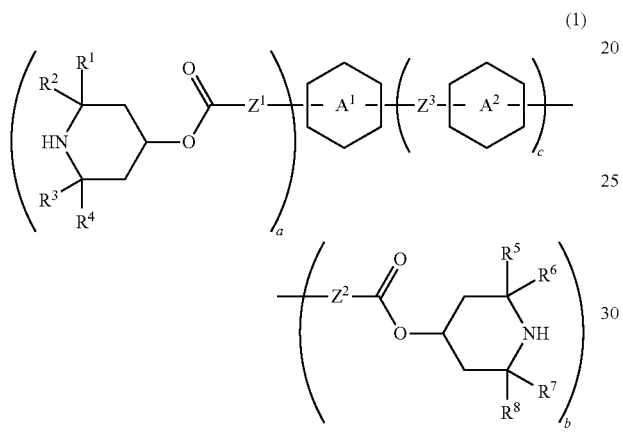

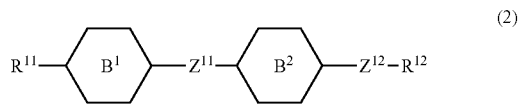

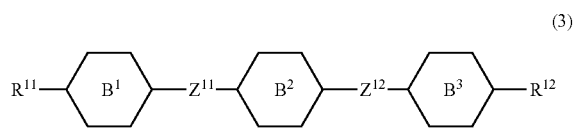

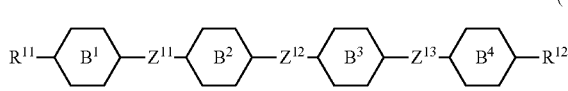

wherein, in formula (1),
R$^1$, R$^2$, R$^3$, R$^4$, R$^5$, R$^6$, R$^7$ and R$^8$ are independently hydrogen or alkyl having 1 to 4 carbons;
ring A$^1$ and ring A$^2$ are independently cyclohexylene, cyclohexenylene, decahydronaphthalenediyl, dihydropyrandiyl, tetrahydropyrandiyl, dioxanediyl, phenylene, naphthalenediyl, pyrimidinediyl or pyridinediyl, and in the rings, at least one of hydrogen may be replaced by halogen, alkyl having 1 to 5 carbons, alkoxy having 1 to 5 carbons, or alkyl having 1 to 5 carbons in which at least one of hydrogen is replaced by halogen;
Z$^1$, Z$^2$ and Z$^3$ are independently a single bond or alkylene having 1 to 10 carbons, and in the alkylene, at least one of —CH$_2$— may be replaced by —O—, —S—, —CO—, —COO—, —OCO— or —SiH$_2$—, at least one of —CH$_2$—CH$_2$— may be replaced by —CH=CH— or —C≡C—, and in the groups, at least one of hydrogen may be replaced by halogen; and a and b are independently 1 or 2, and c is 0, 1 or 2;

wherein, in formulas (2) to (4),
R$^{11}$ and R$^{12}$ are independently alkyl having 1 to 10 carbons or alkenyl having 2 to 10 carbons, and in the alkyl or the alkenyl, at least one of —CH$_2$— may be replaced by —O—, and at least one of hydrogen may be replaced by fluorine;
ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and
Z$^{11}$, Z$^{12}$ and Z$^{13}$ are independently a single bond, —CH$_2$CH$_2$—, —CH=CH—, —C≡C— or —COO—.

2. The liquid crystal composition according to claim 1, comprising:

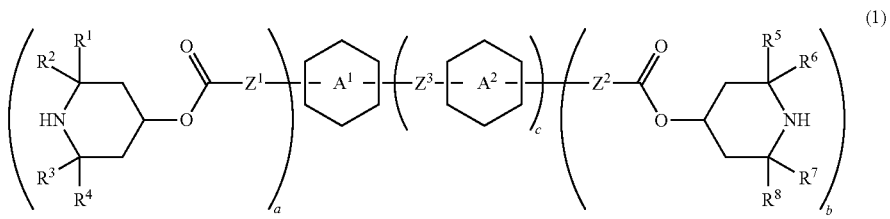

wherein, in formula (1),
R$^1$, R$^2$, R$^3$, R$^4$, R$^5$, R$^6$, R$^7$ and R$^8$ are independently alkyl having 1 to 4 carbons;
ring A$^1$ and ring A$^2$ are independently 1,4-cyclohexylene, 1,4-cyclohexenylene, decahydronaphthalene-2,6-diyl, 3,4-dihydro-2H-pyran-3,6-diyl, 3,4-dihydro-2H-pyran-2,5-diyl, 3,6-dihydro-2H-pyran-2,5-diyl, tetrahydropyran-2,5-diyl, 1,3-dioxane-2,5-diyl, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl, and in the rings, at least one of hydrogen may be replaced by fluorine, chlorine, alkyl having 1 to 5 carbons, alkoxy having 1 to 5 carbons, or alkyl having 1 to 5 carbons in which at least one of hydrogen is replaced by fluorine or chlorine;

$Z^1$, $Z^2$ and $Z^3$ are independently a single bond or alkylene having 1 to 10 carbons, and in the alkylene, at least one of —CH$_2$— may be replaced by —O—, —OCO— or —OCO—, at least one of —CH$_2$—CH$_2$— may be replaced by —CH=CH—, and in the groups, at least one of hydrogen may be replaced by fluorine or chlorine; and a and b are independently 1 or 2, and c is 0, 1 or 2.

3. The liquid crystal composition according to claim 1, comprising:

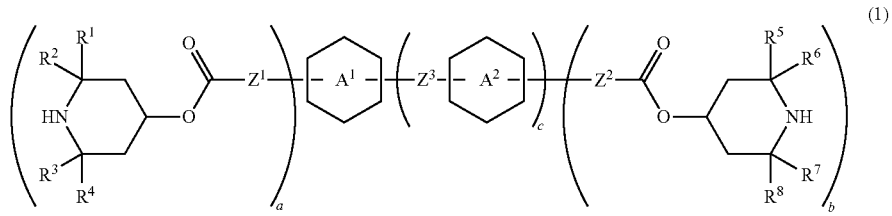

(1)

wherein, in formula (1),
$R^1$, $R^2$, $R^3$, $R^4$, $R^5$, $R^6$, $R^7$ and $R^8$ are independently alkyl having 1 to 4 carbons;
ring $A^1$ and ring $A^2$ are independently 1,4-cyclohexylene, 1,4-cyclohexenylene or decahydronaphthalene-2,6-diyl, and in the rings, at least one of hydrogen may be replaced by fluorine or chlorine;
$Z^1$, $Z^2$ and $Z^3$ are independently a single bond or alkylene having 1 to 10 carbons, and in the alkylene, at least one of —CH$_2$— may be replaced by —O—, and at least one of hydrogen may be replaced by fluorine; and
a and b are independently 1 or 2, and c is 0, 1 or 2.

4. The liquid crystal composition according to claim 1, comprising:

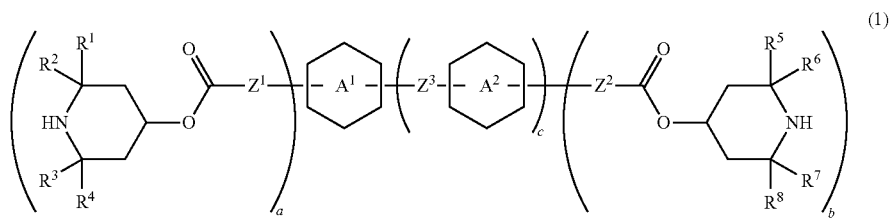

(1)

wherein, in formula (1),
$R^1$, $R^2$, $R^3$, $R^4$, $R^5$, $R^6$, $R^7$ and $R^8$ are independently alkyl having 1 to 4 carbons;
ring $A^1$ and ring $A^2$ are independently 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl or naphthalene-2,7-diyl, and in the rings, at least one of hydrogen may be replaced by fluorine, chlorine, methyl, methoxy, fluoromethyl, difluoromethyl or trifluoromethyl;
$Z^1$, $Z^2$ and $Z^3$ are independently a single bond or alkylene having 1 to 10 carbons, and in the alkylene, at least one of —CH$_2$— may be replaced by —O—, and at least one of hydrogen may be replaced by fluorine; and
a and b are independently 1 or 2, and c is 0, 1 or 2.

5. The liquid crystal composition according to claim 1, further containing at least one compound selected from the group of compounds represented by formulas (5) to (7):

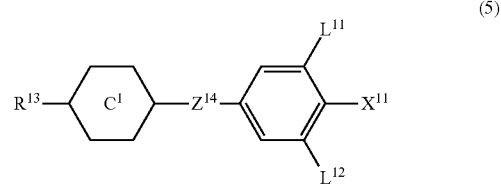

(5)

-continued

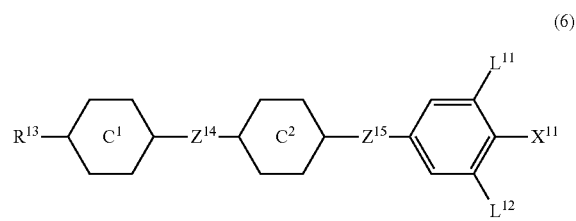

(6)

-continued

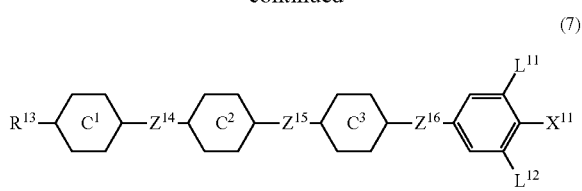

(7)

wherein, in formulas (5) to (7),
$R^{13}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;
$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

pound, a polymerization initiator, a polymerization inhibitor, an optically active compound, an antioxidant, an ultraviolet light absorber, a light stabilizer, a heat stabilizer and an antifoaming agent.

8. A liquid crystal display device, including at least one liquid crystal composition according to claim 1.

9. A compound represented by formulas (1-1) to (1-3):

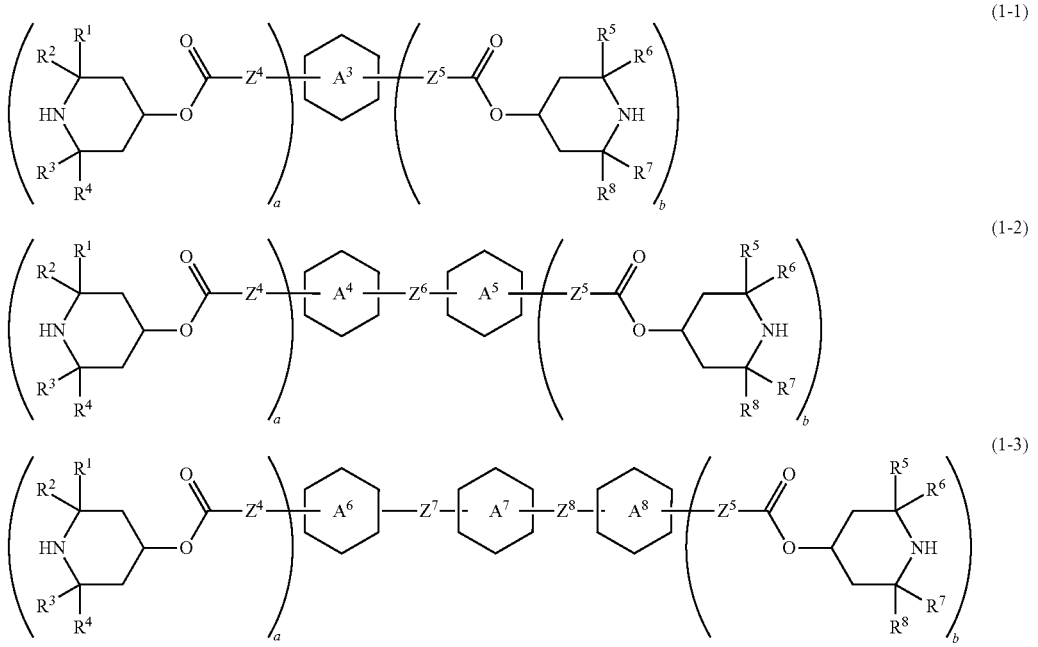

6. The liquid crystal composition according to claim 1, further containing at least one compound selected from the group of compounds represented by formula (8):

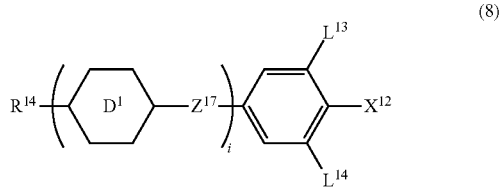

wherein, in formula (8), $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{12}$ is —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, C≡C, —COO—, —$CF_2O$—, —$OCF_2$— or —$CH_2O$—;

$L^{13}$ and $L^{14}$ are independently hydrogen or fluorine; and i is 1, 2, 3 or 4.

7. The liquid crystal composition according to claim 1, further containing at least one of a polymerizable comwherein, in formulas (1-1) to (1-3), $R^1$, $R^2$, $R^3$, $R^4$, $R^5$, $R^6$, $R^7$ and $R^8$ are independently hydrogen or alkyl having 1 to 4 carbons;

ring $A^3$ is decahydronaphthalene-2,6-diyl, 3,4-dihydro-2H-pyran-3,6-diyl, 3,4-dihydro-2H-pyran-2,5-diyl, 3,6-dihydro-2H-pyran-2,5-diyl, 1,3-dioxane-2,5-diyl, tetrahydropyran-2,5-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl, and in the rings, at least one of hydrogen may be replaced by halogen, alkyl having 1 to 5 carbons, alkoxy having 1 to 5 carbons, or alkyl having 1 to 5 carbons in which at least one of hydrogen is replaced by halogen;

ring $A^4$, ring $A^5$, ring $A^6$, ring $A^7$ and ring $A^8$ are independently 1,4-cyclohexylene, 1,4-cyclohexenylene, decahydronaphthalene-2,6-diyl, 3,4-dihydro-2H-pyran-3,6-diyl, 3,4-dihydro-2H-pyran-2,5-diyl, 3,6-dihydro-2H-pyran-2,5-diyl, tetrahydropyran-2,5-diyl, 1,3-dioxane-2,5-diyl, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, pyrimidine-2,5-diyl or pyridine-2,5-diyl, and in the rings, at least one of hydrogen may be replaced by halogen, alkyl having 1 to 5 carbons, alkoxy having 1 to 5 carbons, or alkyl having 1 to 5 carbons in which at least one of hydrogen is replaced by halogen;

$Z^4$, $Z^5$, $Z^6$, $Z^7$ and $Z^8$ are independently a single bond or alkylene having 1 to 10 carbons, and in the alkylene, at least one of —CH$_2$— may be replaced by —O—, —S—, —CO—, —COO— or —OCO—, at least one of —CH$_2$—CH$_2$— may be replaced by —CH=CH— or —C≡C—, and in the groups, at least one of hydrogen may be replaced by fluorine or chlorine; and a and b are independently 1 or 2.

10. The compound according to claim 9, comprising:

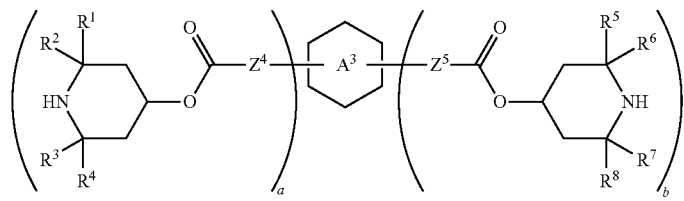

(1-1)

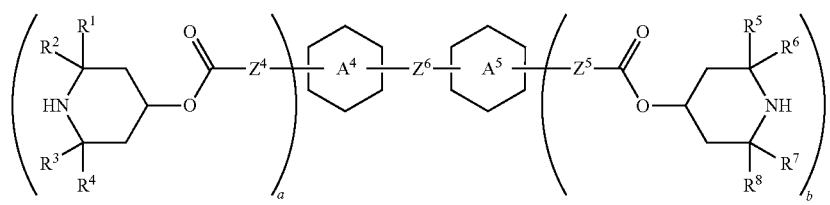

(1-2)

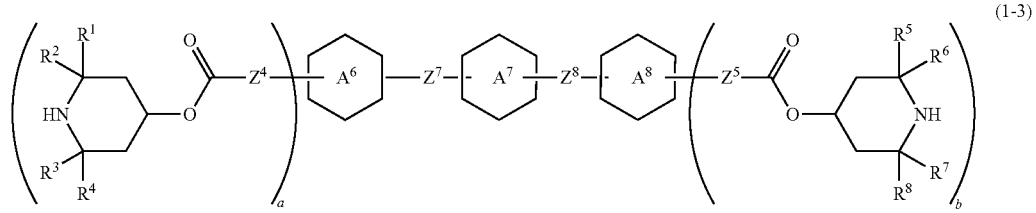

(1-3)

wherein, in formulas (1-1) to (1-3), $R^1$, $R^2$, $R^3$, $R^4$, $R^5$, $R^6$, $R^7$ and $R^8$ are independently hydrogen or alkyl having 1 to 4 carbons;

ring $A^3$ is decahydronaphthalene-2,6-diyl, naphthalene-2,6-diyl, or naphthalene-2,6-diyl in which at least one of hydrogen is replaced by fluorine;

ring $A^4$, ring $A^5$, ring $A^6$, ring $A^7$ and ring $A^8$ are independently 1,4-cyclohexylene, 1,4-cyclohexenylene, decahydronaphthalene-2,6-diyl, 1,4-phenylene, 1,4-phenylene in which at least one of hydrogen is replaced by fluorine, or naphthalene-2,6-diyl;

$Z^4$, $Z^5$, $Z^6$, $Z^7$ and $Z^8$ are independently a single bond or alkylene having 1 to 10 carbons, and in the alkylene, at least one of —CH$_2$— may be replaced by —O—, and at least one of —CH$_2$—CH$_2$— may be replaced by —CH=CH—; and a and b are independently 1 or 2.

11. The compound according to claim 9, comprising:

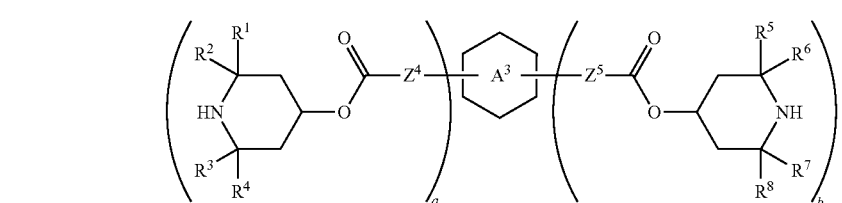

(1-1)

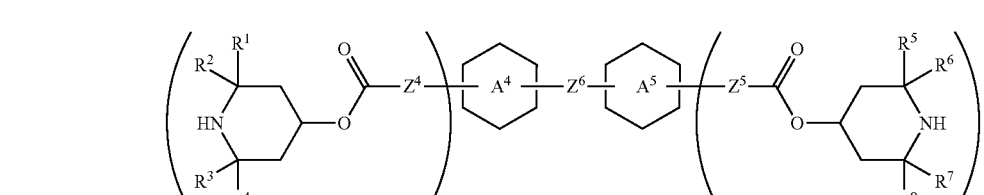

(1-2)

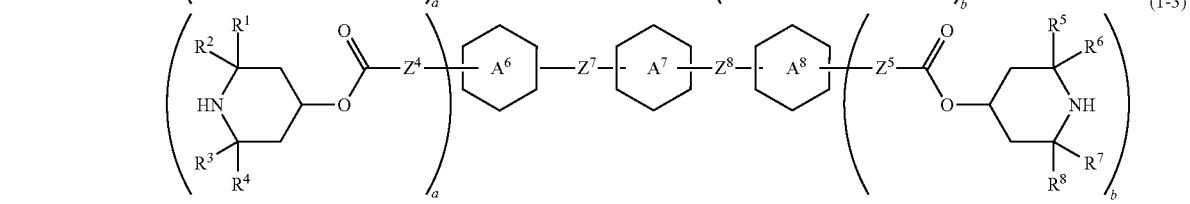

(1-3)

wherein, in formulas (1-1) to (1-3),
$R^1$, $R^2$, $R^3$, $R^4$, $R^5$, $R^6$, $R^7$ and $R^8$ are methyl;
ring $A^3$ is naphthalene-2,6-diyl;
ring $A^4$, ring $A^5$, ring $A^6$, ring $A^7$ and ring $A^8$ are independently 1,4-phenylene, 2-fluoro-1,4-phenylene or naphthalene-2,6-diyl;
$Z^4$, $Z^5$, $Z^6$, $Z^7$ and $Z^8$ are single bonds; and
a and b are independently 1 or 2.

12. The compound according to claim 9, represented by any one of formulas (1-1-1), (1-2-1), (1-2-2), (1-2-3) and (1-2-4):

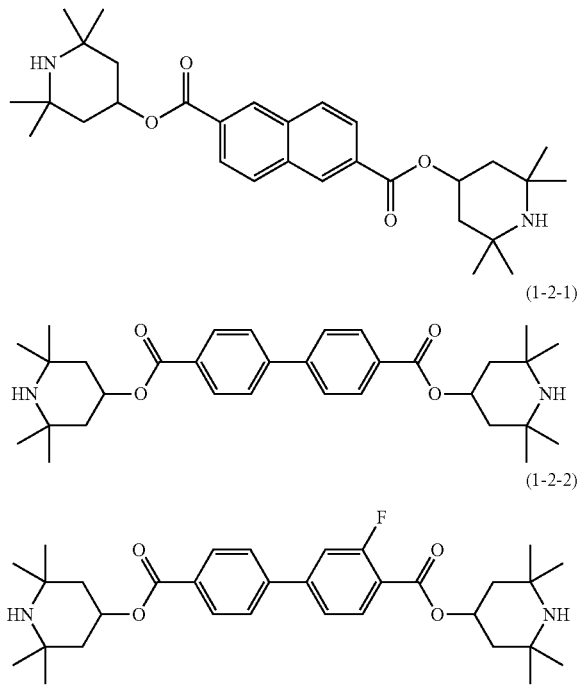

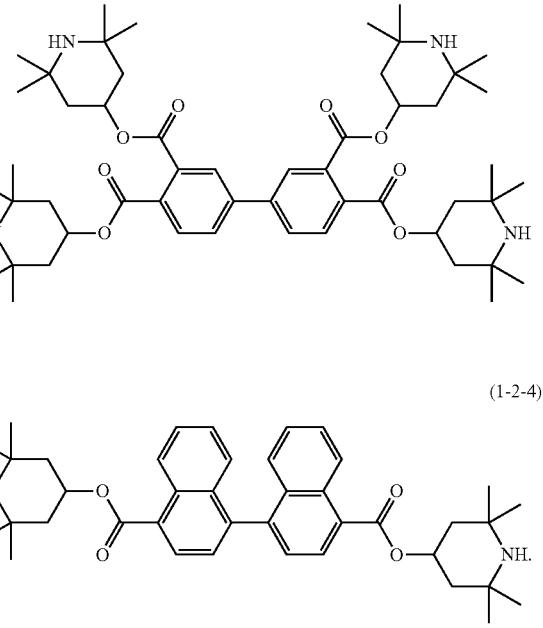

13. A liquid crystal composition, containing at least one compound according to claim 9.

14. A liquid crystal display device, including at least one liquid crystal composition according to claim 13.

* * * * *